(12) United States Patent
Cao et al.

(10) Patent No.: US 7,026,326 B2
(45) Date of Patent: Apr. 11, 2006

(54) SUBSTITUTED HETEROCYCLIC COMPOUNDS AND METHODS OF USE

(75) Inventors: Guo-Qiang Cao, Thousand Oaks, CA (US); Celia Dominguez, Thousand Oaks, CA (US); Martin H. Goldberg, Woodlands Hills, CA (US); Fang-Tsao Hong, Thousand Oaks, CA (US); Kelvin K. C. Sham, Thousand Oaks, CA (US); Seifu Tadesse, Simi Valley, CA (US); Nuria A. Tamayo, Newbury Park, CA (US); Kurt E. Weiler, Thousand Oaks, CA (US); Dawei Zhang, Thousand Oaks, CA (US); Hongyu Liao, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 359 days.

(21) Appl. No.: 10/438,553

(22) Filed: May 13, 2003

(65) Prior Publication Data

US 2005/0038010 A1    Feb. 17, 2005

Related U.S. Application Data

(60) Provisional application No. 60/382,699, filed on May 21, 2002.

(51) Int. Cl.
*A61K 31/505* (2006.01)
(52) U.S. Cl. ........................................ 514/269; 544/242
(58) Field of Classification Search ................ 514/269; 544/242

See application file for complete search history.

(56) References Cited

U.S. PATENT DOCUMENTS

| | | | | |
|---|---|---|---|---|
| 6,096,753 A | * | 8/2000 | Spohr et al. | 514/269 |
| 6,410,729 B1 | * | 6/2002 | Spohr et al. | 544/320 |
| 2004/0116429 A1 | * | 6/2004 | Grote et al. | 514/242 |

FOREIGN PATENT DOCUMENTS

| | | |
|---|---|---|
| WO | WO 95/09917 | 4/1995 |
| WO | WO 96/18412 | 6/1996 |
| WO | WO 97/28828 | 8/1997 |
| WO | WO 97/44453 | 11/1997 |
| WO | WO 98/24477 | 6/1998 |
| WO | WO 98/24780 | 6/1998 |
| WO | WO 98/24782 | 6/1998 |
| WO | WO 98/31820 | 7/1998 |
| WO | WO 98/46257 | 10/1998 |

OTHER PUBLICATIONS

"Studies on anti-platelet agents. IV. A series of 20substituted 4,5-bis(4-methoxyphenyl)pyrimidines as Novel anti-platelet agents." Tanaka et al., Chem. Parm. Bull, vol. 42(9), (1994), pp. 1828-1830, 1834.*

Loetscher, et al., "Efficacy of a chimeric TNFR-IgG fusin protein to inhibit TNF activity in animal models of septic shock." International Congress Series, 2: 455-462 (1993).

Brocks, et al., "A TNF receptor antagonistic scFv, which is not secreted in mammalian cells, is expressed as a soluble mono-and bivalent scFv derivative in insect cells." Immunotechnology, 3: 173-184 (1997).

* cited by examiner

*Primary Examiner*—James O. Wilson
*Assistant Examiner*—Jason H. Johnsen
(74) *Attorney, Agent, or Firm*—Richard V. Person

(57) ABSTRACT

The present invention relates to compounds having the general formula

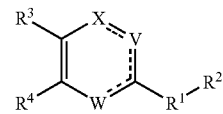

or a pharmaceutically acceptable salt thereof, wherein $R^1$ is a saturated or unsaturated 5-, 6- or 7-membered, ring containing 0, 1, 2 or 3 atoms selected from N, O and S, wherein the ring may be fused with a benzo group, and is substituted by 0, 1 or 2 oxo groups, and wherein $R^1$ is additionally substituted; and $R^2$ is a substituted $C_{1-6}$alkyl. Also included is a method of prophylaxis or treatment of inflammation, rheumatoid arthritis, Pagets disease, osteoporosis, multiple myeloma, uveititis, acute or chronic myelogenous leukemia, pancreatic β cell destruction, osteoarthritis, rheumatoid spondylitis, gouty arthritis, inflammatory bowel disease, adult respiratory distress syndrome (ARDS), psoriasis, Crohn's disease, allergic rhinitis, ulcerative colitis, anaphylaxis, contact dermatitis, asthma, muscle degeneration, cachexia, Reiter's syndrome, type I diabetes, type II diabetes, bone resorption diseases, graft vs. host reaction, Alzheimer's disease, stroke, myocardial infarction, ischemia reperfusion injury, atherosclerosis, brain trauma, multiple sclerosis, cerebral malaria, sepsis, septic shock, toxic shock syndrome, fever, myalgias due to HIV-1, HIV-2, HIV-3, cytomegalovirus (CMV), influenza, adenovirus, the herpes viruses or herpes zoster infection in a mammal comprising administering an effective amount a compound as described above.

8 Claims, No Drawings

SUBSTITUTED HETEROCYCLIC COMPOUNDS AND METHODS OF USE

This application claims the benefit of U.S. Provisional Application No. 60/382,699, filed May 21, 2002, which is hereby incorporated by reference.

BACKGROUND OF THE INVENTION

The present invention comprises a new class of compounds useful in treating diseases, such as TNF-α, IL-1β, IL-6 and/or IL-8 mediated diseases and other maladies, such as pain and diabetes. In particular, the compounds of the invention are useful for the prophylaxis and treatment of diseases or conditions involving inflammation. This invention also relates to intermediates and processes useful in the preparation of such compounds.

Interleukin-1 (IL-1) and Tumor Necrosis Factor α(TNF-α) are pro-inflammatory cytokines secreted by a variety of cells, including monocytes and macrophages, in response to many inflammatory stimuli (e.g., lipopolysaccharide—LPS) or external cellular stress (e.g., osmotic shock and peroxide).

Elevated levels of TNF-αand/or IL-1 over basal levels have been implicated in mediating or exacerbating a number of disease states including rheumatoid arthritis; Pagets disease; osteoporosis; multiple myeloma; uveititis; acute and chronic myelogenous leukemia; pancreatic β cell destruction; osteoarthritis; rheumatoid spondylitis; gouty arthritis; inflammatory bowel disease; adult respiratory distress syndrome (ARDS); psoriasis; Crohns disease; allergic rhinitis; ulcerative colitis; anaphylaxis; contact dermatitis; asthma; muscle degeneration; cachexia; Reiters syndrome; type I and type II diabetes; bone resorption diseases; graft vs. host reaction; ischemia reperfusion injury; atherosclerosis; brain trauma; multiple sclerosis; cerebral malaria; sepsis; septic shock; toxic shock syndrome; fever, and myalgias due to infection. HIV-1, HIV-2, HIV-3, cytomegalovirus (CMV), influenza, adenovirus, the herpes viruses (including HSV-1, HSV-2), and herpes zoster are also exacerbated by TNF-α.

It has been reported that TNF-α plays a role in head trauma, stroke, and ischemia. For instance, in animal models of head trauma (rat), TNF-α levels increased in the contused hemisphere (Shohami et al., *J. Cereb. Blood Flow Metab.* 14, 615 (1994)). In a rat model of ischemia wherein the middle cerebral artery was occluded, the levels of TNF-α mRNA of TNF-α increased (Feurstein et al., *Neurosci. Lett.* 164, 125 (1993)). Administration of TNF-α into the rat cortex has been reported to result in significant neutrophil accumulation in capillaries and adherence in small blood vessels. TNF-α promotes the infiltration of other cytokines (IL-1β, IL-6) and also chemokines, which promote neutrophil infiltration into the infarct area (Feurstein, *Stroke* 25, 1481 (1994)). TNF-α has also been implicated to play a role in type II diabetes (Endocrinol. 130, 43–52, 1994; and Endocrinol. 136, 1474–1481, 1995).

TNF-α appears to play a role in promoting certain viral life cycles and disease states associated with them. For instance, TNF-α secreted by monocytes induced elevated levels of HIV expression in a chronically infected T cell clone (Clouse et al., *J. Immunol.* 142, 431 (1989)). Lahdevirta et al., (*Am. J. Med.* 85, 289 (1988)) discussed the role of TNF-α in the HIV associated states of cachexia and muscle degradation.

TNF-α is upstream in the cytokine cascade of inflammation. As a result, elevated levels of TNF-α may lead to elevated levels of other inflammatory and proinflammatory cytokines, such as L-1, L-6, and L-8.

Elevated levels of L-1 over basal levels have been implicated in mediating or exacerbating a number of disease states including rheumatoid arthritis; osteoarthritis; rheumatoid spondylitis; gouty arthritis; inflammatory bowel disease; adult respiratory distress syndrome (ARDS); psoriasis; Crohn's disease; ulcerative colitis; anaphylaxis; muscle degeneration; cachexia; Reiter's syndrome; type I and type II diabetes; bone resorption diseases; ischemia reperfusion injury; atherosclerosis; brain trauma; multiple sclerosis; sepsis; septic shock; and toxic shock syndrome. Viruses sensitive to TNF-α inhibition, e.g., HIV-1, HIV-2, HIV-3, are also affected by IL-1.

TNF-α and L-1 appear to play a role in pancreatic β cell destruction and diabetes. Pancreatic β cells produce insulin which helps mediate blood glucose homeostasis. Deterioration of pancreatic β cells often accompanies type I diabetes. Pancreatic β cell functional abnormalities may occur in patients with type II diabetes. Type II diabetes is characterized by a functional resistance to insulin. Further, type II diabetes is also often accompanied by elevated levels of plasma glucagon and increased rates of hepatic glucose production. Glucagon is a regulatory hormone that attenuates liver gluconeogenesis inhibition by insulin. Glucagon receptors have been found in the liver, kidney and adipose tissue. Thus glucagon antagonists are useful for attenuating plasma glucose levels (WO 97/16442, incorporated herein by reference in its entirety). By antagonizing the glucagon receptors, it is thought that insulin responsiveness in the liver will improve, thereby decreasing gluconeogenesis and lowering the rate of hepatic glucose production.

In rheumatoid arthritis models in animals, multiple intra-articular injections of IL-1 have led to an acute and destructive form of arthritis (Chandrasekhar et al., *Clinical Immunol Immunopathol.* 55, 382 (1990)). In studies using cultured rheumatoid synovial cells, IL-1 is a more potent inducer of stromelysin than is TNF-α (Firestein, *Am. J. Pathol.* 140, 1309 (1992)). At sites of local injection, neutrophil, lymphocyte, and monocyte emigration has been observed. The emigration is attributed to the induction of chemokines (e.g., IL-8), and the up-regulation of adhesion molecules (Dinarello, *Eur. Cytokine Netw.* 5, 517–531 (1994)).

IL-1 also appears to play a role in promoting certain viral life cycles. For example, cytokine-induced increase of HIV expression in a chronically infected macrophage line has been associated with a concomitant and selective increase in IL-1 production (Folks et al., *J. Immunol.* 136, 40 (1986)). Beutler et al. (*J. Immunol.* 135, 3969 (1985)) discussed the role of IL-1 in cachexia. Baracos et al. (*New Eng. J. Med.* 308, 553 (1983)) discussed the role of IL-1 in muscle degeneration.

In rheumatoid arthritis, both IL-1 and TNF-α induce synoviocytes and chondrocytes to produce collagenase and neutral proteases, which leads to tissue destruction within the arthritic joints. In a model of arthritis (collagen-induced arthritis (CIA) in rats and mice), intra-articular administration of TNF-α either prior to or after the induction of CIA led to an accelerated onset of arthritis and a more severe course of the disease (Brahn et al., *Lymphokine Cytokine Res.* 11, 253 (1992); and Cooper, *Clin. Exp. Immunol.* 898, 244 (1992)).

IL-8 has been implicated in exacerbating and/or causing many disease states in which massive neutrophil infiltration into sites of inflammation or injury (e.g., ischemia) is mediated by the chemotactic nature of IL-8, including, but not limited to, the following: asthma, inflammatory bowel disease, psoriasis, adult respiratory distress syndrome, cardiac and renal reperfusion injury, thrombosis and glomerulonephritis. In addition to the chemotaxis effect on neutrophils, IL-8 also has the ability to activate neutrophils. Thus, reduction in IL-8 levels may lead to diminished neutrophil infiltration.

Several approaches have been taken to block the effect of TNF-α. One approach involves using soluble receptors for TNF-α (e.g., TNFR-55 or TNFR-75), which have demonstrated efficacy in animal models of TNF-α-mediated disease states. A second approach to neutralizing TNF-α using a monoclonal antibody specific to TNF-α, cA2, has demonstrated improvement in swollen joint count in a Phase II human trial of rheumatoid arthritis (Feldmann et al., *Immunological Reviews*, pp. 195–223 (1995)). These approaches block the effects of TNF-α and IL-1 by either protein sequestration or receptor antagonism.

U.S. Pat. No. 5,100,897, incorporated herein by reference in its entirety, describes pyrimidinone compounds useful as angiotensin II antagonists wherein one of the pyrimidinone ring nitrogen atoms is substituted with a substituted phenylmethyl or phenethyl radical.

U.S. Pat. No. 5,162,325, incorporated herein by reference in its entirety, describes pyrimidinone compounds useful as angiotensin II antagonists wherein one of the pyrimidinone ring nitrogen atoms is substituted with a substituted phenylmethyl radical.

EP 481448, incorporated herein by reference in its entirety, describes pyrimidinone compounds useful as angiotensin II antagonists wherein one of the pyrimidinone ring nitrogen atoms is substituted with a substituted phenyl, phenylmethyl or phenethyl radical.

CA 2,020,370, incorporated herein by reference in its entirety, describes pyrimidinone compounds useful as angiotensin II antagonists wherein one of the pyrimidinone ring nitrogen atoms is substituted with a substituted biphenylaliphatic hydrocarbon radical.

BRIEF DESCRIPTION OF THE INVENTION

The present invention comprises a new class of compounds useful in the prophylaxis and treatment of diseases, such as TNF-α, IL-1β, IL-6 and/or IL-8 mediated diseases and other maladies, such as pain and diabetes. In particular, the compounds of the invention are useful for the prophylaxis and treatment of diseases or conditions involving inflammation. Accordingly, the invention also comprises pharmaceutical compositions comprising the compounds; methods for the prophylaxis and treatment of TNF-α, IL-1β, IL-6 and/or IL-8 mediated diseases, such as inflammatory, pain and diabetes diseases, using the compounds and compositions of the invention, and intermediates and processes useful for the preparation of the compounds of the invention.

The compounds of the invention are represented by the following general structure:

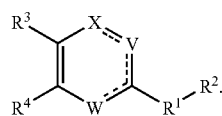

The foregoing merely summarizes certain aspects of the invention and is not intended, nor should it be construed, as limiting the invention in any way. All patents and other publications recited herein are hereby incorporated by reference in their entirety.

DETAILED DESCRIPTION OF THE INVENTION

In accordance with the present invention, there is provided compounds of the formula:

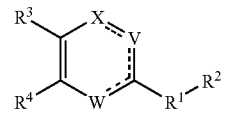

or a pharmaceutically acceptable salt thereof, wherein
n is 0, 1 or 2;
$R^1$ is a saturated or unsaturated 5-, 6- or 7-membered, ring containing 0, 1, 2 or 3 atoms selected from N, O and S, wherein the ring may be fused with a benzo group, and is substituted by 0, 1 or 2 oxo groups, and wherein $R^1$ is additionally substituted by 0, 1, 2 or 3 substituents selected from $R^d$ and $C_{1-4}$alkyl$R^d$;
$R^2$ is $C_{1-6}$alkyl substituted by 1, 2 or 3 $R^d$ groups and 0 or 1 $R^c$ groups, which are substituted by 0, 1 or 2 $R^d$ groups, wherein $R^2$ is not —C(=O)Obenzyl; and wherein —$R^1$–$R^2$ is not 3-benzylpiperazin-1-yl; and wherein if $R^3$ and $R^4$ are both 4-methylphenyl then —$R^1$–$R^2$ is not 4-(hydroxymethyl)piperidin-1-yl;
$R^3$ is $R^c$ substituted by 0, 1, 2 or 3 substituents selected from $R^f$ and $R^d$;
$R^4$ is $R^c$ substituted by 0, 1, 2 or 3 substituents selected from $R^f$ and $R^d$ not including 1-phenylethylamino; provided that the total number of $R^c$ groups substituted on each of $R^3$ and $R^4$ is 0 or 1;
$R^5$ is independently at each instance H, $C_{1-8}$alkyl or $C^{1-6}$alkyl$R^c$ both of which are substituted by 0, 1, 2 or 3 substituents selected from $R^d$;
$R^6$ is independently at each instance $C_{1-8}$alkyl or $C^{1-6}$alkyl$R^c$ both of which are substituted by 0, 1, 2 or 3 substituents selected from $R^d$; or $R^6$ is $R^d$;
$R^7$ is independently hydrogen, —$C_{1-6}$alkyl or —$C^{1-4}$alkyl$R^c$ wherein any carbon atom in the preceding is substituted by 0–3 substituents selected from $R^d$;
$R^a$ is independently at each instance H or $R^b$;
$R^b$ is independently at each instance $C_{1-8}$alkyl, $R^c$ or $C^{1-4}$alkyl$R^c$ each of which is substituted by 0, 1, 2 or 3 substituents independently selected from $R^d$;
$R^c$ is independently at each instance aryl or a saturated or unsaturated 5-, 6- or 7-membered heterocyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein any heterocyclic ring is substituted by 0, 1 or 2 oxo groups;
$R^d$ is independently in each instance $C_{1-6}$alkyl, halo, $C_{1-4}$haloalkyl, cyano, —C(=O)$R^f$, —C(=O)O$R^e$, —C(=O)N$R^gR^g$, —C(=N$R^g$)N$R^gR^g$, —O$R^e$, —OC(=O)$R^e$, —OC(=O)N$R^gR^g$, —OC(=O)N($R^h$)S(=O)$_2R^f$, —S$R^e$, —S(=O)$R^f$, —S(=O)$_2R^f$, —S(=O)$_2$N$R^gR^g$, —S(=O)$_2$N($R^h$)C(=O)$R^f$, —S(=O)$_2$N($R^h$)C(=O)O$R^f$, —S(=)$_2$—N($R^h$)C(=O)N$R^gR^g$, —N$R^gR^g$, —N($R^h$)C(=O)$R^e$, —N($R^h$)C(=O)O$R^f$, —N($R^h$)C(=O)N$R^gR^g$, —N($R^h$)C(=N$R^g$)N$R^gR^g$, —N($R^h$)S(=O)$_2R^f$ or —N($R^h$)S(=O)$_2$N$R^gR^g$;
$R^e$ is independently at each instance hydrogen or $R^f$;
$R^f$ is independently at each instance $R^c$ or $C_{1-8}$alkyl, either of which is substituted by 0–3 substituents selected from —NR$^g$R$^g$, —C(=O)OR$^i$, —OR$^i$, —N(R$^i$)C(=O)R$^k$, —N(R$^i$)C(=O)OR$^i$, —N(R$^i$)S(=O)$_2$R$^k$, —S(=O)$_n$R$^k$, cyano, halo, —OC$_{1-4}$alkylR$^c$, —S(=O)$_n$C$_{1-4}$alkylR$^c$ and R$^c$, wherein any R$^c$ in R$^f$ may be further substituted by C$_{1-8}$alkyl or C$_{1-4}$haloalkyl;

R$^g$ is independently at each instance hydrogen, R$^c$, C$_{1-10}$alkyl or —C$_{1-4}$alkylR$^c$, wherein the each is substituted by 0–3 substituents selected from —NR$^i$R$^i$, —N(R$^i$)C(=O)R$^k$, —N(R$^i$)C(=O)OR$^k$, —N(R$^i$)S(=O)$_2$R$^k$, —OR$^i$, —S(=O)$_n$R$^k$, cyano, C$_{1-8}$alkyl and C$_{1-4}$haloalkyl;

R$^h$ is independently at each instance hydrogen, C$_{1-8}$alkyl or C$_{1-4}$alkylR$^c$ each of which is substituted by 0–3 substituents selected from —NR$^i$R$^i$, —N(R$^i$)C(=O)R$^k$, —N(R$^i$)C(=O)OR$^k$, —N(R$^i$)S(=O)$_2$R$^k$, —OR$^i$, —S(=O)$_n$R$^k$, cyano, C$_{1-8}$alkyl and C$_{1-4}$haloalkyl;

R$^i$ is R$^k$ or hydrogen;

R$^k$ is C$_{1-6}$alkyl, phenyl or benzyl;

V is —N=, —NR$^5$—, —CR$^6$=, C=O, C=S or C=NR$^7$;

W is —N=, —NR$^5$—, —CR$^6$=, C=O, C=S or C=NR$^7$; and

X is —N=, —NR$^5$—, —CR$^6$=, C=O, C=S or C=NR$^7$; wherein the total number of —NR$^5$—, C=O, C=S or C=NR$^7$ groups represented by V, W and X must be 0 or 2; and at least one of V, W and X contains a N atom.

In another embodiment, in conjunction with any of the above or below embodiments, V is —N=; W is —N= or —CR$^6$=; and X is —N= or —CR$^6$=.

In another embodiment, in conjunction with any of the above or below embodiments, V is C=O, C=S or C=NR$^7$; W is —N= or —CR$^6$=; and X is —NR$^5$—.

In another embodiment, in conjunction with any of the above or below embodiments, V is —NR$^5$—; W is —N= or —CR$^6$=; and X is C=O, C=S or C=NR$^7$.

Sub-embodiment A: In another embodiment, in conjunction with any of the above or below embodiments, R$^1$ is a saturated or unsaturated 5-, 6- or 7-membered, ring containing 0, 1, 2 or 3 atoms selected from N, O and S, wherein the ring may be fused with a benzo group, and is substituted by 0, 1 or 2 oxo groups, and wherein R$^1$ is additionally substituted by 0, 1, 2 or 3 substituents selected from R$^d$ and C$_{1-4}$alkylR$^d$;

Sub-embodiment B: In another embodiment, in conjunction with any of the above or below embodiments, R$^1$ is a saturated or unsaturated 5-, 6- or 7-membered, ring containing 1, 2 or 3 atoms selected from N, O and S, wherein the ring may be fused with a benzo group, and is substituted by 0, 1 or 2 oxo groups, and wherein R$^1$ is additionally substituted by 0, 1, 2 or 3 substituents selected from R$^d$ and C$_{1-4}$alkylR$^d$.

Sub-embodiment C: In another embodiment, in conjunction with any of the above or below embodiments, R$^1$ is a saturated or unsaturated 5-, 6- or 7-membered, ring containing 1 or 2 N atoms and 0 or 1 atoms selected from O and S, wherein the ring may be fused with a benzo group, and is substituted by 0, 1 or 2 oxo groups, and wherein R$^1$ is additionally substituted by 0, 1, 2 or 3 substituents selected from R$^d$ and C$_{1-4}$alkylR$^d$.

Sub-embodiment D: In another embodiment, in conjunction with any of the above or below embodiments, R$^1$ is a saturated or unsaturated 5-, 6- or 7-membered, ring containing 1 or 2 N atoms, and is substituted by 0, 1 or 2 oxo groups, and wherein R$^1$ is additionally substituted by 0, 1, 2 or 3 substituents selected from R$^d$ and C$_{1-4}$alkylR$^d$.

Sub-embodiment E: In another embodiment, in conjunction with any of the above or below embodiments, R$^1$ is a saturated or unsaturated 5- or 6-membered, ring containing 1 or 2 N atoms.

Sub-embodiment F: In another embodiment, in conjunction with any of the above or below embodiments, R$^1$ is a saturated 5- or 6-membered, ring containing 1 N atom.

Sub-embodiment G: In another embodiment, in conjunction with any of the above or below embodiments, R$^1$ is piperidine or pyrrolidine.

Sub-embodiment H: In another embodiment, in conjunction with any of the above or below embodiments, R$^2$ is C$_{1-6}$alkyl substituted by 1, 2 or 3 R$^d$ groups and 0 or 1 R$^c$ groups, which are substituted by 0, 1 or 2 R$^d$ groups, wherein R$^2$ is not —C(=O)Obenzyl; and wherein —R$^1$–R$^2$ is not 3-benzylpiperazin-1-yl; and wherein if R$^3$ and R$^4$ are both 4-methylphenyl then —R$^1$–R$^2$ is not 4-(hydroxymethyl) piperidin-1-yl.

Sub-embodiment I: In another embodiment, in conjunction with any of the above or below embodiments, R$^2$ is C$_{1-6}$alkyl substituted by 1 or 2 R$^d$ groups and 1 R$^c$ group, which is substituted by 0, 1 or 2 R$^d$ groups, wherein R$^2$ is not —C(=O)Obenzyl; and wherein —R$^1$–R$^2$ is not 3-benzylpiperazin-1-yl.

Sub-embodiment J: In another embodiment, in conjunction with any of the above or below embodiments, R$^2$ is C$_{1-6}$alkyl substituted by 1, 2 or 3 R$^d$ groups; and wherein R$^3$ and R$^4$ are not both 4-methylphenyl.

Sub-embodiment K: In another embodiment, in conjunction with any of the above or below embodiments, R$^2$ is C$_{1-6}$alkyl substituted by 1 or 2 R$^d$ groups.

Sub-embodiment L: In another embodiment, in conjunction with any of the above or below embodiments, R$^2$ is C$_{1-6}$alkyl substituted by 1 group selected from —OR$^e$ and —NR$^g$R$^g$, and 0 or 1 R$^d$ groups.

Sub-embodiment M: In another embodiment, in conjunction with any of the above or below embodiments, R$^2$ is —(C$_{1-3}$alkyl)O(C$_{1-5}$alkyl) or —(C$_{1-3}$alkyl)—NR$^g$R$^g$.

Sub-embodiment N: In another embodiment, in conjunction with any of the above or below embodiments, R$^3$ is R$^c$ substituted by 0, 1, 2 or 3 substituents selected from R$^f$ and R$^d$.

Sub-embodiment O: In another embodiment, in conjunction with any of the above or below embodiments, R$^3$ is aryl substituted by 0, 1, 2 or 3 substituents selected from R$^f$ and R$^d$; provided that the total number of R$^c$ groups substituted on each of R$^3$ and R$^4$ is 0 or 1.

Sub-embodiment P: In another embodiment, in conjunction with any of the above or below embodiments, R$^3$ is phenyl substituted by 1 or 2 substituents selected from R$^f$ and R$^d$; provided that the total number of R$^c$ groups substituted on each of R$^3$ and R$^4$ is 0 or 1.

Sub-embodiment Q: In another embodiment, in conjunction with any of the above or below embodiments, R$^3$ is phenyl substituted by 1 or 2 substituents independently selected from halo and CF$_3$.

Sub-embodiment R: In another embodiment, in conjunction with any of the above or below embodiments, R$^3$ is naphthyl.

Sub-embodiment S: In another embodiment, in conjunction with any of the above or below embodiments, R$^3$ is aryl substituted by 0, 1, 2 or 3 substituents selected from R$^f$ and R$^d$; and R$^4$ is a saturated or unsaturated 5-, 6- or 7-membered heterocyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein any heterocyclic ring is substituted by 0, 1 or 2 oxo groups; wherein the preceding is substituted by 0, 1, 2 or 3 substituents selected from $R^f$ and $R^d$; provided that the total number of $R^c$ groups substituted on each of $R^3$ and $R^4$ is 0 or 1.

Sub-embodiment T: In another embodiment, in conjunction with any of the above or below embodiments, $R^4$ is $R^c$ substituted by 0, 1, 2 or 3 substituents selected from $R^f$ and $R^d$ not including 1-phenylethylamino; provided that the total number of $R^c$ groups substituted on each of $R^3$ and $R^4$ is 0 or 1.

Sub-embodiment U: In another embodiment, in conjunction with any of the above or below embodiments, $R^4$ is a saturated or unsaturated 5-, 6- or 7-membered heterocyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein any heterocyclic ring is substituted by 0, 1 or 2 oxo groups; wherein the preceding is substituted by 0, 1, 2 or 3 substituents selected from $R^f$ and $R^d$; provided that the total number of $R^c$ groups substituted on each of $R^3$ and $R^4$ is 0 or 1.

Sub-embodiment V: In another embodiment, in conjunction with any of the above or below embodiments, $R^4$ is a unsaturated 6-membered heterocyclic ring containing 1 or 2 N atoms.

Sub-embodiment W: In another embodiment, in conjunction with any of the above or below embodiments, $R^4$ is pyridine or pyrimidine.

As stated above, the above embodiments and sub-embodiments may be used inconjuction with other embodiments and subembodiments listed. The following table is a non-exclusive, non-limiting list of some of the combinations of embodiments:

| Embodiment | V | W | X | $R^1$ | $R^2$ | $R^3$ | $R^4$ |
|---|---|---|---|---|---|---|---|
| 1001 | —$NR^5$— | —N= | C=O | A | H | N | T |
| 1002 | —$NR^5$— | —N= | C=O | A | H | N | V |
| 1003 | —$NR^5$— | —N= | C=O | A | H | Q | T |
| 1004 | —$NR^5$— | —N= | C=O | A | H | Q | V |
| 1005 | —$NR^5$— | —N= | C=O | A | H | R | T |
| 1006 | —$NR^5$— | —N= | C=O | A | H | R | V |
| 1007 | —$NR^5$— | —N= | C=O | A | L | N | T |
| 1008 | —$NR^5$— | —N= | C=O | A | L | N | V |
| 1009 | —$NR^5$— | —N= | C=O | A | L | Q | T |
| 1010 | —$NR^5$— | —N= | C=O | A | L | Q | V |
| 1011 | —$NR^5$— | —N= | C=O | A | L | R | T |
| 1012 | —$NR^5$— | —N= | C=O | A | L | R | V |
| 1013 | —$NR^5$— | —N= | C=O | A | M | N | T |
| 1014 | —$NR^5$— | —N= | C=O | A | M | N | V |
| 1015 | —$NR^5$— | —N= | C=O | A | M | Q | T |
| 1016 | —$NR^5$— | —N= | C=O | A | M | Q | V |
| 1017 | —$NR^5$— | —N= | C=O | A | M | R | T |
| 1018 | —$NR^5$— | —N= | C=O | A | M | R | V |
| 1019 | —$NR^5$— | —N= | C=O | B | H | N | T |
| 1020 | —$NR^5$— | —N= | C=O | B | H | N | V |
| 1021 | —$NR^5$— | —N= | C=O | B | H | Q | T |
| 1022 | —$NR^5$— | —N= | C=O | B | H | Q | V |
| 1023 | —$NR^5$— | —N= | C=O | B | H | R | T |
| 1024 | —$NR^5$— | —N= | C=O | B | H | R | V |
| 1025 | —$NR^5$— | —N= | C=O | B | L | N | T |
| 1026 | —$NR^5$— | —N= | C=O | B | L | N | V |
| 1027 | —$NR^5$— | —N= | C=O | B | L | Q | T |
| 1028 | —$NR^5$— | —N= | C=O | B | L | Q | V |
| 1029 | —$NR^5$— | —N= | C=O | B | L | R | T |
| 1030 | —$NR^5$— | —N= | C=O | B | L | R | V |
| 1031 | —$NR^5$— | —N= | C=O | B | M | N | T |
| 1032 | —$NR^5$— | —N= | C=O | B | M | N | V |
| 1033 | —$NR^5$— | —N= | C=O | B | M | Q | T |
| 1034 | —$NR^5$— | —N= | C=O | B | M | Q | V |
| 1035 | —$NR^5$— | —N= | C=O | B | M | R | T |
| 1036 | —$NR^5$— | —N= | C=O | B | M | R | V |
| 1037 | —$NR^5$— | —N= | C=O | F | H | N | T |
| 1038 | —$NR^5$— | —N= | C=O | F | H | N | V |
| 1039 | —$NR^5$— | —N= | C=O | F | H | Q | T |
| 1040 | —$NR^5$— | —N= | C=O | F | H | Q | V |
| 1041 | —$NR^5$— | —N= | C=O | F | H | R | T |
| 1042 | —$NR^5$— | —N= | C=O | F | H | R | V |
| 1043 | —$NR^5$— | —N= | C=O | F | L | N | T |
| 1044 | —$NR^5$— | —N= | C=O | F | L | N | V |
| 1045 | —$NR^5$— | —N= | C=O | F | L | Q | T |
| 1046 | —$NR^5$— | —N= | C=O | F | L | Q | V |
| 1047 | —$NR^5$— | —N= | C=O | F | L | R | T |
| 1048 | —$NR^5$— | —N= | C=O | F | L | R | V |
| 1049 | —$NR^5$— | —N= | C=O | F | M | N | T |
| 1050 | —$NR^5$— | —N= | C=O | F | M | N | V |
| 1051 | —$NR^5$— | —N= | C=O | F | M | Q | T |
| 1052 | —$NR^5$— | —N= | C=O | F | M | Q | V |
| 1053 | —$NR^5$— | —N= | C=O | F | M | R | T |
| 1054 | —$NR^5$— | —N= | C=O | F | M | R | V |
| 1055 | —$NR^5$— | —$CR^6$= | C=O | A | H | N | T |
| 1056 | —$NR^5$— | —$CR^6$= | C=O | A | H | N | V |
| 1057 | —$NR^5$— | —$CR^6$= | C=O | A | H | Q | T |
| 1058 | —$NR^5$— | —$CR^6$= | C=O | A | H | Q | V |
| 1059 | —$NR^5$— | —$CR^6$= | C=O | A | H | R | T |
| 1060 | —$NR^5$— | —$CR^6$= | C=O | A | H | R | V |
| 1061 | —$NR^5$— | —$CR^6$= | C=O | A | L | N | T |
| 1062 | —$NR^5$— | —$CR^6$= | C=O | A | L | N | V |
| 1063 | —$NR^5$— | —$CR^6$= | C=O | A | L | Q | T |
| 1064 | —$NR^5$— | —$CR^6$= | C=O | A | L | Q | V |
| 1065 | —$NR^5$— | —$CR^6$= | C=O | A | L | R | T |
| 1066 | —$NR^5$— | —$CR^6$= | C=O | A | L | R | V |
| 1067 | —$NR^5$— | —$CR^6$= | C=O | A | M | N | T |
| 1068 | —$NR^5$— | —$CR^6$= | C=O | A | M | N | V |
| 1069 | —$NR^5$— | —$CR^6$= | C=O | A | M | Q | T |
| 1070 | —$NR^5$— | —$CR^6$= | C=O | A | M | Q | V |
| 1071 | —$NR^5$— | —$CR^6$= | C=O | A | M | R | T |
| 1072 | —$NR^5$— | —$CR^6$= | C=O | A | M | R | V |
| 1073 | —$NR^5$— | —$CR^6$= | C=O | B | H | N | T |
| 1074 | —$NR^5$— | —$CR^6$= | C=O | B | H | N | V |
| 1075 | —$NR^5$— | —$CR^6$= | C=O | B | H | Q | T |
| 1076 | —$NR^5$— | —$CR^6$= | C=O | B | H | Q | V |
| 1077 | —$NR^5$— | —$CR^6$= | C=O | B | H | R | T |
| 1078 | —$NR^5$— | —$CR^6$= | C=O | B | H | R | V |
| 1079 | —$NR^5$— | —$CR^6$= | C=O | B | L | N | T |
| 1080 | —$NR^5$— | —$CR^6$= | C=O | B | L | N | V |
| 1081 | —$NR^5$— | —$CR^6$= | C=O | B | L | Q | T |
| 1082 | —$NR^5$— | —$CR^6$= | C=O | B | L | Q | V |
| 1083 | —$NR^5$— | —$CR^6$= | C=O | B | L | R | T |
| 1084 | —$NR^5$— | —$CR^6$= | C=O | B | L | R | V |
| 1085 | —$NR^5$— | —$CR^6$= | C=O | B | M | N | T |
| 1086 | —$NR^5$— | —$CR^6$= | C=O | B | M | N | V |
| 1087 | —$NR^5$— | —$CR^6$= | C=O | B | M | Q | T |
| 1088 | —$NR^5$— | —$CR^6$= | C=O | B | M | Q | V |
| 1089 | —$NR^5$— | —$CR^6$= | C=O | B | M | R | T |
| 1090 | —$NR^5$— | —$CR^6$= | C=O | B | M | R | V |
| 1091 | —$NR^5$— | —$CR^6$= | C=O | F | H | N | T |
| 1092 | —$NR^5$— | —$CR^6$= | C=O | F | H | N | V |
| 1093 | —$NR^5$— | —$CR^6$= | C=O | F | H | Q | T |
| 1094 | —$NR^5$— | —$CR^6$= | C=O | F | H | Q | V |
| 1095 | —$NR^5$— | —$CR^6$= | C=O | F | H | R | T |
| 1096 | —$NR^5$— | —$CR^6$= | C=O | F | H | R | V |
| 1097 | —$NR^5$— | —$CR^6$= | C=O | F | L | N | T |
| 1098 | —$NR^5$— | —$CR^6$= | C=O | F | L | N | V |
| 1099 | —$NR^5$— | —$CR^6$= | C=O | F | L | Q | T |
| 1100 | —$NR^5$— | —$CR^6$= | C=O | F | L | Q | V |
| 1101 | —$NR^5$— | —$CR^6$= | C=O | F | L | R | T |
| 1001 | —$NR^5$— | —$CR^6$= | C=O | F | L | R | V |
| 1002 | —$NR^5$— | —$CR^6$= | C=O | F | M | N | T |
| 1003 | —$NR^5$— | —$CR^6$= | C=O | F | M | N | V |
| 1004 | —$NR^5$— | —$CR^6$= | C=O | F | M | Q | T |
| 1005 | —$NR^5$— | —$CR^6$= | C=O | F | M | Q | V |
| 1006 | —$NR^5$— | —$CR^6$= | C=O | F | M | R | T |
| 1007 | —$NR^5$— | —$CR^6$= | C=O | F | M | R | V |
| 1008 | C=O | —$CR^6$= | —$NR^5$— | A | H | N | T |
| 1009 | C=O | —$CR^6$= | —$NR^5$— | A | H | N | V |

-continued

| Embodiment | V | W | X | R¹ | R² | R³ | R⁴ |
|---|---|---|---|---|---|---|---|
| 1010 | C=O | —CR⁶= | —NR⁵— | A | H | Q | T |
| 1011 | C=O | —CR⁶= | —NR⁵— | A | H | Q | V |
| 1012 | C=O | —CR⁶= | —NR⁵— | A | H | R | T |
| 1013 | C=O | —CR⁶= | —NR⁵— | A | H | R | V |
| 1014 | C=O | —CR⁶= | —NR⁵— | A | L | N | T |
| 1015 | C=O | —CR⁶= | —NR⁵— | A | L | N | V |
| 1016 | C=O | —CR⁶= | —NR⁵— | A | L | Q | T |
| 1017 | C=O | —CR⁶= | —NR⁵— | A | L | Q | V |
| 1018 | C=O | —CR⁶= | —NR⁵— | A | L | R | T |
| 1019 | C=O | —CR⁶= | —NR⁵— | A | L | R | V |
| 1020 | C=O | —CR⁶= | —NR⁵— | A | M | N | T |
| 1021 | C=O | —CR⁶= | —NR⁵— | A | M | N | V |
| 1022 | C=O | —CR⁶= | —NR⁵— | A | M | Q | T |
| 1023 | C=O | —CR⁶= | —NR⁵— | A | M | Q | V |
| 1024 | C=O | —CR⁶= | —NR⁵— | A | M | R | T |
| 1025 | C=O | —CR⁶= | —NR⁵— | A | M | R | V |
| 1026 | C=O | —CR⁶= | —NR⁵— | B | H | N | T |
| 1027 | C=O | —CR⁶= | —NR⁵— | B | H | N | V |
| 1028 | C=O | —CR⁶= | —NR⁵— | B | H | Q | T |
| 1029 | C=O | —CR⁶= | —NR⁵— | B | H | Q | V |
| 1030 | C=O | —CR⁶= | —NR⁵— | B | H | R | T |
| 1031 | C=O | —CR⁶= | —NR⁵— | B | H | R | V |
| 1032 | C=O | —CR⁶= | —NR⁵— | B | L | N | T |
| 1033 | C=O | —CR⁶= | —NR⁵— | B | L | N | V |
| 1034 | C=O | —CR⁶= | —NR⁵— | B | L | Q | T |
| 1035 | C=O | —CR⁶= | —NR⁵— | B | L | Q | V |
| 1036 | C=O | —CR⁶= | —NR⁵— | B | L | R | T |
| 1037 | C=O | —CR⁶= | —NR⁵— | B | L | R | V |
| 1038 | C=O | —CR⁶= | —NR⁵— | B | M | N | T |
| 1039 | C=O | —CR⁶= | —NR⁵— | B | M | N | V |
| 1040 | C=O | —CR⁶= | —NR⁵— | B | M | Q | T |
| 1041 | C=O | —CR⁶= | —NR⁵— | B | M | Q | V |
| 1042 | C=O | —CR⁶= | —NR⁵— | B | M | R | T |
| 1043 | C=O | —CR⁶= | —NR⁵— | B | M | R | V |
| 1044 | C=O | —CR⁶= | —NR⁵— | F | H | N | T |
| 1045 | C=O | —CR⁶= | —NR⁵— | F | H | N | V |
| 1046 | C=O | —CR⁶= | —NR⁵— | F | H | Q | T |
| 1047 | C=O | —CR⁶= | —NR⁵— | F | H | Q | V |
| 1048 | C=O | —CR⁶= | —NR⁵— | F | H | R | T |
| 1049 | C=O | —CR⁶= | —NR⁵— | F | H | R | V |
| 1050 | C=O | —CR⁶= | —NR⁵— | F | L | N | T |
| 1051 | C=O | —CR⁶= | —NR⁵— | F | L | N | V |
| 1052 | C=O | —CR⁶= | —NR⁵— | F | L | Q | T |
| 1053 | C=O | —CR⁶= | —NR⁵— | F | L | Q | V |
| 1054 | C=O | —CR⁶= | —NR⁵— | F | L | R | T |
| 1055 | C=O | —CR⁶= | —NR⁵— | F | L | R | V |
| 1056 | C=O | —CR⁶= | —NR⁵— | F | M | N | T |
| 1057 | C=O | —CR⁶= | —NR⁵— | F | M | N | V |
| 1058 | C=O | —CR⁶= | —NR⁵— | F | M | Q | T |
| 1059 | C=O | —CR⁶= | —NR⁵— | F | M | Q | V |
| 1060 | C=O | —CR⁶= | —NR⁵— | F | M | R | T |
| 1061 | C=O | —CR⁶= | —NR⁵— | F | M | R | V |

In another embodiment, the compound is selected from:

5-(4-Chloro-phenyl)-2-[2-(R)-isopropylamino-methyl)-pyrrolidin-1-yl]-3-methyl-6-pyridin-4-yl-3H-pyrimidin-4-one;

5-(4-Chloro-phenyl)-2-[2-(S)-isopropylamino-methyl)-pyrrolidin-1-yl]-3-methyl-6-pyridin-4-yl-3H-pyrimidin-4-one;

5-(3-Bromo-phenyl)-2-[2-(isopropylamino-methyl)-pyrrolidin-1-yl]-3-methyl-6-pyridin-4-yl-3H-pyrimidin-4-one;

2-[2-(Isopropylamino-methyl)-pyrrolidin-1-yl]-3-methyl-6-pyridin-4-yl-5-(3-vinyl-phenyl)-3H-pyrimidin-4-one;

5-(3-Cyclopropyl-phenyl)-2-[2-(isopropylamino-methyl)-pyrrolidin-1-yl]-3-methyl-6-pyridin-4-yl-3H-pyrimidin-4-one;

2-[2-(Isopropylamino-methyl)-pyrrolidin-1-yl]-3-methyl-6-pyridin-4-yl-5-m-tolyl-3H-pyrimidin-4-one;

2-[2-(Isopropylamino-methyl)-pyrrolidin-1-yl]-3-methyl-5-naphthalen-2-yl-6-pyridin-4-yl-3H-pyrimidin-4-one;

6-(2-Chloro-pyridin-4-yl)-2-(2-methoxymethyl-pyrrolidin-1-yl)-3-methyl-5-m-tolyl-3H-pyrimidin-4-one;

2-(2-Methoxymethyl-pyrrolidin-1-yl)-3-methyl-6-[2-(1-phenyl-ethylamino)-pyridin-4-yl]-5-m-tolyl-3H-pyrimidin-4-one;

1-(2R-Hydroxy-propyl)-1'-methyl-5'-naphthalen-2-yl-1,2,3,4,5,6-hexahydro-1'H-[4,2';4',4'']terpyridin-6'-one;

1-(2S-Hydroxy-propyl)-1'-methyl-5'-naphthalen-2-yl-1,2,3,4,5,6-hexahydro-1'H-[4,2';4',4'']terpyridin-6'-one;

1-(2-Hydroxy-2-methyl-propyl)-1'-methyl-5'-naphthalen-2-yl-1,2,3,4,5,6-hexahydro-1'H-[4,2';4',4'']terpyridin-6'-one;

Isopropyl-[1-(6-naphthalen-2-yl-5-pyridin-4-yl-pyridazin-3-yl)-pyrrolidin-2-ylmethyl]-amine;

6-[5-(Hydroxymethyl)pyrrolidin-3-yl]-1-methyl-3-(2-naphthyl)-4-(4-pyridyl)-hydropyridin-2-one;

6-[5-(Hydroxymethyl)-1-(methylethyl)pyrrolidin-3-yl]-1-methyl-3-(2-naphthyl)-4-(4-pyridyl)hydropyridin-2-one;

3-(4-Chlorophenyl)-6-[2-(hydroxymethyl)pyrrolidinyl]-1-methyl-4-(4-pyridyl)-hydropyridin-2-one;

[(1R)-Benzyl-2-(1'-methyl-5'-naphthalen-2-yl-6'-oxo-3,4,5,6,1',6'-hexahydro-2H-[4,2';4',4'']terpyridin-1-yl)-ethyl]-carbamic acid tert-butyl ester;

1-{(2R)-Amino-3-phenyl-propyl}-1'-methyl-5'-naphthalen-2-yl-1,2,3,4,5,6-hexahydro-1'H-[4,2';4',4'']terpyridin-6'-one;

1-{(2R)-Isopropylamino-3-phenyl-propyl}-1'-methyl-5'-naphthalen-2-yl-1,2,3,4,5,6-hexahydro-1'H-[4,2';4',4''] terpyridin-6'-one;

[(1S)-Benzyl-2-(1'-methyl-5'-naphthalen-2-yl-6'-oxo-3,4,5,6,1',6'-hexahydro-2H-[4,2';4',4'']terpyridin-1-yl)-ethyl]-carbamic acid tert-butyl ester;

1-{(2S)-Amino-3-phenyl-propyl}-1'-methyl-5'-naphthalen-2-yl-1,2,3,4,5,6-hexahydro-1'H-[4,2';4',4'']terpyridin-6'-one;

1-{(2S)-Isopropylamino-3-phenyl-propyl}-1'-methyl-5'-naphthalen-2-yl-1,2,3,4,5,6-hexahydro-1'H-[4,2';4',4''] terpyridin-6'-one;

{2-[3-(1-Methyl-5-naphthalen-2-yl-6-oxo-1,6-dihydro-[4,4']bipyridinyl-2-yl)-pyrrolidin-1-yl]-ethyl}-carbamic acid tert-butyl ester;

6-[1-(2-Hydroxy-propyl)-pyrrolidin-3-yl]-1-methyl-3-naphthalen-2-yl-1H-[4,4']bipyridinyl-2-one;

6-[1-(2-Hydroxy-2-methyl-propyl)-pyrrolidin-3-yl]-1-methyl-3-naphthalen-2-yl-1H-[4,4']bipyridinyl-2-one;

{2-[2-(1-Methyl-5-naphthalen-2-yl-6-oxo-1,6-dihydro-[4,4']bipyridinyl-2-yl)-pyrrolidin-1-yl]-ethyl}-carbamic acid tert-butyl ester;

6-[1-(2-Amino-ethyl)-pyrrolidin-2-yl]-1-methyl-3-naphthalen-2-yl-1H-[4,4']bi-pyridinyl-2-one;

5-Chloro-6-[2-(isopropylamino-methyl)-pyrrolidin-1-yl]-1-methyl-3-naphthalen-2-yl-1H-[4,4']bipyridinyl-2-one;

6-[2-(Isopropylamino-methyl)-pyrrolidin-1-yl]-1-methyl-3-naphthalen-2-yl-1H-4[4,4']bipyridinyl-2-one; and 3-(4-Chlorophenyl)-1-methyl-6-(2-{[(methylethyl)amino]methyl}pyrrolidinyl)-4-(4-pyridyl)hydropyridin-2-one.

Another aspect of the invention relates to a pharmaceutical composition comprising a compound according to any one of the above embodiments and a pharmaceutically acceptable carrier.

Another aspect of the invention relates to a method of prophylaxis or treatment of inflammation comprising administering an effective amount of a compound according to any one of the above embodiments.

Another aspect of the invention relates to a method of prophylaxis or treatment of rheumatoid arthritis, Pagets disease, osteoporosis, multiple myeloma, uveititis, acute or chronic myelogenous leukemia, pancreatic β cell destruction, osteoarthritis, rheumatoid spondylitis, gouty arthritis, inflammatory bowel disease, adult respiratory distress syndrome (ARDS), psoriasis, Crohn's disease, allergic rhinitis, ulcerative colitis, anaphylaxis, contact dermatitis, asthma, muscle degeneration, cachexia, Reiter's syndrome, type I diabetes, type II diabetes, bone resorption diseases, graft vs. host reaction, Alzheimer's disease, stroke, myocardial infarction, ischemia reperfusion injury, atherosclerosis, brain trauma, multiple sclerosis, cerebral malaria, sepsis, septic shock, toxic shock syndrome, fever, myalgias due to HIV-1, HIV-2, HIV-3, cytomegalovirus (CMV), influenza, adenovirus, the herpes viruses or herpes zoster infection in a mammal comprising administering an effective amount of a compound according to any one of the above embodiments.

Another aspect of the invention relates to a method of lowering plasma concentrations of either or both TNF-a and IL-1 comprising administering an effective amount of a compound according to any one of the above embodiments.

Another aspect of the invention relates to a method of lowering plasma concentrations of either or both IL-6 and IL-8 comprising administering an effective amount of a compound according to any one of the above embodiments.

Another aspect of the invention relates to a method of prophylaxis or treatment of diabetes disease in a mammal comprising administering an effective amount of a compound according to any one of the above embodiments to produce a glucagon antagonist effect.

Another aspect of the invention relates to a method of prophylaxis or treatment of a pain disorder in a mammal comprising administering an effective amount of a compound according to any one of the above embodiments.

Another aspect of the invention relates to a method of decreasing prostaglandins production in a mammal comprising administering an effective amount of a compound according to any one of the above embodiments.

Another aspect of the invention relates to a method of decreasing cyclooxygenase enzyme activity in a mammal comprising administering an effective amount of a compound according to any one of the above embodiments. In another embodiment, the cyclooxygenase enzyme is COX-2.

Another aspect of the invention relates to a method of decreasing cyclooxygenase enzyme activity in a mammal comprising administering an effective amount of the above pharmaceutical composition. In another embodiment the cyclooxygenase enzyme is COX-2.

Another aspect of the invention relates to the manufacture of a medicament comprising a compound according to any one of the above embodiments.

Another aspect of the invention relates to the manufacture of a medicament for the treatment of inflammation comprising administering an effective amount of a compound according to any one of the above embodiments.

Another aspect of the invention relates to the manufacture of a medicament for the treatment of rheumatoid arthritis, Pagets disease, osteoporosis, multiple myeloma, uveititis, acute or chronic myelogenous leukemia, pancreatic β cell destruction, osteoarthritis, rheumatoid spondylitis, gouty arthritis, inflammatory bowel disease, adult respiratory distress syndrome (ARDS), psoriasis, Crohn's disease, allergic rhinitis, ulcerative colitis, anaphylaxis, contact dermatitis, asthma, muscle degeneration, cachexia, Reiter's syndrome, type I diabetes, type II diabetes, bone resorption diseases, graft vs. host reaction, Alzheimer's disease, stroke, myocardial infarction, ischemia reperfusion injury, atherosclerosis, brain trauma, multiple sclerosis, cerebral malaria, sepsis, septic shock, toxic shock syndrome, fever, myalgias due to HIV-1, HIV-2, HIV-3, cytomegalovirus (CMV), influenza, adenovirus, the herpes viruses or herpes zoster infection in a mammal comprising administering an effective amount of a compound according to any one of the above embodiments.

Another aspect of the invention involves a method of making a compound according to the above embodiments, comprising the steps of reacting $R^1$–$R^2$, wherein $R^1$ contains a secondary ring nitrogen, with

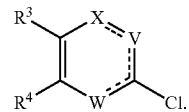

The compounds of this invention may have in general several asymmetric centers and are typically depicted in the form of racemic mixtures. This invention is intended to encompass racemic mixtures, partially racemic mixtures and separate enantiomers and diasteromers.

The specification and claims contain listing of species using the language "selected from . . . and . . . " and "is . . . or . . . " (sometimes referred to as Markush groups). When this language is used in this application, unless otherwise stated it is meant to include the group as a whole, or any single members thereof, or any subgroups thereof. The use of this language is merely for shorthand purposes and is not meant in any way to limit the removal of individual elements or subgroups as needed.

Unless otherwise specified, the following definitions apply to terms found in the specification and claims:

"Aryl" means a phenyl or naphthyl radical, wherein the phenyl may be fused with a $C_{3-4}$cycloalkyl bridge.

"Benzo group", alone or in combination, means the divalent radical $C_4H_4$=, one representation of which is —CH=CH—CH=CH—, that when vicinally attached to another ring forms a benzene-like ring—for example tetrahydronaphthylene, indole and the like.

"$C_{\alpha-\beta}$alkyl" means an alkyl group comprising from α to β carbon atoms in a branched, cyclical or linear relationship or any combination of the three. The alkyl groups described in this section may also contain double or triple bonds. Examples of $C_{1-8}$alkyl include, but are not limited to the following:

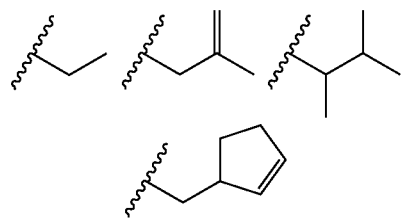

"Halogen" and "halo"mean a halogen atoms selected from F, Cl, Br and I.

"$C_{\alpha-\beta}$haloalkyl" means an alkyl group, as described above, wherein any number—at least one—of the hydrogen atoms attached to the alkyl chain are replaced by F, Cl, Br or I.

"Heterocycle" means a ring comprising at least one carbon atom and at least one other atom selected from N, O and S. Examples of heterocycles that may be found in the claims include, but are not limited to, the following:

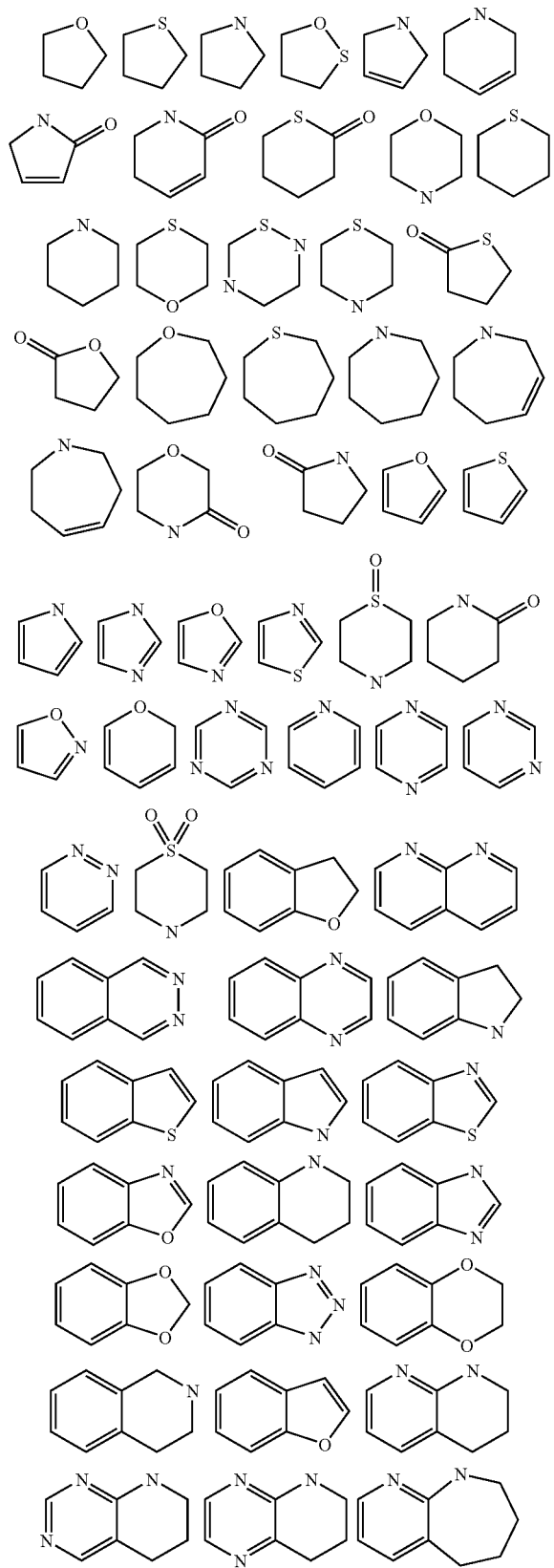

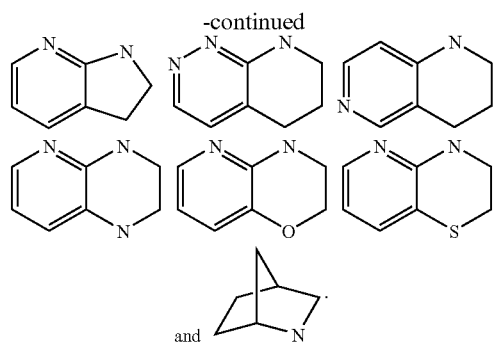

"Pharmaceutically-acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulfuric acid, phosphoric acid, methanesulphonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts", see infra and Berge et al., J. Pharm. Sci. 66:1 (1977).

"Leaving group" generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkylenylalkyl radicals, preferably have 6–10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, tri-fluoroacetyl, tri-chloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluenesulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl.

Silyl protecting groups are silicon atoms optionally substituted by one or more alkyl, aryl and aralkyl groups.

methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydroylsis and hydrogenolysis conditions well known to those skilled in the art.

It should be noted that compounds of the invention may contain groups that may exist in tautomeric forms, such as cyclic and acyclic amidine and guanidine groups, heteroatom substituted heteroaryl groups (Y'=O, S, NR), and the like, which are illustrated in the following examples:

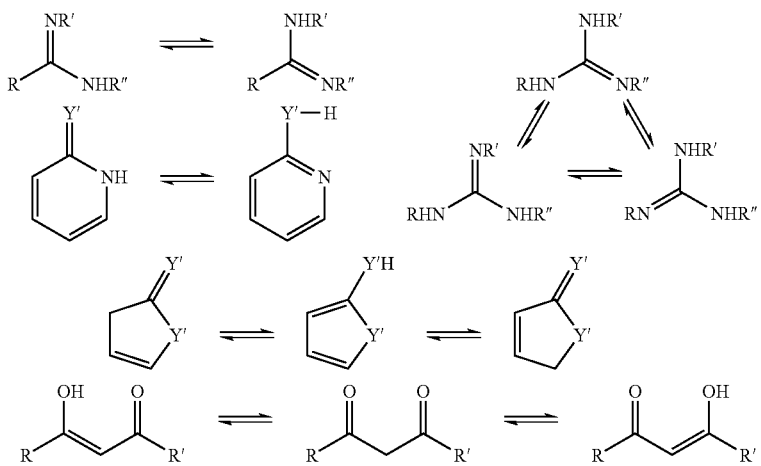

Suitable silyl protecting groups include, but are not limited to, trimethylsilyl, triethylsilyl, tri-isopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-tri-silyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-butyl-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These and though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bundgaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

"Cytokine" means a secreted protein that affects the functions of other cells, particularly as it relates to the modulation of interactions between cells of the immune system or cells involved in the inflammatory response. Examples of cytokines include but are not limited to interleukin 1 (IL-1), preferably IL-1β, interleukin 6 (IL-6), interleukin 8 (IL-8) and TNF, preferably TNF-α (tumor necrosis factor-α).

"TNF, IL-1, IL-6, and/or IL-8 mediated disease or disease state" means all disease states wherein TNF, IL-1, IL-6, and/or IL-8 plays a role, either directly as TNF, IL-1, IL-6, and/or IL-8 itself, or by TNF, IL-1, IL-6, and/or IL-8 inducing another cytokine to be released. For example, a disease state in which IL-1 plays a major role, but in which the production of or action of IL-1 is a result of TNF, would be considered mediated by TNF.

Compounds according to the invention can be synthesized according to one or more of the following methods. It should be noted that the general procedures are shown as it relates to preparation of compounds having unspecified stereochemistry. However, such procedures are generally applicable to those compounds of a specific stereochemistry, e.g., where the stereochemistry about a group is (S) or (R). In addition, the compounds having one stereochemistry (e.g., (R)) can often be utilized to produce those having opposite stereochemistry (i.e., (S)) using well-known methods, for example, by inversion.

4(3H)-Pyrimidinones:

For the synthesis of 4(3H)-pyrimidinones II (or its tautomer, 4-hydroxy-pyrimidines), the approach displayed in Scheme 1 may be followed (for a review of synthetic methods see: D. J. Brown, Heterocyclic Compounds: the Pyrimidines, supra). This approach involves the cyclization reaction between an acrylic acid ester XII and an amidine V followed by oxidation of the resulting dihydropyrimidinone XIII to give II.

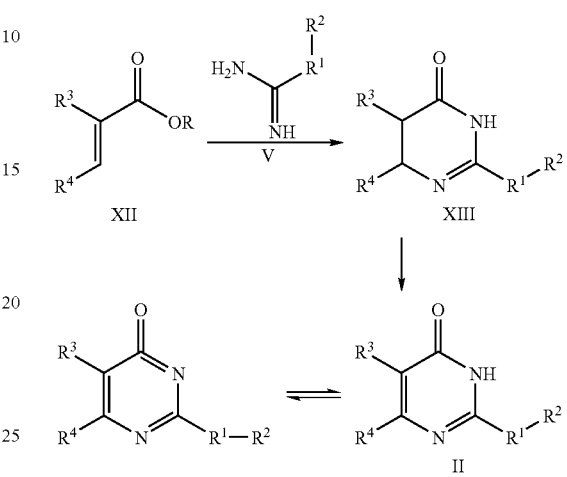

Scheme 1

For the synthesis of 2-substituted 5-(4-fluorophenyl)-6-(4-pyridyl)-4-hydroxy-pyrimidines II (Scheme 2), the disubstituted acrylic acid ester XII may be prepared conveniently by condensation of pyridine-4-carboxaldehyde with 4-fluorophenylacetic acid followed by esterification. XII may be reacted with a variety of amidines V at elevated temperature. As a dehydrogenating agent for the conversion of XIII to II, sodium nitrite/acetic acid is suitable.

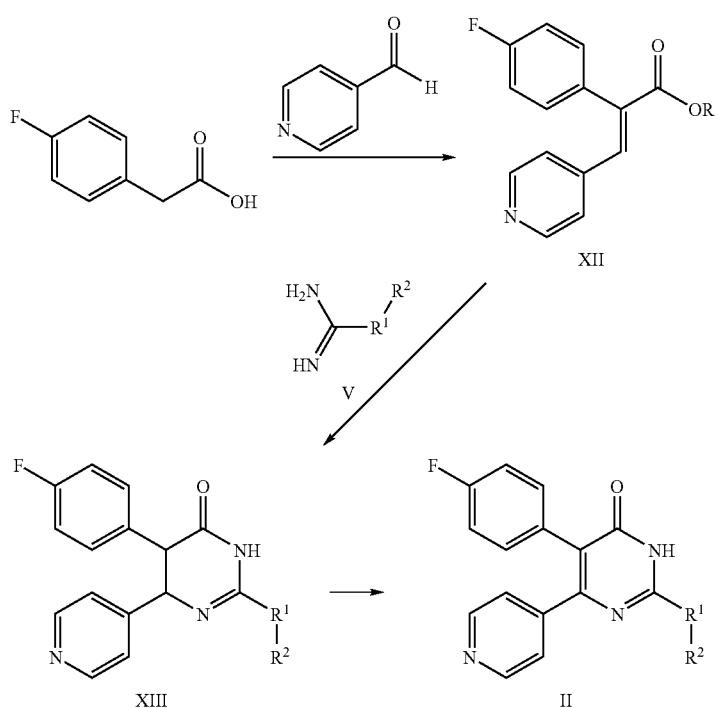

Scheme 2

Accordingly, further compounds of formula II may be obtained in which R⁴ is any other heteroaryl ring within the definition of R⁴ by the appropriate choice of starting material. Such starting materials include but are not limited to 2-methylpyridine-4-carboxaldehyde, 2,6-dimethylpyridine-4-carboxaldehyde (Mathes and Sauermilch, *Chem. Ber.* 88, 1276–1283 (1955)), quinoline-4-carboxaldehyde, pyrimidine-4-carboxaldehyde, 6-methylpyrimidine-4-carboxaldehyde, 2-methylpyrimidine-4-carboxaldehyde, 2,6-dimethylpyrimidine-4-carboxalde-hyde (Bredereck et al., *Chem. Ber.* 97, 3407–3417 (1964)). The use of 2-nitropyridine-4-carboxaldehyde would lead to a derivative of formula II with R⁴ represented by a 2-nitro-4-pyridyl group. Catalytic reduction of the nitro to an amino group would provide the 2-amino-4-pyridyl derivative of II. The approach displayed in Scheme 2 is applicable to the use of other aryl acetic acids leading to compounds of formula H with different aryl groups as $R^3$.

Pyrimidinone II ($R^1$=H) may be substituted at the N-3 position by reaction with e.g. an alkyl halide, such as methyl iodide or ethyl bromide in the presence of an appropriate base such as potassium carbonate and the like.

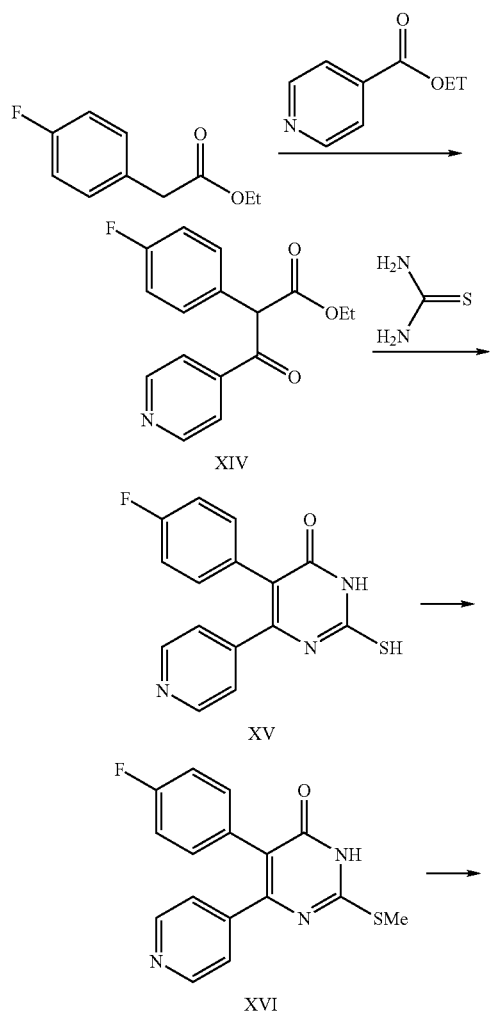

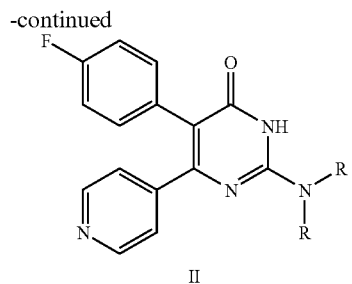

Another approach (Scheme 3) leading to 5,6-diaryl-4-hydroxy-pyrimidines involves the cyclization of the b-keto ester XIV with thiourea to give the thiouracil derivative XV. XV can be S-monomethylated to XVI. Reaction of XVI with primary and secondary amines gives 2-amino substituted 4-hydroxypyrimidines II.

Although Scheme 3 illustrates syntheses in which R⁴ is 4-pyridyl, this approach may be equally applied to any other heteroaryl ring within the definition of R⁴ by the appropriate choice of the starting material. Such starting materials include but are not limited to ethyl 2-methyl isonicotinate (Efimovsky and Rumpf, *Bull. Soc. Chim. FR.* 648–649 (1954)), methylpyrimidine-4-carboxylate, methyl 2-methylpyrimidine-4-carboxylate, methyl 6-methylpyrimidine-4-carboxylate and methyl 2,6-dimethylpyrimidine-4-carboxylate (Sakasi et al., *Heterocycles* 13, 235 (1978)). Likewise, methyl 2-nitroisonicotinate (Stanonis, *J. Org. Chem.* 22, 475 (1957)) may be reacted with an aryl acetic acid ester followed by cyclization of the resultant β-keto ester with thiourea analogously to Scheme 3. Subsequent catalytic reduction of the nitro group to an amino group would give a pyrimidinone $R^i$ in which R⁴ is represented by a 2-amino-4-pyridyl group (Scheme 4).

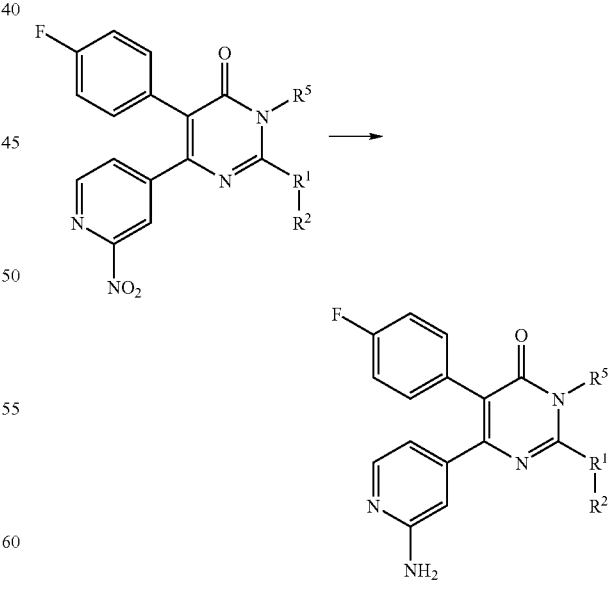

Furthermore, methyl 2-acetamido isonicotinate (Scheme 5) may be reacted analogously to Scheme 3 after appropriate protection of the amide nitrogen with e.g. a tert-butyldimethylsilyloxymethyl group (Benneche et al., *Acta Chem. Scand. B* 42 384–389 (1988)), a tert-butyldimethylsilyl group, a benzyloxymethyl group, a benzyl group or the like (P1).

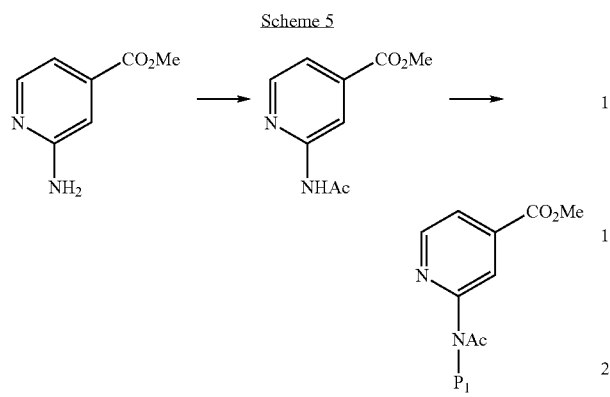

Scheme 5

Removal of the protecting group $P_1$ of the resulting pyrimidine II with a suitable reagent (e.g., tetrabutylammonium fluoride in the case where $P_1$ is t-butyldimethylsilyloxymethyl) would then lead to a pyrimidinone II with $R^4$ represented by a 2-acetamido-4-pyridyl group. Needless to say, ethyl p-fluorophenyl acetate may be substituted by any alkyl arylacetate in the procedure illustrated in Scheme 3 thus providing compounds of formula II with different $R^3$ aryl substituents.

In a further process, pyrimidinones II may be prepared by coupling a suitable derivative of XVIII (L is a leaving group, such as halogen radical and the like) with an appropriate aryl equivalent.

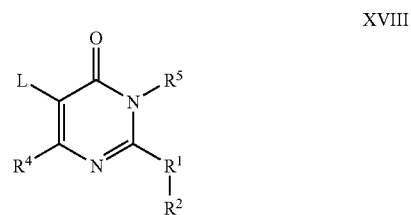

XVIII

Such aryl/heteroaryl couplings are well known to those skilled in the art and involve an organic-metallic component for reaction with a reactive derivative, e.g., a halogeno derivative, of the second compound in the presence of a catalyst. The metallo-organic species may be provided either by the pyrimidinone in which case the aryl component provides the reactive halogen equivalent or the pyrimidinone may be in the form of a reactive 5-halogeno derivative for reaction with a metallo organic aryl compound. Accordingly, 5-bromo and 5-iodo derivatives of XVIII (L=Br, I) may be treated with arylalkyl tin compounds, e.g., trimethylstannylbenzene, in an inert solvent such as tetrahydrofuran in the presence of a palladium catalyst, such as di(triphenylphosphine)palladium(II)dichloride. (Peters et al., *J. Heterocyclic Chem.* 27, 2165–2173, (1990). Alternatively, the halogen derivative of XVIII may be converted into a trialkyltin derivative (L=Bu$_3$Sn) by reaction with e.g. tributylstannyl chloride following lithiation with butyllithium and may then be reacted with an aryl halide in the presence of a catalyst. (Sandosham and Undheim, *Acta Chem. Scand.* 43, 684–689 (1989). Both approaches would lead to pyrimidines II in which $R^{11}$ is represented by aryl and heteroaryl groups.

As reported in the literature (Kabbe, *Lieb. Ann. Chem.* 704, 144 (1967); German Patent 1271116 (1968)) and displayed in Scheme 6,5-aryl-2,6-dipyridyl-4(3H)-pyrimidinones II may be prepared in a one step synthesis by reaction of the cyanopyridine with an arylacetyl ester, such as ethyl phenylacetate in the presence of sodium methoxide.

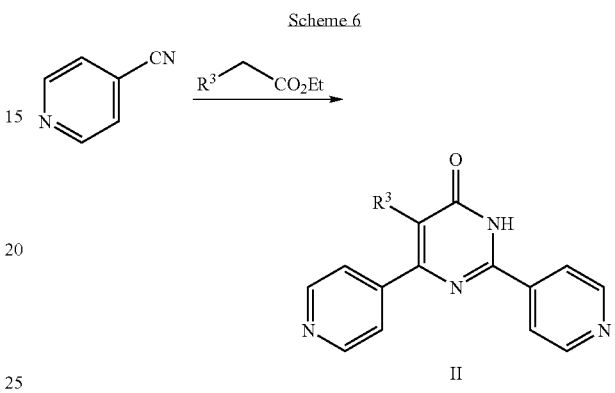

Scheme 6

II

In Scheme 7, compounds of the present invention of formula XXX can be readily prepared by reacting the methylthio intermediate XXXI with the amine NHRR, for example by heating the mixture preferably at a temperature greater than 100° C., more preferably 150–210° C. Alternatively, compounds of formula XXX can be readily prepared by reacting the methylsulfonyl intermediate XXXII with the amine NHRR, for example by heating the mixture preferably at a temperature greater than 40° C., more preferably 50–210° C.

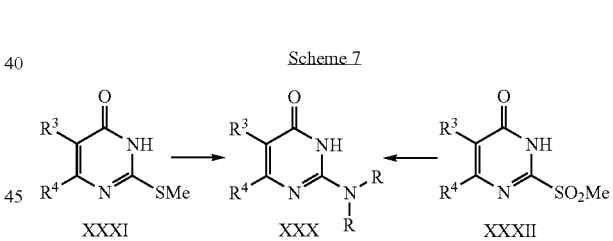

Scheme 7

XXXI    XXX    XXXII

Amines of formula NHRR are commercially available or can be readily prepared by those skilled in the art from commercially available starting materials. For example, an amide, nitro or cyano group can be reduced under reducing conditions, such as in the presence of a reducing agent like lithium aluminum hydride and the like, to form the corresponding amine. Alkylation and acylation of amino groups are well known in the art. Chiral and achiral substituted amines can be prepared from chiral amino acids and amino acid amides (for example, alkyl, aryl, heteroaryl, cycloalkyl, arylalkyl, heteroarylalkyl, cycloalkylalkyl and the like substituted glycine, β-alanine and the like) using methods well known in the art, such as H. Brunner, P. Hankofer, U. Holzinger, B. Treittinger and H. Schoenenberger, *Eur. J. Med. Chem.* 25, 35–44, 1990; M. Freiberger and R. B. Hasbrouck, *J. Am. Chem. Soc.* 82, 696–698, 1960; Dornow and Fust, *Chem. Ber.* 87, 984, 1954; M. Kojima and J. Fujita, *Bull. Chem. Soc. Jpn.* 55, 1454–1459, 1982; W. Wheeler and D. O'Bannon, *Journal of Labeled Compounds and Radiop-* harmaceuticals XXXI, 306, 1992; and S. Davies, N. Garrido, O. Ichihara and I. Walters, J. Chem. Soc., Chem. Commun. 1153, 1993.

Pyridones:

As displayed in Scheme 8, a suitable route to 2(1H)-pyridones III involves the cyclization reaction between an α,β-unsaturated ketone XXII and a sufficiently reactive, substituted acetamide in the presence of base (Ell-Rayyes and Al-Hajjar, *J. Heterocycl. Chem.* 21, 1473 (1984)) and subsequent dehydrogenation.

cycloalkyl derivatives in the presence of piperidine/acetic acid at elevated temperature (Bayer and Hartmann, *Arch. Pharm.* (Weinheim) 324, 815 (1991)) as well as pinacolone ($CH_3$—CO—$C(CH_3)_3$) in the presence of sodium hydroxide to provide the unsaturated ketone XXII (or the analogous ketone from the corresponding heteroaromatic-4-carboxyaldehyde). The reaction of XXII with phenylacetamide in the presence of sodium ethoxide then may lead via the 3,4-dihydropyridone to 6-substituted 3-phenyl-4-(heteroaryl)-2(1H)-pyridones of structure III.

In Scheme 10, a feasible route is illustrated leading to 6-chloro-2(1H)-pyridone XXIV, a versatile intermediate for further modifications at the 6-position. This approach (G. Simchen, Chem. Ber. 103, 389–397 (1970)) is based on the conversion of the unsaturated g-cyanocarboxylic acid chloride XXIII into XXIV in the presence of hydrogen chloride.

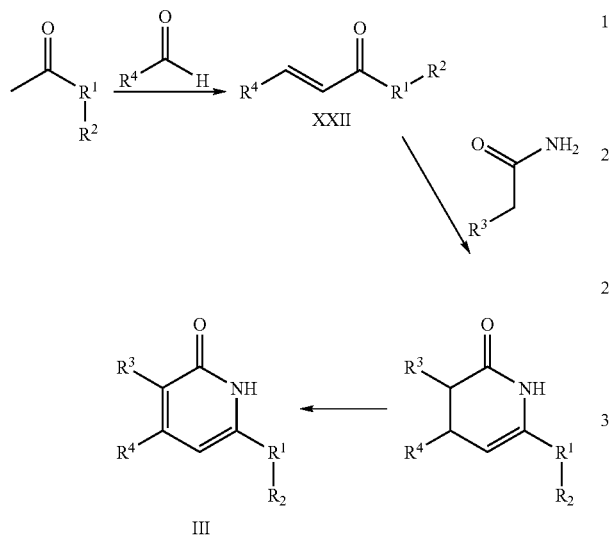

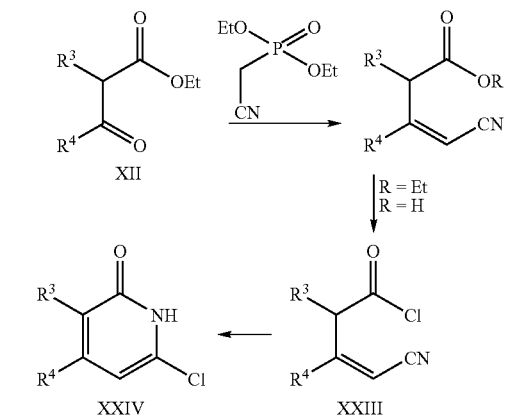

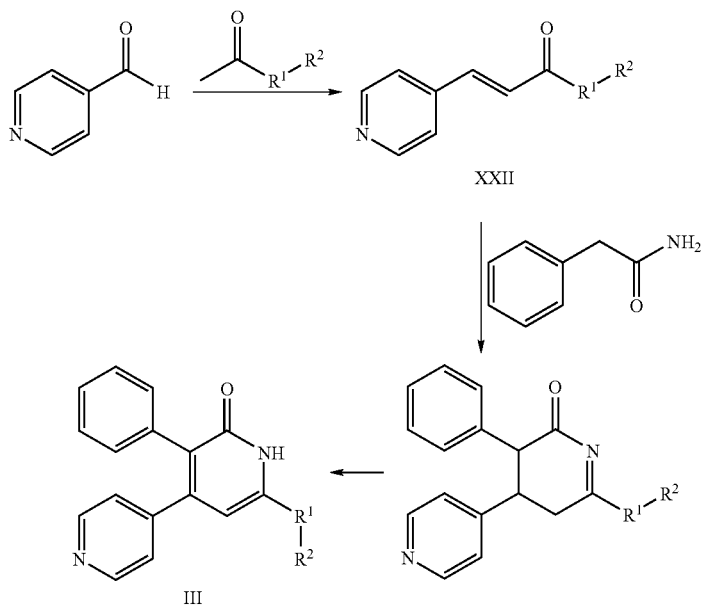

Accordingly (Scheme 9), pyridine-4-carboxaldehyde or other heteroaromatic carboxaldehyde-like pyrimidine-4-carboxaldehydes or quinoline-4-carboxyaldehydes may be reacted with acetyl aryl, acetyl heteroaryl or acetyl Reaction of XXIV with ammonia (Katritzky and Rachwal, *J. Heterocylic Chem.* 32, 1007 (1995)), primary and secondary amines would lead to 2-amino substituted pyridones III.

In addition, pyridone III may be substituted at the N–1 position by reaction with, e.g., an alkyl halide in the presence of an appropriate base such as potassium carbonate.

An approach that may lead to a pyrimidinone of the general formula III is illustrated in Scheme 11.

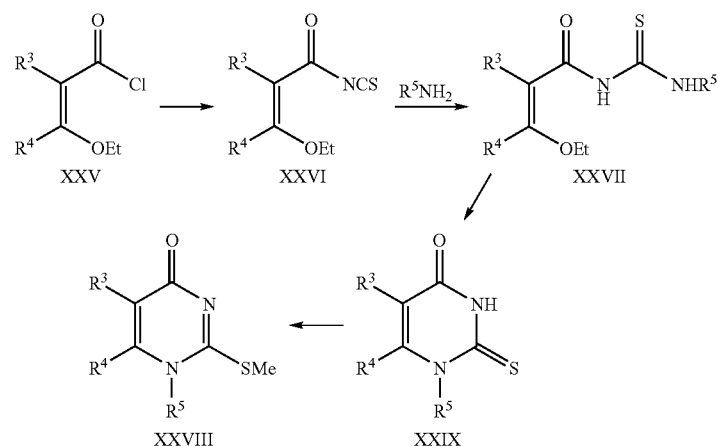

Scheme 11

According to this approach (Shaw and Warrener, *J. Chem. Soc.* 153–156 (1958); Hronowski and Szarek, *Can. J. Chem.* 63, 2787 (1985); Agathocleous and Shaw, *J. Chem. Soc. Perkin Trans. I*, 2555 (1993)), an ethoxyacryloyl isothiocyanate XXVI is reacted with a primary amine to give as an addition product the acylthiourea XXVII which can be cyclized under basic or acidic conditions to the thiouracil compound XXVIII. XXVIII may be methylated to the methylthio derivative XXIX, a versatile intermediate for further transformations at the 2-position.

The following Examples are presented for illustrative purposes only and are not intended, nor should they be construed, as limiting the invention in any manner. Those skilled in the art will appreciate that modifications and variations of the compounds disclosed herein can be without violating the spirit or scope of the present invention.

EXAMPLES

Example 1

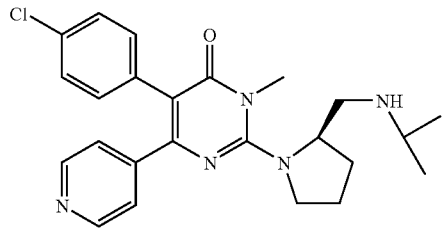

5-(4-Chloro-phenyl)-2-[2-(R)-isopropylamino-methyl)-pyrrolidin-1-yl]-3-methyl-6-pyridin-4-yl-3H-pyrimidin-4-one Step A: 2-((R)-Isopropylamino-methyl)-pyrrolidine-1-carboxylic acid tert-butyl ester To a solution of 2-(R)-Aminomethyl-pyrrolidine-1-carboxylic acid tert-butyl ester 7.72 g in chloroform was added acetone 22.40 g followed by sodium triacetoxyboron hydride 24.54 g. The reaction mixture was heated to 70° C. for 3.5 hours and cooled down to room temperature. Work up to give desired product as light yellow oil. MS (ES+): 243 (M+H)$^+$.

Step B: (R)-Isopropyl-pyrrolidin-2-ylmethyl-amine

To a solution of 2-((R)-Isopropylamino-methyl)-pyrrolidine-1-carboxylic acid tert-butyl ester 9.12 g in methanol was added excessive of HCl in dioxane. The solvent was removed after 30 minutes under reduced pressure to give the desired product as off-white solid. MS (ES+): 143 (M+H)$^+$.

Step C: 5-(4-Chloro-phenyl)-2-[2-(R)-isopropylamino-methyl)-pyrrolidin-1-yl]-3-methyl-6-pyridin-4-yl-3H-pyrimidin-4-one To a solution of (R)-Isopropyl-pyrrolidin-2-ylmethyl-amine 0.46 g was added potassium carbonate 1.00 g followed by 2-Chloro-5-(4-chloro-phenyl)-3-methyl-6-pyridin-4-yl-3H-pyrimidin-4-one 1.07 g at room temperature. After 12 hours, work up between chloroform and water followed by HPLC purification afforded the title compound as yellow solid. MS (ES+): 438 (M+H)$^+$; (ES–): 436 (M–H)$^-$.

Example 2

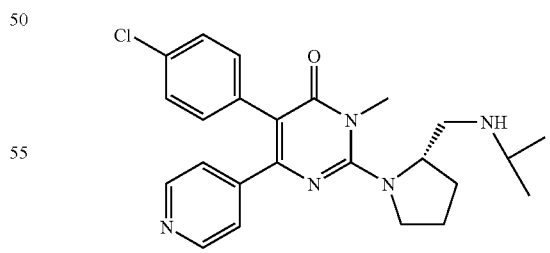

5-(4-Chloro-phenyl)-2-[2-(S)-isopropylamino-methyl)-pyrrolidin-1-yl]-3-methyl-6-pyridin-4-yl-3H-pyrimidin-4-one The title compound was analogously synthesized by the method described in Example 1 from 2-(S)-Aminomethylpyrrolidine-1-carboxylic acid tert-butyl ester. This compound was obtained as yellow solid. MS (ES+): 438 (M+H)⁺; (ES−): 436 (M−H)⁻.

Example 3

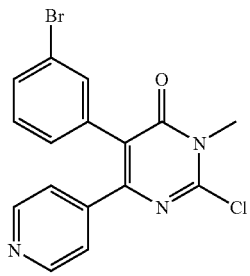

5-(3-Bromo-phenyl)-2-chloro-3-methyl-6-pyridin-4-yl-3H-pyrimidin-4-one

Step A: To a 500 mL round bottom flask (RBF), was added ethyl (3-bromo-phenyl)acetate (10.3 g, 42.2 mmol), 4-cyanopyridine (4.4 g, 42.2 mmol) and 56 mL DMF. The mixture was stirred at room temperature under nitrogen. 42 mL 1 M KOtBu in tBuOH was added drop wise, and stirred for 1 h at rt. Methyl isothiocyanate (3.08 g, 42.2 mmol) was added in one portion, and stirred for another one hour at rt. The mixture was cooled down to 0° C., iodomethane (2.7 mL, 42.2 mmol) was added drop wise and stirred for 1 h at 0° C. To quench the reaction, 100 mL H$_2$O was added. Yellow solid was precipitated. After filtration and washed with H$_2$O, the 5-(3-bromo-phenyl)-3-methyl-2-methylsulfanyl-6-pyridin-4-yl-3H-pyrimidin-4-one was obtained in 9.2 g as pale yellow powder. MS (ES+): 388 (M+H)⁺; (ES−): 386 (M−H).

Step B: To a 250 mL RBF, was added 5-(3-bromophenyl)-3-methyl-2-methylsulfanyl-6-pyridin-4-yl-3H-pyrimidin-4-one (9.2 g, 23.7 mmol), 28 mL dioxane, and 24 mL 5 N NaOH in H$_2$O. The mixture was warmed up to 85° C. and stirred for 15 h. The mixture was cooled down to 0° C. and neutralized with 1 N HCl in H$_2$O until pH 5. White solid was precipitated. After filtration and washed with water, the 5-(3-bromo-phenyl)-2-hydroxy-3-methyl-6-pyridin-4-yl-3H-pyrimidin-4-one was obtained in 5.76 g as white powder. MS (ES+): 358 (M+H)⁺; (ES−): 356 (M−H).

Step C: To a 250 mL RBF, was added 5-(3-bromophenyl)-2-hydroxy-3-methyl-6-pyridin-4-yl-3H-pyrimidin-4-one (5.76 g, 16.1 mmol), 50 mL POCl$_3$. The mixture was warmed up to 85° C. and stirred for 15 h under nitrogen. The mixture was cooled down to rt and vacuumed down all volatile composites. The black cake obtained was dissolved in dichloromethane, neutralized with sat. NaHCO$_3$. After purified by flash chromatography, the 5-(3-Bromo-phenyl)-2-chloro-3-methyl-6-pyridin-4-yl-3H-pyrimidin-4-one was obtained in 4.72 g as white powder. MS (ES+): 376 (M+H)⁺; (ES−): 374 (M−H).

Example 4

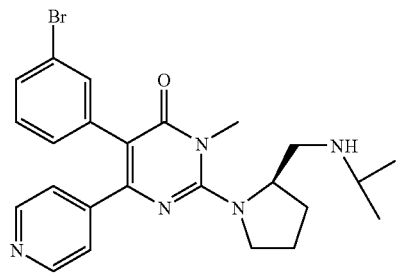

5-(3-Bromo-phenyl)-2-[2-(isopropylamino-methyl)-pyrrolidin-1-yl]-3-methyl-6-pyridin-4-yl-3H-pyrimidin-4-one To a 100 mL RBF, was added (R)-isopropyl-pyrrolidin-2-ylmethyl-amine (0.78 g, 3.6 mmol), and 50 mL dichloromethane at 0° C. under nitrogen. 2.1 mL diisopropylethylamine (12 mmol) was added drop wise, and stirred for 10 min. 5-(3-Bromo-phenyl)-2-chloro-3-methyl-6-pyridin-4-yl-3H-pyrimidin-4-one (1.13 g, 3 mmol) was added in one portion. The mixture was stirred at 0° C. to rt for 12 h. The mixture was diluted with 100 mL dichloromethane, washed with sat. NaHCO$_3$ and brine. After purified by flash chromatography, the title compound was yielded in 1.3 g as pale yellow solid. MS (ES+): 482 (M+H)⁺.

Example 5

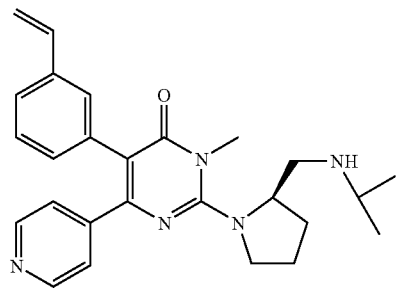

2-[2-(Isopropylamino-methyl)-pyrrolidin-1-yl]-3-methyl-6-pyridin-4-yl-5-(3-vinyl-phenyl)-3H-pyrimidin-4-one To a 250 mL RBF, was added 5-(3-bromo-phenyl)-2-[2-(isopropylamino-methyl)-pyrrolidin-1-yl]-3-methyl-6-pyridin-4-yl-3H-pyrimidin-4-one (0.48 g, 1.0 mmol), 50 mL xylene, 5 mL DMF and 0.58 mL tributyl(vinyl)tin. The mixture was degassed by nitrogen bubbled through for 1 h. After added Pd(PPh$_3$)$_4$ (58 mg, 0.05 mmol), the mixture was warmed up to 140° C. and stirred for 1 h under nitrogen. The mixture was cooled down to rt, 20 mL 10% KF solution was added and stirred for 30 min. The mixture was diluted with 200 mL dichloromethane, washed with sat. NaHCO$_3$ and brine. After purified by flash chromatography, the title compound was obtained in 0.28 g as pale yellow solid. MS (ES+): 430 (M+H)+; (ES−): 428 (M−H).

Example 6

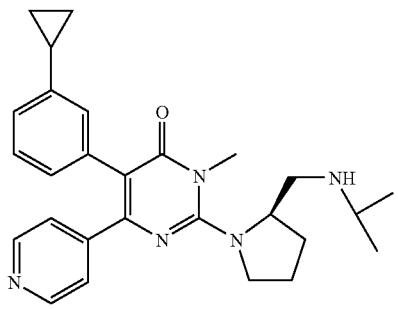

5-(3-Cyclopropyl-phenyl)-2-[2-(isopropylamino-methyl)-pyrrolidin-1-yl]-3-methyl-6-pyridin-4-yl-3H-pyrimidin-4-one To a 100 mL RBF, was added 5-(3-bromo-phenyl)-2-[2-(isopropylamino-methyl)-pyrrolidin-1-yl]-3-methyl-6-pyridin-4-yl-3H-pyrimidin-4-one (0.4 g, 0.82 mmol), 30 mL toluene, and cyclopropyl boronic cid (86 mg, 1.0 mmol). The mixture was degassed by nitrogen bubbled through for 1 h. After added Pd(PPh)$_4$ (30 mg, 0.025 mmol) and NaOtBu (0.24 g, 2.5 mmol), the mixture was warmed up to 100° C. and stirred for 1 h under nitrogen. The mixture was cooled down to rt, and vacuumed down all volatile composites. After purified by flash chromatography, the title compound was obtained in 0.1 g as pale yellow solid. MS (ES+): 444 (M+H)+; (ES−): 4442 (M−H).

Example 7

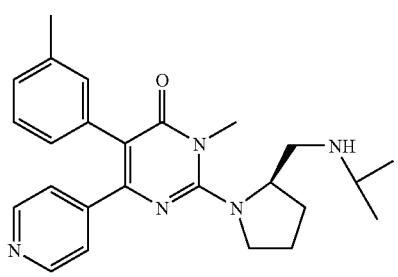

2-[2-(Isopropylamino-methyl)-pyrrolidin-1-yl]-3-methyl-6-pyridin-4-yl-5-m-tolyl-3H-pyrimidin-4-one To a 100 mL RBF, was added (R)-isopropyl-pyrrolidin-2-ylmethyl-amine (0.13 g, 0.6 mmol), and 50 mL dichloromethane at 0° C. under nitrogen. 0.28 mL diisopropylethylamine (1.6 mmol) was added drop wise, and stirred for 10 min. 2-Chloro-3-methyl-6-pyridin-4-yl-5-m-tolyl-3H-pyrimidin-4-one (0.16 g, 0.5 mmol) was added in one portion, and stirred at 0° C. to rt for 12 h. (This meta-methyl chloro-intermediate was synthesized by a similar procedure as that of 5-(3-Bromo-phenyl)-2-chloro-3-methyl-6-pyridin-4-yl-3H-pyrimidin-4-one.) The mixture was diluted with 100 mL dichloromethane, washed with sat. NaHCO$_3$ and brine. After purified by flash chromatography, the title compound was obtained in 0.219 g as pale yellow solid. MS (ES+): 418 (M+H)+.

Example 8

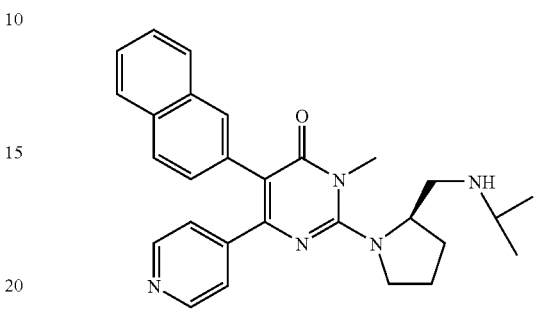

2-[2-(Isopropylamino-methyl)-pyrrolidin-1-yl]-3-methyl-5-naphthalen-2-yl-6-pyridin-4-yl-3H-pyrimidin-4-one To a 100 mL RBF, was added (R)-isopropyl-pyrrolidin-2-ylmethyl-amine (0.186 g, 0.86 mmol), and 50 mL dichloromethane at 0° C. under nitrogen. 0.3 mL diisopropylethylamine (1.71 mmol) was added drop wise, and stirred for 10 min. 2-Chloro-3-methyl-5-naphthalen-2-yl-6-pyridin-4-yl-3H-pyrimidin-4-one (0.2 g, 0.57 mmol) was added in one portion, and stirred at 0° C. to rt for 12 h. (This naphthyl chloro-intermediate was synthesized by a similar procedure as that of 5-(3-Bromo-phenyl)-2-chloro-3-methyl-6-pyridin-4-yl-3H-pyrimidin-4-one.) The mixture was diluted with 100 mL dichloromethane, washed with sat. NaHCO$_3$ and brine. After purified by flash chromatography, the title compound was obtained in 0.21 g as pale yellow solid. MS (ES+): 454 (M+H)+; (ES−): 452 (M−H).

Example 9

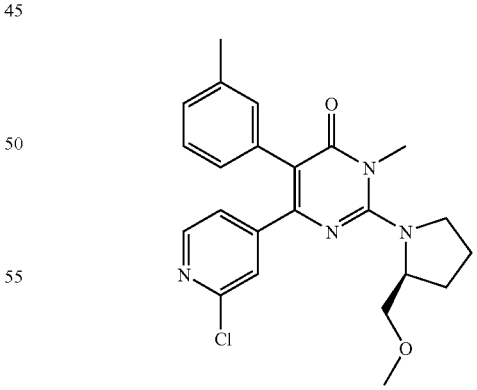

6-(2-Chloro-pyridin-4-yl)-2-(2-methoxymethyl-pyrrolidin-1-yl)-3-methyl-5-m-tolyl-3H-pyrimidin-4-one To a 100 mL RBF, was added (S)-2-methoxymethyl-pyrrolidine (0.172 g, 1.5 mmol), and 50 mL dichloromethane at 0° C. under nitrogen. 0.35 mL diisopropyl-ethylamine (2.0 mmol) was added drop wise, and stirred for 10 min. 2-Chloro- 6-(2-chloropyridin-4-yl)-3-methyl-5-m-tolyl-3H-pyrimidin-4-one (0.345 g, 1.0 mmol) was added in one portion, and stirred at 0° C. to rt for 12 h. The mixture was diluted with 100 mL dichloromethane, washed with sat. NaHCO₃ and brine. After purified by flash chromatography, the title compound was obtained in 0.40 g as pale yellow solid. MS (ES+): 425 (M+H)⁺.

Example 10

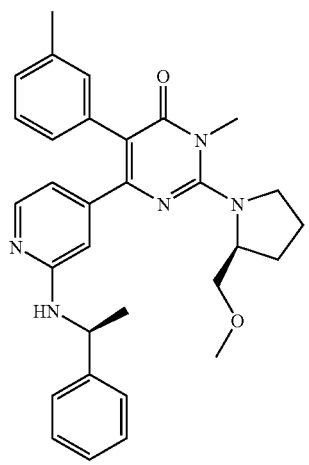

2-(2-Methoxymethyl-pyrrolidin-1-yl)-3-methyl-6-[2-(1-phenyl-ethylamino)-pyridin-4-yl]-5-m-tolyl-3H-pyrimidin-4-one To a 100 mL RBF, was added 6-(2-chloro-pyridin-4-yl)-2-(2-methoxymethyl-pyrrolidin-1-yl)-3-methyl-5-m-tolyl-3H-pyrimidin-4-one (0.3 g, 0.71 mmol), 50 mL toluene, and (S)-α-methyl benzylamine (0.181 mL, 1.42 mmol). The mixture was degassed by nitrogen bubbled through for 1 h. After added Pd(OAc)₂ (24 mg, 0.106 mmol), BINAP (65 mg, 0.106 mmol) and NaOtBu (0.191 g, 2.0 mmol), the mixture was warmed up to 100° C. and stirred for 3 h under nitrogen. The mixture was cooled down to rt, and vacuumed down all volatile composites. After purified by flash chromatography, the title compound was obtained in 0.18 g as pale yellow solid. MS (ES+): 510 (M+H)⁺.

Scheme 12

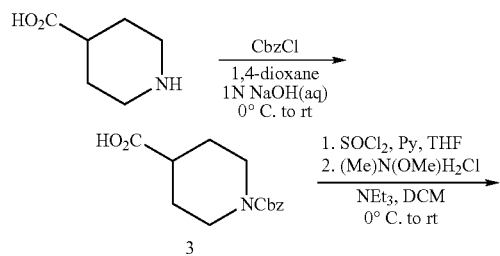

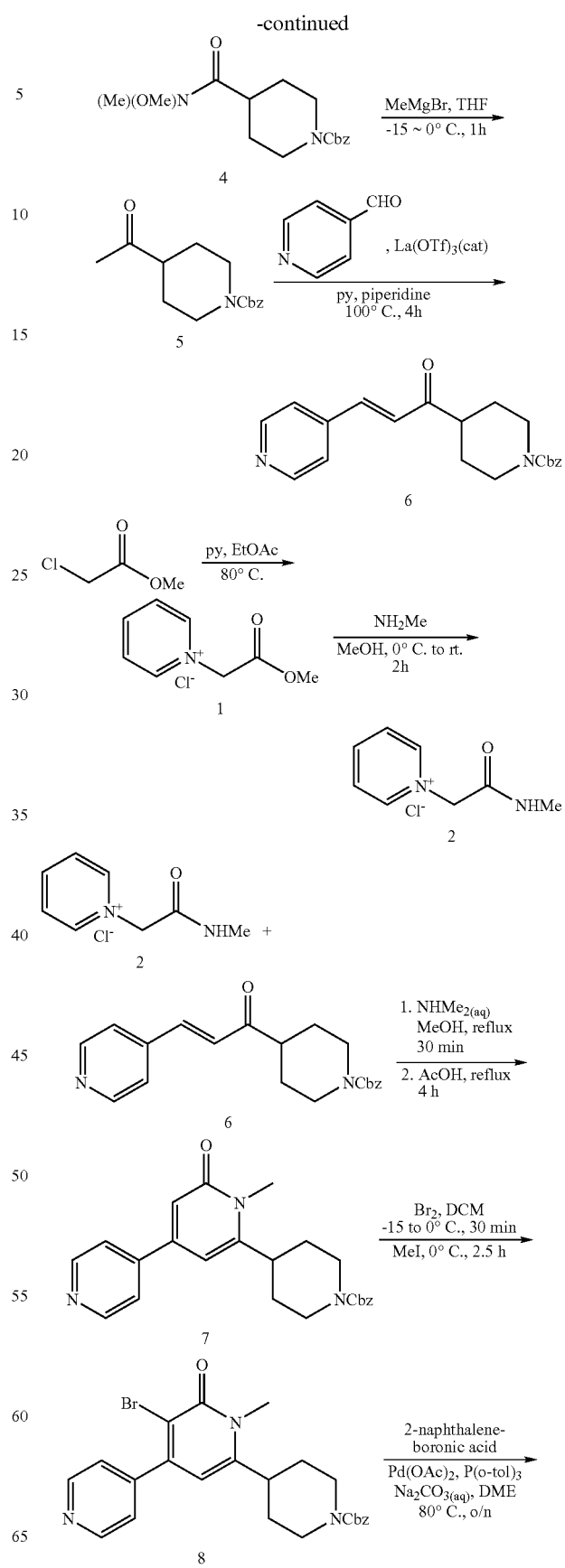

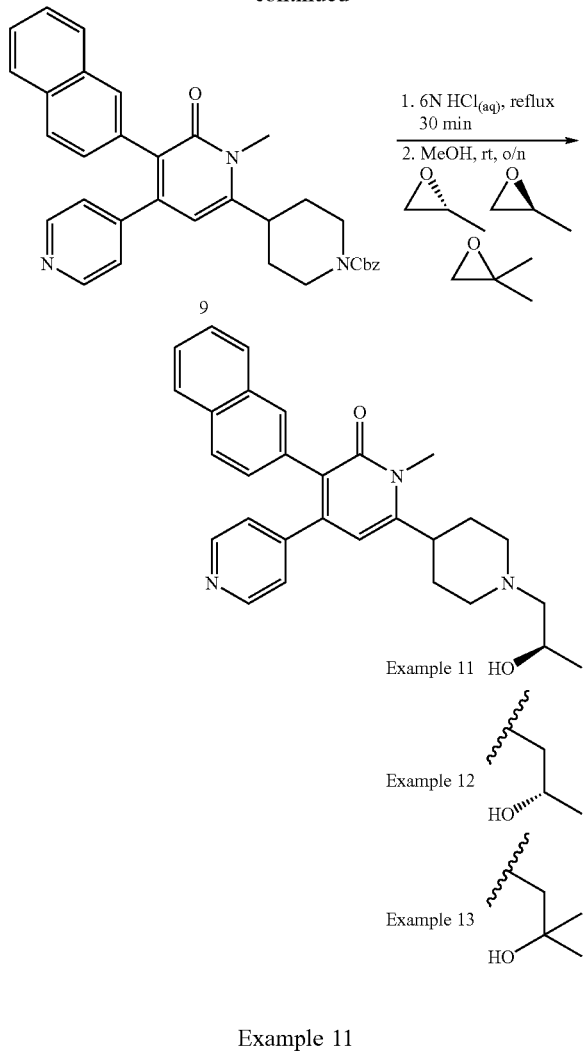

Example 11

1-(2R-Hydroxy-propyl)-1'-methyl-5'-naphthalen-2-yl-1,2,3,4,5,6-hexahydro-1'H-[4,2';4',4"]terpyridin-6'-one.

Step A: 1-Methoxycarbonylmethyl-pyridinium chloride. In a 250 mL round-bottom flask with a stir bar was charged 2-chloromethylacetate (17.5 mL, 0.2 mol), ethyl acetate (50 mL), and pyridine (16.2 mL, 0.2 mol). The overall homogeneous solution was heated with a condenser at 80° C. for 24 h and the resulting heterogeneous white suspension was cooled to room temperature and filtrated under reduced pressure. The off-white filtrate was recrystallized from small amount of ethanol to give the title compound (27.4 g, 73%) as a white solid. MS (ES+): 152 (M)+.

Step B: 1-Methylcarbamoylmethyl-pyridinium chloride. In a 250 mL round-bottom flask with a stir bar, salt 1 (25 g, 0.133 mol) was suspended in ethanol (150 mL) at 0° C. and methylamine was bubbled into the mixture via a needle until the overall mixture became homogeneous. The overall yellow solution was stirred at room temperature for additional 2 h and the resulting solution was concentrated to ~30 mL while a lot of salt 2 precipitate appeared. Filtration followed by washing the collected solid with minimal amount of ethanol provided salt 2 (21.6 g, 87%) as an essentially pure off-white crystalline. MS (ES+): 151 (M)+.

Step C: Piperidine-1,4-dicarboxylic acid monobenzyl ester. In a 1-L round-bottom flask with a stir bar and equipped with an additional funnel was charged isonipecotic acid (13 g, 0.1 mol) followed by 1,4-dioxane (50 mL). The resulting stirred white suspension was added 5N NaOH aqueous solution (30 mL, 0.15 mol) at room temperature and the overall almost homogeneous solution was cooled in an ice-water bath. CbzCl (19 mL, 0.13 mol) was dropped from an additional funnel slowly in 15 min and the overall heterogeneous mixture was stirred at room temperature for 3.5 h. The resulting mixture was diluted with water (20 mL) and ethyl acetate (100 mL) and the separated aqueous layer was extracted with ethyl acetate (50 mL×2). The combined organic layers were washed with brine, dried over MgSO$_4$, and concentrated to give the N-Cbz isonipecotic acid 3 as a colorless oil which was carried through to the next step without further purification. MS (ES+): 264 (M+H)+.

Step D: 4-(2-Methoxy-propionyl)-piperidine-1-carboxylic acid benzyl ester. To a cool (0° C.) stirred solution of crude acid 3 in anhydrous THF (100 mL) was added pyridine (10 mL) followed by slow addition of SOCl$_2$ via syringe under nitrogen. The resulting white suspension was stirred at the same temperature for 5 min prior to being warmed up room temperature and stirred for another 2 h. The resulting white heterogeneous mixture was concentrated under reduced pressure and the residue was dissolved in dichloromethane (200 mL). The crude acyl chloride solution was cooled in an ice-water bath and treated with triethylamine (28 mL, 0.2 mol) and Weinreb salt (10.7 g, 0.11 mol) subsequently. The overall yellow-orange mixture was naturally warmed up to room temperature and stirred overnight. The overall mixture was quenched with water (30 mL) and saturated NaHCO$_3$ (aq, 50 mL), and the separated aqueous layer was extracted with dichloromethane (200 mL×1), washed with brine, and dried (MgSO$_4$). The entire organic layers were concentrated to afford crude product which was purified with a flash column chromatography (ethyl acetate/hexanes, 1:2) to provide the desired amide 4 (27.8 g, 90% from isonipecotic acid) as a pale yellow oil. MS (ES+): 306 (M+H)+.

Step E: 4-Acetyl-piperidine-1-carboxylic acid benzyl ester. To a stirred solution of Weinreb amide 4 (27.83 g, 0.091 mol) in anhydrous THF (100 mL) was added slowly MeMgBr (84 mL, 1.4 M in THF/toluene) at −15° C. via an additional funnel in 30 min. The resulting heterogeneous mixture was stirred at the same temperature for another 30 min and quenched with 1N HCl and water (100 mL each)

subsequently at 0° C. The separated aqueous layer was extracted with ethyl acetate (100 mL×2) and the combined organic layers were washed with water, brine and dried over MgSO$_4$. Filtration and removal of the solvent yielded the acyl N-Cbz carbamate 5 (23.68 g, quant.) as a light yellow oil, which solidified upon standing and was carried out into the next reaction without any purifications. MS (ES+): 262 (M+H)$^+$.

Step F: 4-(3-Pyridin-4-yl-acryloyl)-piperidine-1-carboxylic acid benzyl ester. In a flame-dried three-neck 1 L round-bottomed flask containing a stir bar and 5 (30 g, 0.11 mol) was added pyridine (77 mL) via syringe under nitrogen at room temperature. To this stirred solution was added 4-pyridinecarbaldehyde (15.4 mL, 0.16 mol) and La(OTf)$_3$ (7.6 g, 10% eq) subsequently. Piperidine (11.6 mL, 0.117 mol) was then dropwise added via syringe and the resulting brown mixture was heated to 100° C. for 4 h. The resulting dark brown mixture was concentrated by removing all of the volatile material under a vacuum distillation conditions, and the residue was diluted with 500 mL ethyl acetate, washed with saturated aqueous NaHCO$_3$ and brine, and finally dried over Na$_2$SO$_4$. Concentration followed by flash column chromatographic purification (ethyl acetate/hexanes, 1:1 to pure ethyl acetate) gave the desired α,β-unsaturated ester 6 (22.1 g, 55%) as a pale yellow solid. MS (ES+): 351 (M+H)$^+$.

Step G: 1'-Methyl-6'-oxo-3,4,5,6,1',6'-hexahydro-2H-[4,2';4',4'']terpyridine-1-carboxylic acid benzyl ester. In a 250 mL round-bottom flask containing a stir bar was charged amide salt 2 (7.0 g, 0.037 mol) and ester 6 (13.12 g, 0.037 mol) and the mixture was dissolved in methanol (150 mL) The overall solution was added dimethylamine (40% in water, 2.4 mL, 0.019 mol) via syringe. The resulting light orange-yellow solution was heated to reflux for 45 min prior to being cooled down to room temperature. Concentration under reduced pressure followed by drying under high vacuum afforded an orange foam which was directly diluted with glacial acetic acid (150 mL) and heated under a reflux condition (oil temperature: 125° C.) for 4 hr. Removal of the solvent[11] followed by flash column chromatography (2% 2M ammonia methanol in DCM) yielded pyridone 7 (11.58 g, 77%) as a pale yellow foam. MS (ES+): 404 (M+H)$^+$.

Step H: 5'-Bromo-1'-methyl-6'-oxo-3,4,5,6,1',6'-hexahydro-2H-[4,2';4',4'']terpyridine-1-carboxylic acid benzyl ester. To a stirred solution of pyridone 7 (11.58 g, 28.7 mmol) in DCM (90 mL) was slowly added a solution of Br$_2$ (1.9 mL, 37 mmol) in DCM (20 mL) via an additional funnel in 15 min at −15° C. under nitrogen. The resulting yellow heterogeneous mixture was stirred at the same temperature for 30 min prior to being quenched with Na$_2$S$_2$O$_3$ (satd. aqueous solution) and NaHCO$_3$ (satd. aqueous solution) sequentially (25 mL each). The separated aqueous layer was extracted with DCM (50 mL×2) and the combined organic solutions were dried over MgSO$_4$ and finally concentrated. Purification under a flash column chromatographic conditions (2% 2M methanol ammonia in DCM) obtained 3-bromo-pyridone 8 (9.27 g, 67%) as a yellow foam. MS (ES+): 482 (M+H)$^+$.

Step I: 1'-Methyl-5'-naphthalen-2-yl-6'-oxo-3,4,5,6,1',6'-hexahydro-2H-[4,2';4',4'']terpyridine-1-carboxylic acid benzyl ester. To a stirred solution of 3-bromo-pyridone 8 (2.4 g, 5.01 mmol) in DME (60 mL) in a 350 mL sealable flask was degassed with bubbling nitrogen for 15 min. The overall system was then added Na$_2$CO$_3$ (2M aqueous solution, 7.5 mL) via syringe, followed by quickly adding P(o-tol)$_3$ (0.18 g, 0.6 mmol), Pd(OAc)$_2$ (56 mg, 0.25 mmol), and 2-naphthaleneboronic acid (1.3 g, 7.52 mmol) separately at room temperature under nitrogen. The overall mixture was sealed and heated at 80° C. overnight. After being cooled down to room temperature, the resulting heterogeneous was diluted with water (50 mL) and extracted with ethyl acetate (100 mL×3) and DCM (100 mL). The combined organic layers were dried over MgSO$_4$ and concentrated. The crude material was washed with a mixture of ethyl acetate-ether (20 mL each) and the resulting participate 9 was collected as a pale yellow solid (2.56 g, 97%). MS (ES+): 530 (M+H)$^+$.

Step J: 1-(2R-Hydroxy-propyl)-1'-methyl-5'-naphthalen-2-yl-1,2,3,4,5,6-hexahydro-1'H-[4,2';4',4'']terpyridin-6'-one. A yellow suspension of pyridone 9 (11.6 g, 0.021 mol) in 6N HCl (100 mL, diluted from 50 mL conc. HCl with 50 mL water) was heated to reflux for 30 min then cooled to room temperature. The resulting homogeneous yellow solution was extracted with ethyl acetate (100 mL×3) and the separated aqueous layer was neutralized with aqueous NaOH(5N) until pH~9. Extraction of the overall aqueous phase with DCM (150 mL×3) and the combined organic layers were dried over MgSO$_4$, filtrated, and concentrated to give the Cbz-deprotected product (8.2 g, 95%). The small portion of the crude product (80 mg, 0.202 mmol) was dissolved in methanol (2 mL) in a sealable tube with a stir bar to which (R)-(+)-propylene oxide (22 µL, 0.303 mmol) was added via syringe. The tube was sealed and the bright yellow solution was stirred a room temperature over night. After concentration, the resulting mixture was purified under a flash column chromatography (8% 2M methanol ammonia in DCM) to obtain the title compound (55 m g, 60%) as a yellow solid. MS (ES+): 454 (M+H)$^+$.

Example 12

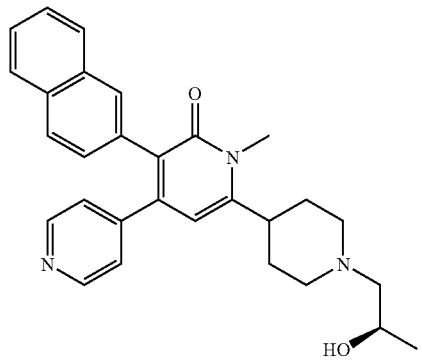

1-(2S-Hydroxy-propyl)-1'-methyl-5'-naphthalen-2-yl-1,2,3,4,5,6-hexahydro-1'H-[4,2';4',4'']terpyridin-6'-one The title compound was analogously synthesized by the method described in Example 11 using (S)-(−)-propylene oxide. This compound was obtained as yellow solid. MS (ES+): 454 (M+H)$^+$.

Example 13

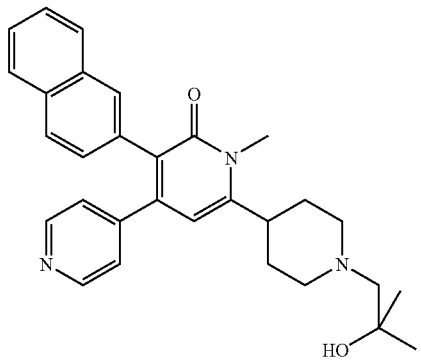

1-(2-Hydroxy-2-methyl-propyl)-1'-methyl-5'-naphthalen-2-yl-1,2,3,4,5,6-hexahydro-1'H-[4,2';4',4'']terpyridin-6'-one The title compound was analogously synthesized by the method described in Example 11 using isobutylene oxide. This compound was obtained as yellow solid. MS (ES+): 468 (M+H)+.

Example 14

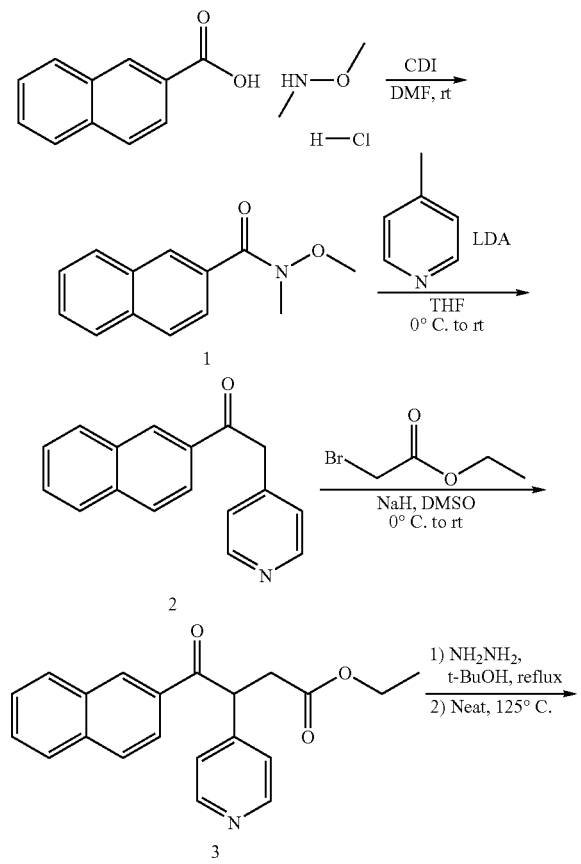

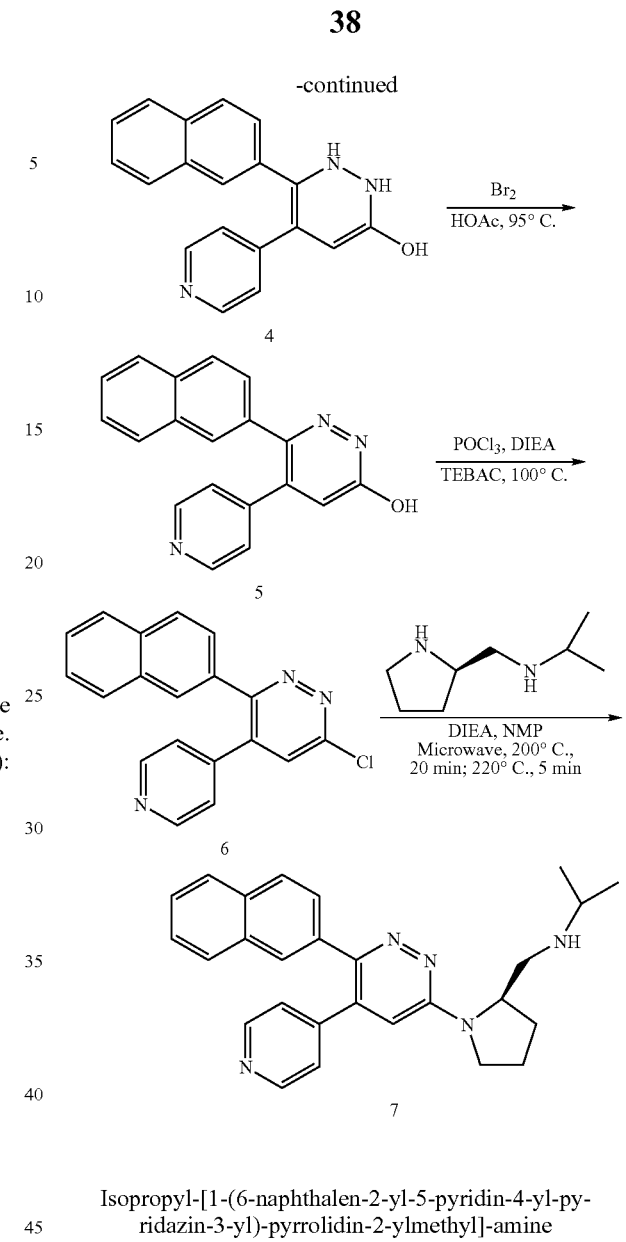

Isopropyl-[1-(6-naphthalen-2-yl-5-pyridin-4-yl-pyridazin-3-yl)-pyrrolidin-2-ylmethyl]-amine Step A: Naphthalene-2-carboxylic acid methoxy-methyl-amide In a 250 mL round-bottom flask equipped with a stir bar, was charged 2-napthoic acid (11.23 g, 65.22 mmol), N,N'-carbonyldiimidazole (15.88 g, 47.8 mmol), N,O-dimethylhydroxylamine HCl (10.27 g, 104.4 mmol) and DMF (100 mL). The resulting solution was stirred at room temperature for 48 h. The reaction was then diluted by 200 mL EtOAc and washed by 200 mL 10% HCl. The aqueous was extracted by 100 mL EtOAc and the combined organics washed with saturated sodium bicarbonate solution followed by brine. The organic layer was separated, dried by $Na_2SO_4$, and concentrated in vacuo to give 9.29 g of crude product. This was purified by flash chromatography ($SiO_2$, 2:1–1:1 Hexane:EtOAc) to give compound 1 (8.2 g, 58%) as a colorless oil. MS (ES+): 215 (M+H)+.

Step B: 1-Naphthalen-2-yl-2-pyridin-4-yl-ethanone In a 500 mL round-bottom flask equipped with a stir bar, under $N_2$, was added 4-methylpyridine (6.7 mL, 68.58 mmol) followed by anhydrous THF (100 mL). The mixture was then cooled down to −78° C. and LDA (34.3 mL, 2.0 M in THF) was added drop wise over 5 minutes. After stirring for 1.5 h at −78° C. a solution of compound 1 (15.5 g, 72.0 mmol) in anhydrous THF (100 mL) was added to the reaction mixture drop wise over 10 minutes. Stirring was continued for 1 h at −78° C. and 1 h at room temperature. The reaction was then diluted by EtOAc and washed with saturated sodium bicarbonate followed by brine. The organic layer was separated and dried over Na$_2$SO$_4$ then concentrated in vacuo to 16.64 g. The crude was purified by flash chromatography (SiO$_2$, 2:1 EtOAc:Hexane—EtOAc) yielding compound 2 (11.70 g, 69%) as a yellow/orange solid. MS (ES+): 247 (M+H)$^+$.

Step C: 4-Naphthalen-2-yl-4-oxo-3-pyridin-4-yl-butyric acid ethyl ester. In a 500 mL round-bottom flask equipped with a stir bar, under N$_2$, was added NaH (2.38 g, 56.76 mmol), followed by anhydrous DMSO (100 mL). The reaction mixture was cooled down to 0° C. and stirred for 15 minutes. Then a solution of Compound 2 (11.70 g, 47.30 mmol) in anhydrous DMSO (100 mL) was added via addition funnel at a steady drip over 15 minutes. The heterogeneous solution was stirred for 30 minutes, and then ethylbromoacetate (6.8 mL, 61.49 mmol) was added in one portion and the ice bath removed. The reaction was stirred overnight, becoming homogenous. The resulting solution was poured into saturated ammonium chloride and extracted (EtOAc, 3×). The combined organic layers were washed with saturated sodium bicarbonate, 1:1 H$_2$O:brine, followed by brine. The resulting organic layer collected, dried over Na$_2$SO$_4$ and concentrated in vacuo to 14.67 g. Purification by flash chromatography (SiO$_2$, 2:1–8:1 EtOAc:Hexane) gives compound 3 (3.06 g, 20%) as a yellow/orange solid. MS (ES+): 333 (M+H)$^+$.

Step D: 6-Naphthalen-2-yl-5-pyridin-4-yl-4H-pyridazin-3-one. Compound 3 (2.97 g, 8.91 mmol) and t-BuOH (15 mL) were charged into a 50 mL round-bottom flask equipped with a stir bar, under N$_2$. To this mixture was added hydrazine (560 μL, 17.82 mmol) and the resulting solution refluxed overnight. The reaction was concentrated in vacuo and then heated at 125° C., under vacuum for 45 minutes. The crude was purified by flash chromatography (SiO$_2$, 5% MeOH/CH$_2$Cl$_2$) to give compound 4 (2.71 g, quantitative) as a yellow solid. MS (ES+): 301 (M+H)$^+$.

Step E: 6-Naphthalen-2-yl-5-pyridin-4-yl-pyridazin-3-ol. In a 250 mL round-bottom flask equipped with a stir bar was charged compound 4 (2.71 g, 8.99 mmol) and glacial acetic acid (50 mL). The resulting solution was heated at 95° C. for 50 minutes. To this mixture was added a solution of Br$_2$ (490 μL, 9.45 mmol) in glacial acetic acid (3 mL). The reaction was stirred 1.5 h at 95° C. then concentrated in vacuo. To the crude was added EtOAc (100 mL) and H$_2$O (100 mL). The aqueous was adjusted to ~pH 8 by addition of 10% sodium carbonate. The layers were split and the aqueous extracted (EtOAc, 3×). The combined organic layers were washed with saturated sodium bicarbonate followed by brine. After drying over Na$_2$SO$_4$, the crude was concentrated in vacuo to 1.72 g. Purification by flash chromatography, (SiO$_2$, 3% MeOH/CH$_2$Cl$_2$) yields compound 5 (1.37 g, 51%) as an off-white solid. MS (ES+): 299 (M+H)$^+$.

Step F: 6-Chloro-3-naphthalen-2-yl-4-pyridin-4-yl-pyridazine—In a 250 mL round-bottom flask equipped with a stir bar was charged compound 5 (1.37 g, 4.58 mmol), tetraethylbutyl ammonium chloride (1.05 g, 4.651 mmol), diisopropylethyl amine (800 μL, 4.59 mmol) and POCl$_3$ (20 g). The resulting mixture was heated in an oil bath at 100° C. for 2 h then concentrated in vacuo. Remaining POCl$_3$ was azeotropically removed using toluene. The crude was suspended in EtOAc and iced saturated sodium bicarbonate added. The aqueous layer was extracted with EtOAc and the combined organic layers washed by saturated sodium bicarbonate followed by brine. After drying over Na$_2$SO$_4$, the crude was concentrated in vacuo to 1.46 g. Purification by flash chromatography, (SiO$_2$, 1%–3% MeOH/CH$_2$Cl$_2$) affords compound 6 (1.10 g, 76%) as an off-white solid. MS (ES+): 317 (M+H)$^+$.

Step G: Isopropyl-[1-(6-naphthalen-2-yl-5-pyridin-4-yl-pyridazin-3-yl)-pyrrolidin-2-ylmethyl]-amine—In a 2.5 mL microwave tube equipped with a spin vane, was added compound 6 (174 mg, 0.548 mmol), Isopropyl-pyrrolidin-2-ylmethyl-amine; hydrochloride (205 mg, 767 mmol), diisopropylethyl amine (477 μL, 2.7 mmol) and NMP (0.5 mL). The resulting mixture was heated by microwave at 200° C. for 20 minutes followed by heating at 220° C. for 5 minutes. The reaction was diluted with EtOAc and washed 1:1 saturated sodium bicarbonate:H$_2$O. The aqueous was extracted EtOAc and the combined organic layers washed saturated sodium bicarbonate followed by brine. The resulting organic was collected, dried over Na$_2$SO$_4$, and concentrated in vacuo to 219 mg. Purification by flash chromatography, (SiO$_2$, 3%–5% 2N NH$_3$ MeOH/CHCl$_3$) gives the title compound 7 as a light yellow solid (105 mg, 45%). MS (ES+): 423 (M+H)$^+$.

Example 15

6-[5-(Hydroxymethyl)pyrrolidin-3-yl]-1-methyl-3-(2-naphthyl)-4-(4-pyridyl)-hydropyridin-2-one

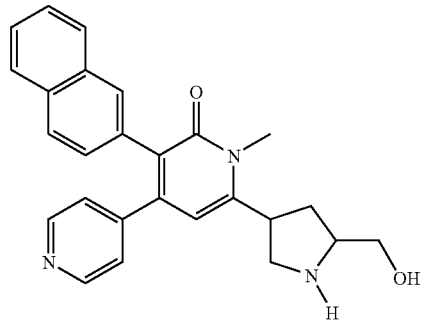

Step A. Methyl 4-{(2E)-3-(4-pyridyl)prop-2-enoyl}-1-benzylpyrrolidine-2-carboxylate.

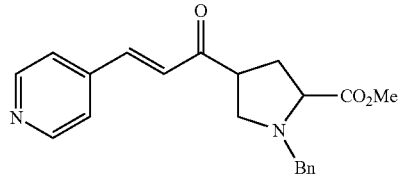

To a solution of methyl 4-acetyl-1-benzylpyrrolidine-2-carboxylate (22.83 g, 0.087 mol) in pyridine was added isonicotic aldehyde (11 mL, 0.11 mol), and La(OTf)$_3$ (5.2 g, 0.0087 mol). To this mixture was added piperidine (7.8 mL, 0.079 mol) slowly and the resulting solution was heated at 100° C. for 4 h. After cooled, the volatile material was removed and the residue was diluted with EtOAc and washed with water. The combined extracts were dried, filtered, and concentrated to give the crude product, which was purified by a flash column chromatography to obtain the title compound (11.18 g) as a pale yellow solid.

Step B. Methyl 4-(1-methyl-6-oxo-4-(4-pyridyl)(2-hydropyridyl))-1-benzylpyrrolidine-2-carboxylate.

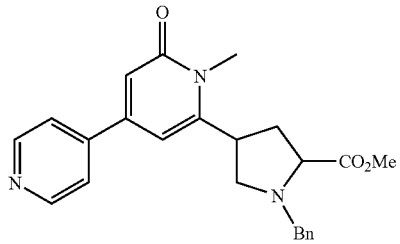

Unsaturated ketone obtained above (11.176 g, 0.032 mol) in MeOH (40 mL) was added HCl salt of N-methyl-2-pyridylacetamide (7.2 g, 0.038 mol) and dimethylamine (8 mL, 2.0M in THF, 0.0159 mol). The overall solution was refluxed for 1 h and then concentrated. The resulting foam was then redissolved in acetic acid (20 mL) and DMF (20 mL). The resulting brown was heated at 120° C. for 4 h. After concentrated, the resulting residue was subjected to a flash column chromatographic purification (3% MeOH in DCM) to afford title pyridone (8.5 g) as a 1:1 diastereomeric mixture.

Step C. 6-[5-(hydroxymethyl)-1-benzylpyrrolidin-3-yl]-1-methyl-4-(4-pyridyl)hydro-pyridin-2-one.

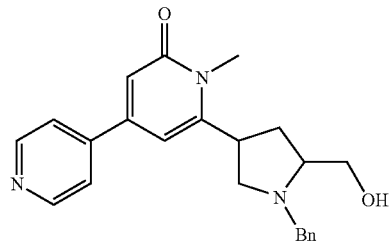

To a stirred solution of pyridone obtained above (0.8 g, 1.99 mmol) in THF (5 mL) was added 2 mL of LiBH$_4$ (2.0M in THF) at 0° C. slowly, and after addition, the overall mixture was warmed to RT for 1 h and reflux for another 1 h. The reaction was quenched, after cooling, carefully with EtOAc followed by water. The overall mixture was concentrated and then extracted with EtOAc, and the extracts were dried (Na$_2$SO$_4$) and concentrated to obtain the crude primary alcohol (0.58 g) as pale yellow solid, which was subjected to the next reaction without further purification.

Step D. 3-bromo-6-[5-(hydroxymethyl)-1-benzylpyrrolidin-3-yl]-1-methyl-4-(4-pyridyl)-hydropyridin-2-one.

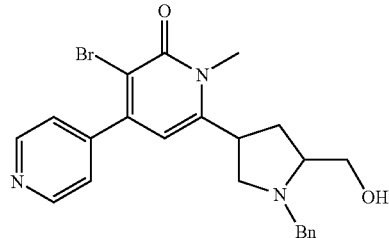

To a stirred solution of pyridone synthesized above (2.3 g, 6.13 mmol) in DCM (20 mL) was added saturated NaHCO$_3$ and water (5 mL each). The mixture was cooled to 0° C., and treated with bromine (0.5 mL, 9.2 mmol) in DCM (5 mL) slowly and the resulting heterogeneous mixture was stirred at 0° C. for another 0.5 h before being quenched with saturated aqueous Na$_2$S$_2$O$_3$ solution. The reaction mixture was extracted (DCM), washed (brine), and dried (Na$_2$SO$_4$). Concentration followed by a column chromatography (5% MeOH in DCM) provided the title compound (1.54 g) as a yellow foam.

Step E. 6-[5-(hydroxymethyl)-1-benzylpyrrolidin-3-yl]-1-methyl-3-(2-naphthyl)-4-(4-pyridyl)hydropyridin-2-one.

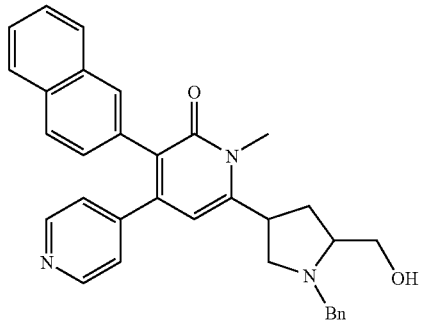

In a sellable reaction tube was charged bromopyridone (1.0 g, 2.2 mmol), dimethoxyether (10 mL). The stirred mixture was bubbled through nitrogen via needle for 10 min before Pd(OAc)$_2$ (25 mg, 0.11 mmol), tri-o-tolylphosphine (81 mg, 0.265 mmol) and boronic acid (0.57 g, 3.31 mmol) was added subsequently. The reaction tube was sealed and then heated at 80° C. over night. After cooled, the overall mixture was filtrated through a short of Celite and concentrated to give a crude product which was then purified with a flash column chromatography (5% MeOH in DCM) to provide a pure title product (0.48 g) as a yellow solid.

Step F. 6-[5-(hydroxymethyl)pyrrolidin-3-yl]-1-methyl-3-(2-naphthyl)-4-(4-pyridyl)hydropyridin-2-one and 6-[5-(hydroxymethyl)-1-methylpyrrolidin-3-yl]-1-methyl-3-(2-naphthyl)-4-(4-pyridyl)hydropyridin-2-one. To a stirred solution of benzylamine from above (0.32 g, mmol) in MeOH (10 mL) was added Pd/C (0.32 g) and then formic acid (1 mL). The entire mixture was heated at 50° C. overnight. After cooled, the resulting mixture was filtrated through Celite, washed with MeOH, and concentrated to give the crude product, which was subjected to a flash column chromatography (5% MeOH in DCM) to afford the desired de-N-benzyl product (mg) and methylated product (mg) as yellow solid.

Example 16

6-[5-(hydroxymethyl)-1-(methyl ethyl)pyrrolidin-3-yl]-1-methyl-3-(2-naphthyl)-4-(4-pyridyl)hydropyridin-2-one

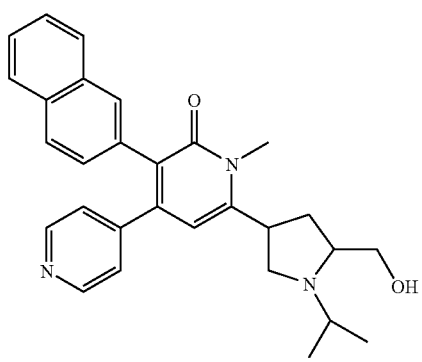

A stirred solution of amine (50 mg, 0.12 mmol) in dichloroethane (3 mL) was added acetone (18 μL, 0.24 mmol), acetic acid (2 drops) and sodium triacetoxy borohydride (64 mg, 0.31 mmol) subsequently. The overall mixture was warmed at 50° C. for 2 h prior to being cooled to room temperature and quenched with saturated aqueous sodium bicarbonate. The aqueous layer was extracted with dichloromethane and the combined organic layers were dried ($Na_2SO_4$), filtrated, and concentrated. The crude product was purified with flash column chromatography (5% MeOH in DCM) to obtain the title compound (25 mg) as a yellow solid.

Example 17

3-(4-chlorophenyl)-6-[2-(hydroxymethyl)pyrrolidinyl]-1-methyl-4-(4-pyridyl)-hydropyridin-2-one

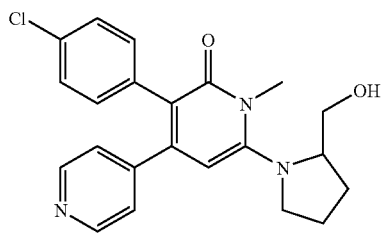

Step A. 3-(4-chlorophenyl)-1-methyl-6-[(3-oxiran-2-yl-propyl)amino]-4-(4-pyridyl)-hydropyridin-2-one.

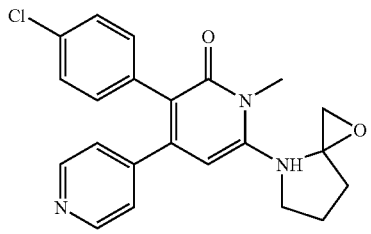

To a stirred mixture of 6-amino-3-(4-chloro-phenyl)-1-methyl-1H-[4,4']bipyridinyl-2-one (prepared using the same method as previously described for Example I) (0.31 g, 1 mmol) in DMF (4 mL) was purged with $N_2$ for 10 min, then cooled to 0° C., followed by added 1-bromo-4-epoxypentane (0.2 g, 1.2 mmol) and NaH (excess) subsequently. The resulting mixture was stirred at the same temperature for 1 h prior to being carefully quenched with saturated aqueous $NH_4Cl$ and water. The separated aqueous layer was extracted with EtOAc and the overall organic layers were washed with water, and dried ($Na_2SO_4$). Filtration and evaporation yielded a crude product, which was subjected to a flash column chromatographic purification to provide the title compound (0.37 g) as a yellow solid.

Step B. 3-(4-chlorophenyl)-6-[2-(hydroxymethyl)pyrrolidinyl]-1-methyl-4-(4-pyridyl)-hydropyridin-2-one. To a stirred solution of epoxide synthesized above in THF, after cooled to 0° C., was added NaOH (1N) aqueous solution under nitrogen and the resulting solution was heated at 50° C. overnight prior to being cooled to room temperature. The solution was diluted with $NH_4Cl$(aq) and extracted with EtOAc and the combined organic layers were dried ($Na_2SO_4$), filtrated, and evaporated. The isolated alcohol (0.29 g) was found to be pure enough to be subjected to the next reaction without further purification.

Example 18

[(1R)-Benzyl-2-(1'-methyl-5'-naphthalen-2-yl-6'-oxo-3,4,5,6,1',6'-hexahydro-2H-[4,2';4',4"]terpyridin-1-yl)-ethyl]-carbamic acid tert-butyl ester

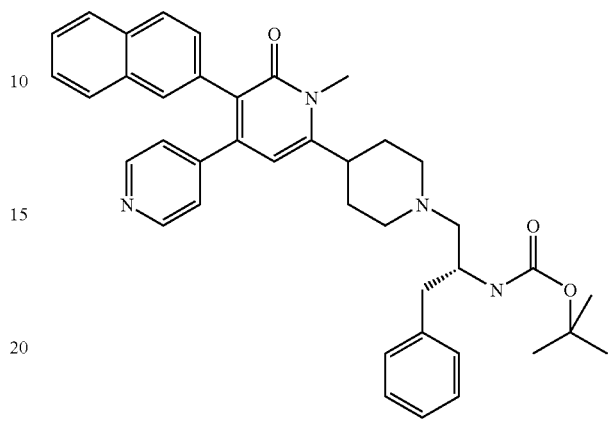

In a 50 ml oven-dried round-bottom flask equipped with stir bar under nitrogen was charged {(1R)-benzyl-2-oxo-ethyl}-carbamic acid tert-butyl (605 mg, 2.4 mmol), dry MeOH (10 mL) and 1'-methyl-5'-naphthalen-2-yl-1,2,3,4,5,6-hexahydro-1'H-[4,2';4',4"]terpyridin-6'-one (475 mg, 1.2 mmol). The resulting mixture was stirred at RT for 1 h and then cooled to −15° C. and added $NaBH_4$ slowly (138 mg, 2.6 mmol). The mixture was allowed to warm up to RT and stirred at RT for 1 h. The reaction was quenched with sat solution of $NaHCO_3$ and extracted with DCM (2×25 mL). The combined organic phases were washed with water and brine and dried over sodium sulfate. After removal of the solvent the crude was purified by flash chromatography (3% 2 M $NH_3$/MeOH in DCM) to yield the title compound (245 mg) as a yellow solid. MS (ES+): 629 (M+H)$^+$.

Example 19

1-{(2R)-Amino-3-phenyl-propyl}-1'-methyl-5'-naphthalen-2-yl-1,2,3,4,5,6-hexahydro-1'H-[4,2';4',4"] terpyridin-6'-one

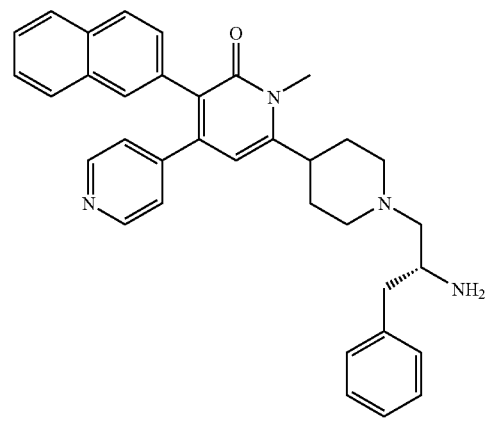

In a 50 ml oven-dried round-bottom flask equipped with stir bar under nitrogen was charged [(1R)-Benzyl-2-(1'-methyl-5'-naphthalen-2-yl-6'-oxo-3,4,5,6,1',6'-hexahydro-2H-[4,2';4',4"]terpyridin-1-yl)-ethyl]-carbamic acid tert-butyl ester (254 mg, 0.4 mmol), dry DCM (10 mL) and trifluoroacetic acid (3 mL) and then stirred at RT for 1.5 h. The mixture was then diluted with DCM and 1 N NaOH. The organic layer was taken and the aqueous was extracted again with DCM (25 mL). The combined organic phases were washed with water and brine and dried over sodium sulfate. The crude was purified by flash chromatography (3% 2 M NH$_3$/MeOH in DCM) to yield the title compound (164 mg) as a yellow solid. MS (ES+): 529 (M+H)$^+$.

Example 20

1-{(2R)-Isopropylamino-3-phenyl-propyl}-1'-methyl-5'-naphthalen-2-yl-1,2,3,4,5,6-hexahydro-1'H-[4,2';4',4"]terpyridin-6'-one

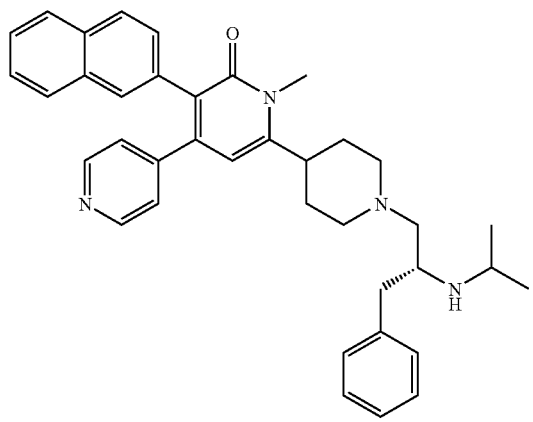

In a 50 ml oven-dried round-bottom flask equipped with stir bar under nitrogen was charged 1-{(2R)-Amino-3-phenyl-propyl}-1'-methyl-5'-naphthalen-2-yl-1,2,3,4,5,6-hexahydro-1'H-[4,2';4',4"]terpyridin-6'-one (124 mg, 0.23 mmol), dry MeOH (10 mL) and acetone (68 mg, 1.17 mmol) and then stirred at 50° C. for 1 h. After cooling down to RT 4 eq of sodium triacetoxy borohydride were added and the mixture was stirred at RT overnight. Then diluted with DCM and washed with sat. NaHCO$_3$, water and brine and dried over sodium sulfate. The crude was purified by flash chromatography (4% 2 M NH$_3$/MeOH in DCM) to yield the title compound (151 mg) as a yellow solid. MS (ES+): 571 (M+H)$^+$.

Example 21

[(1S)-Benzyl-2-(1'-methyl-5'-naphthalen-2-yl-6'-oxo-3,4,5,6,1',6'-hexahydro-2H-[4,2';4',4"]terpyridin-1-yl)-ethyl]-carbamic acid tert-butyl ester

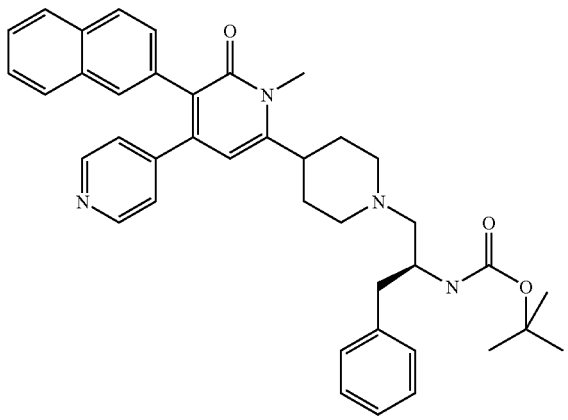

The title compound was analogously synthesized by the method described in Example 2 using {(1S)-benzyl-2-oxo-ethyl)}-carbamic acid tert-butyl. This compound was obtained as yellow solid. MS (ES+): 629 (M+H)$^+$.

Example 22

1-{(2S)-Amino-3-phenyl-propyl}-1'-methyl-5'-naphthalen-2-yl-1,2,3,4,5,6-hexahydro-1'H-[4,2';4',4"]terpyridin-6'-one

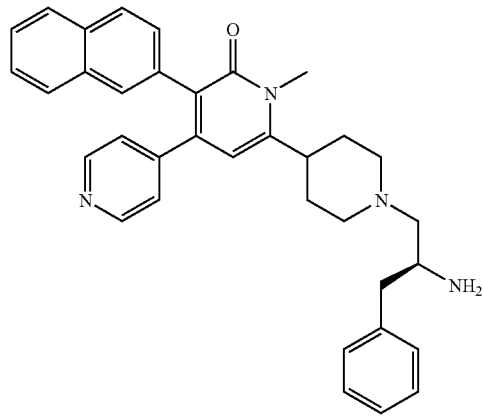

The title compound was analogously synthesized by the method described in Example 19 using [(1S)-benzyl-2-(1'-methyl-5'-naphthalen-2-yl-6'-oxo-3,4,5,6,1',6'-hexahydro-2H-[4,2';4',4"]terpyridin-1-yl)-ethyl]-carbamic acid tert-butyl ester. This compound was obtained as yellow solid. MS (ES+): 529 (M+H)$^+$.

Example 23

1-{(2S)-Isopropylamino-3-phenyl-propyl}-1'-methyl-5'-naphthalen-2-yl-1,2,3,4,5,6-hexahydro-1'H-[4,2';4',4"]terpyridin-6'-one

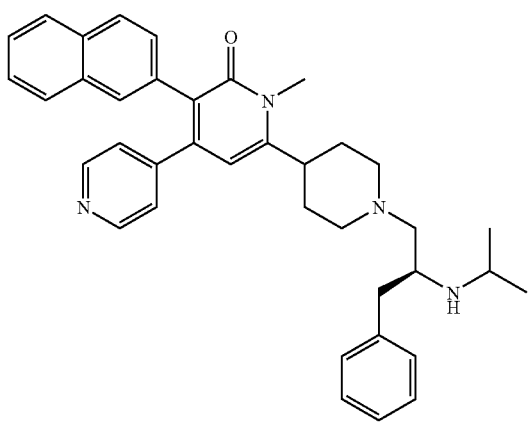

The title compound was analogously synthesized by the method described in Example 20 using 1-{(2S)-Amino-3-phenyl-propyl}-1'-methyl-5'-naphthalen-2-yl-1,2,3,4,5,6-hexahydro-1'H-[4,2';4',4"]terpyridin-6'-one. This compound was obtained as yellow solid. MS (ES+): 571 (M+H)$^+$.

Example 24

{2-[3-(1-Methyl-5-naphthalen-2-yl-6-oxo-1,6-dihydro-[4,4']bipyridinyl-2-yl)-pyrrolidin-1-yl]-ethyl}-carbamic acid tert-butyl ester

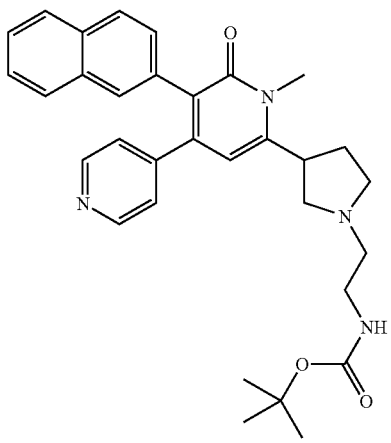

To a solution of 1-methyl-3-naphthalen-2-yl-6-pyrrolidin-3-yl-1H-[4,4']bipyridinyl-2-one (prepared following the same method as described for 1'-methyl-5'-naphthalen-2-yl-1,2,3,4,5,6-hexahydro-1'H-[4,2';4',4'']terpyridin-6'-one, Scheme 12) (200 mg, 0.52 mmol) in dry CHCl$_3$ (5 mL) under nitrogen was added (2-oxo-ethyl)-carbamic acid tert-butyl ester (209 mg, 1.3 mmol) and sodium triacetoxy borohydride (165 mg, 0.78 mmol) and then heated at 80° C. for 2 h. After cooling down to RT the mixture was diluted with CH$_2$Cl$_2$ and sat solution of NaHCO$_3$ and the organic layer was taken. The organic phase was successively washed with H$_2$O, brine and dried (Na$_2$SO$_4$). The crude was purified by flash chromatography (3%, 2M methanol ammonia in DCM) to obtain the title compound (50 mg, 18%) as a yellow solid. MS (ES+): 525 (M+H)$^+$.

Example 25

6-[1-(2-Hydroxy-propyl)-pyrrolidin-3-yl]-1-methyl-3-naphthalen-2-yl-1H-[4,4']bipyridinyl-2-one

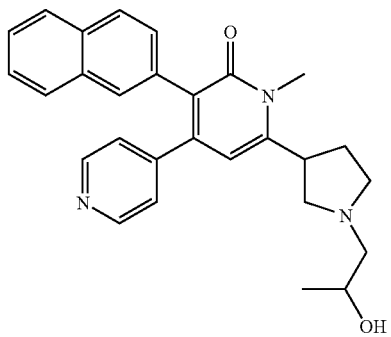

To a solution of 1-methyl-3-naphthalen-2-yl-6-pyrrolidin-3-yl-1H-[4,4']bipyridinyl-2-one (prepared following the same method as described for 1'-methyl-5'-naphthalen-2-yl-1,2,3,4,5,6-hexahydro-1'H-[4,2';4',4'']terpyridin-6'-one, Scheme 12) (0.5 g, 1.3 mmol) in dry DMF (5 mL) was added 2-methyl-oxirane (2.6 mmol, 150 mg) and then heated at 80° C. for 5 h. After cooling down to RT the solvent was removed under vacuum and the residue was purified by flash chromatography (2%, 2M methanol ammonia in DCM) to obtain the title compound (150 mg, 26%) as a yellow solid. MS (ES+): 440 (M+H)$^+$.

Example 26

6-[1-(2-Hydroxy-2-methyl-propyl)-pyrrolidin-3-yl]-1-methyl-3-naphthalen-2-yl-1H-[4,4']bipyridinyl-2-one

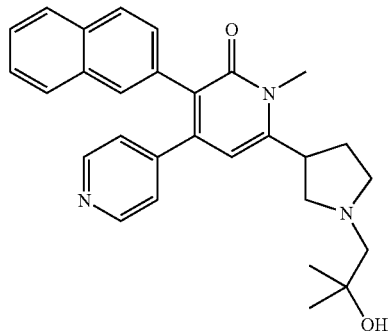

The title compound was analogously synthesized by the method described in Example 25 using 2,2-dimethyl-oxirane. This compound was obtained as yellow solid. MS (ES+): 454 (M+H)$^+$.

Example 27

{2-[2-(1-Methyl-5-naphthalen-2-yl-6-oxo-1,6-dihydro-[4,4']bipyridinyl-2-yl)-pyrrolidin-1-yl]-ethyl}-carbamic acid tert-butyl ester

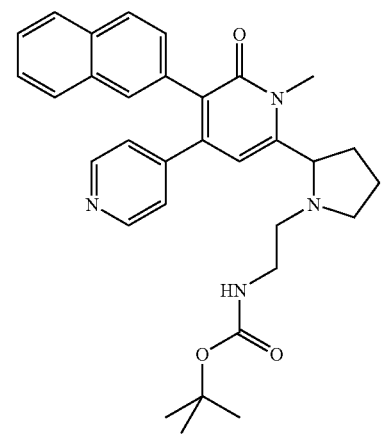

The title compound was analogously synthesized by the method described in Example 24 using 1-methyl-3-naphthalen-2-yl-6-pyrrolidin-2-yl-1H-[4,4']bipyridinyl-2-one. This compound was obtained as yellow solid. MS (ES+): 525 (M+H)$^+$.

Example 28

6-[1-(2-Amino-ethyl)-pyrrolidin-2-yl]-1-methyl-3-naphthalen-2-yl-1H-[4,4']bi-pyridinyl-2-one

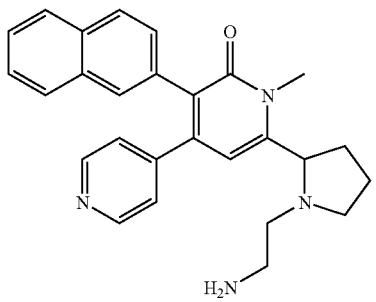

A suspension of {2-[2-(1-methyl-5-naphthalen-2-yl-6-oxo-1,6-dihydro-[4,4']bipyridinyl-2-yl)-pyrrolidin-1-yl]-ethyl}-carbamic acid tert-butyl ester (100 mg, 0.19 mmol) in sat. HCl in EtOAc was stirred at RT for 4 h. Then the title compound was isolated by filtration and washed with dry EtOAc. MS (ES+): 425 (M+H)+.

Example 29

5-Chloro-6-[2-(isopropylamino-methyl)-pyrrolidin-1-yl]-1-methyl-3-naphthalen-2-yl-1H-[4,4']bipyridinyl-2-one

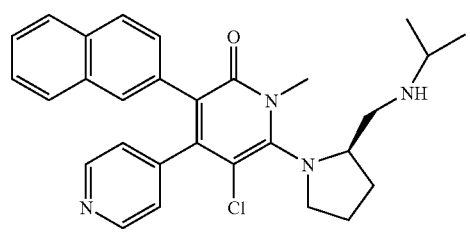

Step A: N-Methyl-2-naphthalen-2-yl-acetamide

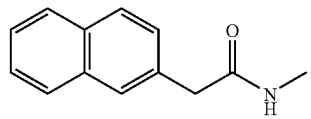

A mixture of naphthalen-2-yl-acetic acid ethyl ester (42.8 g, 200 mmol) and 64 mL of methylamine (40 wt % in H₂O) were stirred at room temperature overnight. Then the white precipitate was filtered off and washed with water. After drying in vacuum the title compound was obtained as a white solid. MS (ES+): 226 (M+H)+.

Step B: 3-Hydroxy-N-methyl-2-naphthalen-2-yl-3-pyridin-4-yl-acrylamide

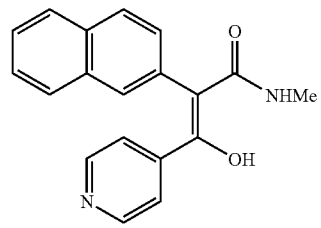

N-Methyl-2-naphthalen-2-yl-acetamide (94 g, 470 mmol) and 71.3 g (71 ml) of ethyl isonicotinate (470 mmol) were partially dissolved in 800 mL of anhydrous THF in a 3 L, 3-necked r.b. flask equipped with a mechanical stir, temperature probe, and a 500-mL addition funnel. The flask was cooled to 0–5° C. in an ice-water bath. tBuOK (1M in THF, 470 mL) was added slowly into the heterogeneous mixture. After the addition, the resulting yellow-brown heterogeneous mixture was stirred overnight at RT. The resulting dark solution was cooled to 0–5° C. in an ice-water bath. Distilled water (800 mL) was added. The basic solution was neutralized to pH 7 using 37% HCl. The solvent was removed in vacuum at RT. The resulting solid was filtered off, washed by slurring in water (1 L) and toluene (1 L), respectively. The suspension was then filtered. The solid was dried under vacuum at 50° C. overnight and used crude in the next step.

Step C: 6-Amino-1-methyl-3-naphthalen-2-yl-1H-[4,4']bipyridinyl-2-one

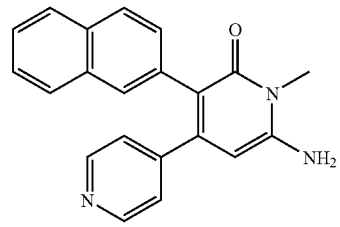

3-Hydroxy-N-methyl-2-naphthalen-2-yl-3-pyridin-4-yl-acrylamide (15.2 g, 50 mmol), NCCH₂COOH (8.51 g, 100 mmol), NH₄HCO₃ (15.8 g, 200 mmol) and AcOH (12.01 g, 11.4 mL, 200 mmol) were partially dissolved in 500 mL of toluene in a 1L, 3-necked r.b. flask equipped with a mechanical stir, temperature probe, and a Dean-Stark trap. The reaction was refluxed at 120° C. for 72 h and then the solvent was removed in vacuum. Water (100 mL) and EtOH (100 mL) were added. The acidic solution was basified to pH 12 using 5N NaOH. The resulting dark solution was refluxed at 90° C. for 2 h and then the solvent was evaporated. Dichloromethane (DCM) (100 mL) was added. The basic solution was acidified to pH 1 using 37% HCl. The aq. layer was slowly neutralized to pH 7–8 using NH₄OH. A precipitate was formed at pH 5. The resulting suspension was stirred for 1 h and the solid was filtered off and washed by toluene, dried under vacuum at RT overnight to yield the title compounds as a yellow solid. MS (ES+): 428 (M+H)+.

Step D: 5,6-Dichloro-1-methyl-3-naphthalen-2-yl-1H-[4,4']bipyridinyl-2-one

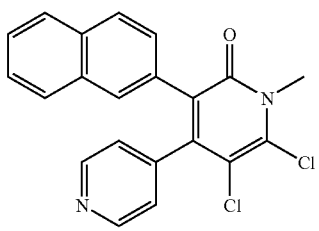

Anhydrous copper (II) chloride (1.2 eq), tert-butyl nitrite (1.5 eq) and anhydrous CH$_3$CN (40 mL) were placed into a two-neck 100-mL oven-dried round-bottom flask equipped with stir bar under nitrogen. The resulting suspension was heated to 40° C. then 6-Amino-1-methyl-3-naphthalen-2-yl-1H-[4,4']bipyridinyl-2-one (0.5 g, 1.53 mmol) was added slowly while heating. The heating was maintained at 40° C. for 20 min. The reaction was cooled to RT, quenched with 2N HCl and extracted with DCM (3×150 mL). The combined organic phases were washed with water and brine and dried over magnesium sulfate. After removal of the solvent a light yellow solid was obtained. MS (ES+): 381 (M+H)$^+$.

Step E: 5-Chloro-6-[2-(isopropylamino-methyl)-pyrrolidin-1-yl]-1-methyl-3-naphthalen-2-yl-1H-[4,4']bipyridinyl-2-one A microwave tube was charged with 5,6-dichloro-1-methyl-3-naphthalen-2-yl-1H-[4,4']bipyridinyl-2-one (0.300 g, 0.8 mmol), diisopropylethylamine (2 eq.) and isopropyl-pyrrolidin-2-ylmethyl-amine (1 eq). The heterogeneous suspension was heated in the microwave at 150° C. for 10 min. The resulting brownish suspension was dissolved in DCM and the crude product was purified by flash chromatography using an ISCO combiflash system with a mixture 97/3 DCM/MeOH to give the title compound. MS (ES+): 487 (M+H)$^+$.

Example 30

6-[2-(Isopropylamino-methyl)-pyrrolidin-1-yl]-1-methyl-3-naphthalen-2-yl-1H-4[4,4']bipyridinyl-2-one

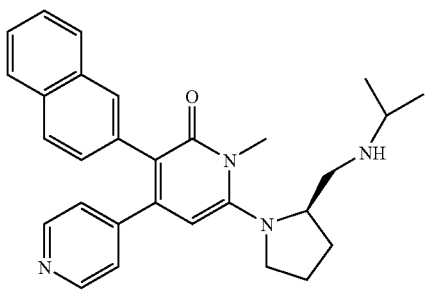

5-Chloro-6-[2-(isopropylamino-methyl)-pyrrolidin-1-yl]-1-methyl-3-naphthalen-2-yl-1H-[4,4']bipyridinyl-2-one (0.200 g, 0.41 mmol), 1–4-dioxane (10 mL) and Raney Nickel (1:7 by wt.) were placed into a 100-mL round-bottom flask equipped with stir bar under nitrogen. The resulting suspension was heated at 90° C. for 30 min. After cooling to room temperature, the mixture was filtered over celite, and the solvent was removed. The crude product was purified by flash chromatography using an ISCO combiflash system with a mixture 97/5 DCM/MeOH/NH$_3$ to give the title compound. MS (ES+): 453 (M+H)$^+$.

Example 31

3-(4-Chlorophenyl)-1-methyl-6-(2-{[(methylethyl)amino]methyl}pyrrolidinyl)-4-(4-pyridyl)hydropyridin-2-one

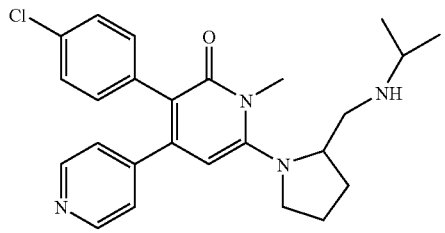

To a −78° C. stirring solution of oxalyl chloride (23 mL, 0.259 mmol) in DCM (2 mL), DMSO (0.14 mL, 1.94 mmol) was added slowly via syringe and, after stirring for 10 min, a solution of 3-(4-chlorophenyl)-6-[2-hydroxymethyl)pyrrolidinyl]-1-methyl-4-(4-pyridyl)hydropyridin-2-one (Example 17) (51 mg, 0.129 mmol) in DCM (2 mL) was added dropwise via cannula and the resulting solution was stirred at −78° C. for 20 min. The overall solution was treated with Et$_3$N (0.31 mL, 2.26 mmol) and then was slowly warmed to 0° C. for 40 min. After being diluted with water, the separated aqueous layer was extracted with DCM, and the combined organic layers were washed with brine, and then dried over Na$_2$SO$_4$. Filtration and evaporation provided the crude corresponding aldehyde, which was taken up in chloroform (5 mL) and mixed with isopropylamine (0.1 mL, 1.29 mmol), acetic acid (2 drops) and sodium triacetoxyborohydride (0.14 g, 0.65 mmol). The entire mixture was heated to 50° C. for 1 h and diluted with NaHCO$_3$ (aq) prior to being cooled down to room temperature. The separated aqueous layer was extracted with DCM and the combined organic phases were dried (Na$_2$SO$_4$) and filtrated. Removal of the solvent under reduced pressure offered the crude product, which was purified with a flash column chromatography (5% MeOH in DCM) to yield the title compound as a yellow solid.

Biological Assays

The following assays were used to characterize the ability of compounds of the invention to inhibit the production of TNF-α and IL-1-β. The second assay can be used to measure the inhibition of TNF-α and/or IL-1-β in mice after oral administration of the test compounds. The third assay, a glucagon binding inhibition in vitro assay, can be used to characterize the ability of compounds of the invention to inhibit glucagon binding. The fourth assay, a cyclooxygenase enzyme (COX-1 and COX-2) inhibition activity in vitro assay, can be used to characterize the ability of compounds of the invention to inhibit COX-1 and/or COX-2. The fifth assay, a Raf-kinase inhibition assay, can be used to characterize the compounds of the invention to inhibit phosphorylation of MEK by activated Raf-kinase.

Lipopolysaccharide-Activated Monocyte TNF Production Assay

Isolation of Monocytes

Test compounds were evaluated in vitro for the ability to inhibit the production of TNF by monocytes activated with bacterial lipopolysaccharide (LPS). Fresh residual source leukocytes (a byproduct of plateletpheresis) were obtained from a local blood bank, and peripheral blood mononuclear cells (PBMCs) were isolated by density gradient centrifugation on Ficol-Paque Plus (Pharmacia). PBMCs were suspended at $2\times10^6$/mL in DMEM supplemented to contain 2% FCS, 10 mM, 0.3 mg/mL glutamate, 100 U/mL penicillin G and 100 mg/mL streptomycin sulfate (complete media). Cells were plated into Falcon flat bottom, 96 well culture plates (200 µL/well) and cultured overnight at 37° C. and 6% $CO_2$. Non-adherent cells were removed by washing with 200 µl/well of fresh medium. Wells containing adherent cells (~70% monocytes) were replenished with 100 µL of fresh medium.

Preparation of Test Compound Stock Solutions

Test compounds were dissolved in DMZ. Compound stock solutions were prepared to an initial concentration of 10–50 µM. Stocks were diluted initially to 20–200 µM in complete media. Nine two-fold serial dilutions of each compound were then prepared in complete medium.

Treatment of Cells with Test Compounds and Activation of TNF Production with Lipopolysaccharide One hundred microliters of each test compound dilution were added to microtiter wells containing adherent monocytes and 100 µL complete medium. Monocytes were cultured with test compounds for 60 min at which time 25 µL of complete medium containing 30 ng/mL lipopolysaccharide from *E. coli* K532 were added to each well. Cells were cultured an additional 4 hrs. Culture supernatants were then removed and TNF presence in the supernatants was quantified using an ELISA.

TNF ELISA

Flat bottom, 96 well Corning High Binding ELISA plates were coated overnight (4° C.) with 150 µL/well of 3 µg/mL murine anti-human TNF-α MAb (R&D Systems #MAB210). Wells were then blocked for 1 h at room temperature with 200 µL/well of $CaCl_2$-free ELISA buffer supplemented to contain 20 mg/mL BSA (standard ELISA buffer: 20 mM, 150 mM NaCl, 2 mM $CaCl_2$, 0.15 mM thimerosal, pH 7.4). Plates were washed and replenished with 100 µL of test supernatants (diluted 1:3) or standards. Standards consisted of eleven 1.5-fold serial dilutions from a stock of 1 ng/mL recombinant human TNF (R&D Systems). Plates were incubated at room temperature for 1 h on orbital shaker (300 rpm), washed and replenished with 100 µL/well of 0.5 µg/mL goat anti-human TNF-α (R&D systems #AB-210-NA) biotinylated at a 4:1 ratio. Plates were incubated for 40 min, washed and replenished with 100 EL/well of alkaline phosphatase-conjugated streptavidin (Jackson ImmunoResearch #016-050-084) at 0.02 µg/mL. Plates were incubated 30 min, washed and replenished with 200/L/well of 1 mg/mL of p-nitrophenyl phosphate. After 30 min, plates were read at 405 nm on a $V_{max}$ plate reader.

Data Analysis

Standard curve data were fit to a second order polynomial and unknown TNF-α concentrations determined from their OD by solving this equation for concentration. TNF concentrations were then plotted vs. test compound concentration using a second order polynomial. This equation was then used to calculate the concentration of test compounds causing a 50% reduction in TNF production.

Compounds of the invention can also be shown to inhibit LPS-induced release of IL-1β, IL-6 and/or IL-8 from monocytes by measuring concentrations of IL-1β, IL-6 and/or IL-8 by methods well known to those skilled in the art. In a similar manner to the above described assay involving the LPS induced release of TNF-α from monocytes, compounds of this invention can also be shown to inhibit LPS induced release of IL-1β, IL-6 and/or IL-8 from monocytes by measuring concentrations of IL-1β, IL-6 and/or IL-8 by methods well known to those skilled in the art. Thus, the compounds of the invention may lower elevated levels of TNF-α, IL-1, IL-6, and IL-8 levels. Reducing elevated levels of these inflammatory cytokines to basal levels or below is favorable in controlling, slowing progression, and alleviating many disease states. All of the compounds are useful in the methods of treating disease states in which TNF-α, IL-1β, IL-6, and IL-8 play a role to the full extent of the definition of TNF-α-mediated diseases described herein.

Lipopolysaccharide-Activated THP1 Cell TNF Production Assay

THP1 cells are resuspended in fresh THP1 media (RPMI 1640, 10% heat-inactivated FBS, 1xPGS, 1XNEAA, plus 30 µM βME) at a concentration of 1E6/mL. One hundred microliters of cells per well are plated in a polystyrene 96-well tissue culture. One microgram per mL of bacterial LPS is prepared in THP1 media and is transferred to the wells. Test compounds are dissolved in 100% DMSO and are serially diluted 3 fold in a polypropylene 96-well microtiter plate (drug plate). HI control and LO control wells contain only DMSO. One microliter of test compound from the drug plate followed by 10 µL of LPS are transferred to the cell plate. The treated cells are induced to synthesize and secrete TNF-α at 37° C. for 3 h. Forty microliters of conditioned media are transferred to a 96-well polypropylene plate containing 110 µL of ECL buffer (50 mM Tris-HCl pH 8.0, 100 mM NaCl, 0.05% Tween 20, 0.05% $NaN_3$ and 1% FBS) supplemented with 0.44 nM MAB610 monoclonal Ab (R&D Systems), 0.34 nM ruthenylated AF210NA polyclonal Ab (R&D Systems) and 44 kg/mL sheep anti-mouse M280 Dynabeads (Dynal). After a 2 h incubation at room temperature with shaking, the reaction is read on the ECL M8 Instrument (IGEN Inc.). A low voltage is applied to the ruthenylated TNF-α immune complexes, which in the presence of TPA (the active component in Origlo), results in a cyclical redox reaction generating light at 620 nM. The amount of secreted TNF-α in the presence of compound compared with that in the presence of DMSO vehicle alone (HI control) is calculated using the formula: % control (POC)=(cpd−average LO)/(average HI−average LO)*100. Data (consisting of POC and inhibitor concentration in µM) is fitted to a 4-parameter equation ($y=A+((B-A)/(1+((x/C)^D)))$, where A is the minimum y (POC) value, B is the maximum y (POC), C is the x (cpd concentration) at the point of inflection and D is the slope factor) using a Levenburg-Marquardt non-linear regression algorithm.

The following compounds exhibit activities in the THP1 cell assay (LPS induced TNF release) with $IC_{50}$ values of 20 µM or less:

5-(4-Chloro-phenyl)-2-[2-(R)-isopropylamino-methyl)-pyrrolidin-1-yl]-3-methyl-6-pyridin-4-yl-3H-pyrimidin-4-one;

5-(4-Chloro-phenyl)-2-[2-(S)-isopropylamino-methyl)-pyrrolidin-1-yl]-3-methyl-6-pyridin-4-yl-3H-pyrimidin-4-one;

5-(3-Bromo-phenyl)-2-[2-(isopropylamino-methyl)-pyrrolidin-1-yl]-3-methyl-6-pyridin-4-yl-3H-pyrimidin-4-one;

2-[2-(Isopropylamino-methyl)-pyrrolidin-1-yl]-3-methyl-6-pyridin-4-yl-5-(3-vinyl-phenyl)-3H-pyrimidin-4-one;

5-(3-Cyclopropyl-phenyl)-2-[2-(isopropylamino-methyl)-pyrrolidin-1-yl]-3-methyl-6-pyridin-4-yl-3H-pyrimidin-4-one;

2-[2-(Isopropylamino-methyl)-pyrrolidin-1-yl]-3-methyl-6-pyridin-4-yl-5-m-tolyl-3H-pyrimidin-4-one;

2-[2-(Isopropylamino-methyl)-pyrrolidin-1-yl]-3-methyl-5-naphthalen-2-yl-6-pyridin-4-yl-3H-pyrimidin-4-one;

6-(2-Chloro-pyridin-4-yl)-2-(2-methoxymethyl-pyrrolidin-1-yl)-3-methyl-5-m-tolyl-3H-pyrimidin-4-one;

2-(2-Methoxymethyl-pyrrolidin-1-yl)-3-methyl-6-[2-(1-phenyl-ethylamino)-pyridin-4-yl]-5-m-tolyl-3H-pyrimidin-4-one;

1-(2R-Hydroxy-propyl)-1'-methyl-5'-naphthalen-2-yl-1,2,3,4,5,6-hexahydro-1'H-[4,2';4',4"]terpyridin-6'-one;

1-(2S-Hydroxy-propyl)-1'-methyl-5'-naphthalen-2-yl-1,2,3,4,5,6-hexahydro-1'H-[4,2';4',4"]terpyridin-6'-one;

1-(2-Hydroxy-2-methyl-propyl)-1'-methyl-5'-naphthalen-2-yl-1,2,3,4,5,6-hexahydro-1'H-[4,2';4',4"]terpyridin-6'-one;

Isopropyl-[1-(6-naphthalen-2-yl-5-pyridin-4-yl-pyridazin-3-yl)-pyrrolidin-2-ylmethyl]-amine;

6-[5-(Hydroxymethyl)pyrrolidin-3-yl]-1-methyl-3-(2-naphthyl)-4-(4-pyridyl)-hydropyridin-2-one;

6-[5-(Hydroxymethyl)-1-(methylethyl)pyrrolidin-3-yl]-1-methyl-3-(2-naphthyl)-4-(4-pyridyl)hydropyridin-2-one;

3-(4-Chlorophenyl)-6-[2-(hydroxymethyl)pyrrolidinyl]-1-methyl-4-(4-pyridyl)-hydropyridin-2-one;

[(1R)-Benzyl-2-(1'-methyl-5'-naphthalen-2-yl-6'-oxo-3,4,5,6, 1',6'-hexahydro-2H-[4,2';4',4"]terpyridin-1-yl)-ethyl]-carbamic acid tert-butyl ester;

1-{(2R)-Amino-3-phenyl-propyl}-1'-methyl-5'-naphthalen-2-yl-1,2,3,4,5,6-hexahydro-1'H-[4,2';4',4"]terpyridin-6'-one;

1-{(2R)-Isopropylamino-3-phenyl-propyl}-1'-methyl-5'-naphthalen-2-yl-1,2,3,4,5,6-hexahydro-1'H-[4,2';4',4"]terpyridin-6'-one;

[(1S)-Benzyl-2-(1'-methyl-5'-naphthalen-2-yl-6'-oxo-3,4,5,6, 1',6'-hexahydro-2H-[4,2';4',4"]terpyridin-1-yl)-ethyl]-carbamic acid tert-butyl ester;

1-{(2S)-Amino-3-phenyl-propyl}-1'-methyl-5'-naphthalen-2-yl-1,2,3,4,5,6-hexahydro-1'H-[4,2';4',4"]terpyridin-6'-one;

1-{(2S)-Isopropylamino-3-phenyl-propyl}-1'-methyl-5'-naphthalen-2-yl-1,2,3,4,5,6-hexahydro-1'H-[4,2';4',4"]terpyridin-6'-one;

{2-[3-(1-Methyl-5-naphthalen-2-yl-6-oxo-1,6-dihydro-[4,4']bipyridinyl-2-yl)-pyrrolidin-1-yl]-ethyl}-carbamic acid tert-butyl ester;

6-[1-(2-Hydroxy-propyl)-pyrrolidin-3-yl]-1-methyl-3-naphthalen-2-yl-1H-[4,4']bipyridinyl-2-one;

6-[1-(2-Hydroxy-2-methyl-propyl)-pyrrolidin-3-yl]-1-methyl-3-naphthalen-2-yl-1H-[4,4']bipyridinyl-2-one;

{2-[2-(1-Methyl-5-naphthalen-2-yl-6-oxo-1,6-dihydro-[4,4']bipyridinyl-2-yl)-pyrrolidin-1-yl]-ethyl}-carbamic acid tert-butyl ester;

6-[1-(2-Amino-ethyl)-pyrrolidin-2-yl]-1-methyl-3-naphthalen-2-yl-1H-[4,4']bi-pyridinyl-2-one;

5-Chloro-6-[2-(isopropylamino-methyl)-pyrrolidin-1-yl]-1-methyl-3-naphthalen-2-yl-1H-[4,4']bipyridinyl-2-one;

6-[2-(Isopropylamino-methyl)-pyrrolidin-1-yl]-1-methyl-3-naphthalen-2-yl-1H-4[4,4']bipyridinyl-2-one; and 3-(4-Chlorophenyl)-1-methyl-6-(2-{[(methylethyl)amino]methyl}pyrrolidinyl)-4-(4-pyridyl)hydropyridin-2-one.

Inhibition of LPS-Induced TNF-α Production in Mice

Male DBA/1LACJ mice are dosed with vehicle or test compounds in a vehicle (the vehicle consisting of 0.5% tragacanth in 0.03 N HCl) 30 minutes prior to lipopolysaccharide (2 mg/Kg, I.V.) injection. Ninety minutes after LPS injection, blood is collected and the serum is analyzed by ELISA for TNF-α levels.

Compounds of the invention may be shown to have anti-inflammatory properties in animal models of inflammation, including carageenan paw edema, collagen induced arthritis and adjuvant arthritis, such as the carageenan paw edema model (C. A. Winter et al Proc. Soc. Exp. Biol. Med. (1962) vol 111, p 544; K. F. Swingle, in R. A. Scherrer and M. W. Whitehouse, Eds., Anti-inflammatory Agents, Chemistry and Pharmacology, Vol. 13-II, Academic, New York, 1974, p. 33) and collagen induced arthritis (D. E. Trentham et al J. Exp. Med. (1977) vol. 146, p 857; J. S. Courtenay, Nature (New Biol.) (1980), Vol 283, p 666).

$^{125}$I-Glucagon Binding Screen with CHO/hGLUR Cells

The assay is described in WO 97/16442, which is incorporated herein by reference in its entirety.

Reagents

The reagents can be prepared as follows: (a) prepare fresh 1M o-Phenanthroline (Aldrich) (198.2 mg/mL ethanol); (b) prepare fresh 0.5M DTT (Sigma); (c) Protease Inhibitor Mix (1000×): 5 mg leupeptin, 10 mg benzamidine, 40 mg bacitracin and 5 mg soybean trypsin inhibitor per mL DMSO and store aliquots at −20° C.; (d) 250 µFM human glucagon (Peninsula): solubilize 0.5 mg vial in 575 µl 0.1N acetic acid (1 µL yields 1 µM final concentration in assay for non-specific binding) and store in aliquots at −20° C.; (e) Assay Buffer: 20 mM Tris (pH 7.8), 1 mM DTT and 3 mM o-phenanthroline; (f) Assay Buffer with 0.1% BSA (for dilution of label only; 0.01% final in assay): 10 µL 10% BSA (heat-inactivated) and 990 µL Assay Buffer; (g) $^{125}$I-Glucagon (NEN, receptor-grade, 2200 Ci/mmol): dilute to 50,000 cpm/25 µL in assay buffer with BSA (about 50 pM final concentration in assay).

Harvesting of CHO/hGLUR Cells for Assay

1. Remove media from confluent flask then rinse once each with PBS (Ca, Mg-free) and Enzyme-free Dissociation Fluid (Specialty Media, Inc.).

2. Add 10 mL Enzyme-free Dissoc. Fluid and hold for about 4 min at 37° C.

3. Gently tap cells free, triturate, take aliquot for counting and centrifuge remainder for 5 min at 1000 rpm.

4. Resuspend pellet in Assay Buffer at 75000 cells per 100 µL.

Membrane preparations of CHO/hGLUR cells can be used in place of whole cells at the same assay volume. Final protein concentration of a membrane preparation is determined on a per batch basis.

Assay

The determination of inhibition of glucagon binding can be carried out by measuring the reduction of $I^{125}$-glucagon binding in the presence of compounds of Formula I. The reagents are combined as follows:

|                      | Compound/ Vehicle | 250 μM Glucagon | $^{125}$I-Glucagon | CHO/ hGLUR Cells |
|----------------------|-------------------|-----------------|--------------------|------------------|
| Total Binding +      | —/5 μl            | —               | 25 μL              | 100 μL           |
| Compound             | 5 μl/—            | —               | 25 μL              | 100 μL           |
| Nonspecific Binding  | —/5 μl            | 1 μl            | 25 μL              | 100 μL           |

The mixture is incubated for 60 min at 22° C. on a shaker at 275 rpm. The mixture is filtered over pre-soaked (0.5% polyethylimine (PEI)) GF/C filtermat using an Innotech Harvester or Tomtec Harvester with four washes of ice-cold 20 mM Tris buffer (pH 7.8). The radioactivity in the filters is determined by a gamma-scintillation counter.

Thus, compounds of the invention may also be shown to inhibit the binding of glucagon to glucagon receptors.

Cyclooxygenase Enzyme Activity Assay

The human monocytic leukemia cell line, THP-1, differentiated by exposure to phorbol esters expresses only COX-1; the human osteosarcoma cell line 143B expresses predominantly COX-2. THP-1 cells are routinely cultured in RPMI complete media supplemented with 10% FBS and human osteosarcoma cells (HOSC) are cultured in minimal essential media supplemented with 10% fetal bovine serum (MEM-10% FBS); all cell incubations are at 37° C. in a humidified environment containing 5% $CO_2$.

COX-1 Assay

In preparation for the COX-1 assay, THP-1 cells are grown to confluency, split 1:3 into RPMI containing 2% FBS and 10 mM phorbol 12-myristate 13-acetate (TPA), and incubated for 48 h on a shaker to prevent attachment. Cells are pelleted and resuspended in Hank's Buffered Saline (HBS) at a concentration of $2.5\times10^6$ cells/mL and plated in 96-well culture plates at a density of $5\times10^5$ cells/mL. Test compounds are diluted in HBS and added to the desired final concentration and the cells are incubated for an additional 4 hours. Arachidonic acid is added to a final concentration of 30 mM, the cells incubated for 20 minutes at 37° C., and enzyme activity determined as described below.

COX-2 Assay

For the COX-2 assay, subconfluent HOSC are trypsinized and resuspended at $3\times10^6$ cells/mL in MEM-FBS containing 1 ng human IL-1b/mL, plated in 96-well tissue culture plates at a density of $3\times10^4$ cells per well, incubated on a shaker for 1 hour to evenly distribute cells, followed by an additional 2 hour static incubation to allow attachment. The media is then replaced with MEM containing 2% FBS (MEM-2% FBS) and 1 ng human IL-1b/mL, and the cells incubated for 18–22 hours. Following replacement of media with 190 mL MEM, 10 mL of test compound diluted in HBS is added to achieve the desired concentration and the cells incubated for 4 hours. The supernatants are removed and replaced with MEM containing 30 mM arachidonic acid, the cells incubated for 20 minutes at 37° C., and enzyme activity determined as described below.

COX Activity Determined

After incubation with arachidonic acid, the reactions are stopped by the addition of 1N HCl, followed by neutralization with 1N NaOH and centrifugation to pellet cell debris. Cyclooxygenase enzyme activity in both HOSC and THP-1 cell supernatants is determined by measuring the concentration of $PGE_2$ using a commercially available ELISA (Neogen #404110). A standard curve of $PGE_2$ is used for calibration, and commercially available COX-1 and COX-2 inhibitors are included as standard controls.

Raf Kinase Assay

In vitro Raf kinase activity is measured by the extent of phosphorylation of the substrate MEK (Map kinase/ERK kinase) by activated Raf kinase, as described in GB 1,238, 959 (incorporated herein by reference in its entirety). Phosphorylated MEK is trapped on a filter and incorporation of radiolabeled phosphate is quantified by scintillation counting.

Materials:
Activated Raf is produced by triple transfection of Sf9 cells with baculoviruses expressing "Glu-Glu"-epitope tagged Raf,val$^{12}$-H-Ras, and Lck. The "Glu-Glu"-epitope, Glu-Try-Met-Pro-Met-Glu, was fused to the carboxy-terminus of full length c-Raf.
Catalytically inactive MEK (K97A mutation) is produced in Sf9 cells transfected with a baculovirus expressing c-terminus "Glu-Glu" epitope-tagged K97A MEK1.
Anti "Glu-Glu" antibody was purified from cells grown as described in: Grussenmeyer, et al., Proceedings of the National Academy of Science, U.S.A. pp 7952–7954, 1985.
Column buffer: 20 mM Tris pH 8, 100 mM NaCl, 1 mM EDTA, 2.5 mM EGTA, 10 mM $MgCl_2$, 2 mM DTT, 0.4 mM AEBSF, 0.1% n-octylglucopyranoside, 1 nM okadeic acid, and 10 μg/mL each of benzamidine, leupeptin, pepstatin, and aprotinin.
5× Reaction buffer: 125 mM HEPES pH=8, 25 mM $MgCl_2$, 5 mM EDTA, 5 mM $Na_3VO_4$, 100 μg/mL BSA.
Enzyme dilution buffer: 25 mM HEPES pH 8, 1 mM EDTA, 1 mM $Na_3VO_4$, 400 μg/mL BSA.
Stop solution: 100 mM EDTA, 80 mM sodium pyrophosphate.
Filter plates: Milipore multiscreen # SE3MO78E3, Immobilon-P (PVDF).

Methods:
Protein purification: Sf9 cells were infected with baculovirus and grown as described in Williams, et al., Proceedings of the National Academy of Science, U.S.A. pp 2922–2926, 1992. All subsequent steps were preformed on ice or at 4° C. Cells were pelleted and lysed by sonication in column buffer. Lysates were spun at 17,000×g for 20 min, followed by 0.22 μm filtration. Epitope tagged proteins were purified by chromatography over GammaBind Plus affinity column to which the "Glu-Glu" antibody was coupled. Proteins were loaded on the column followed by sequential washes with two column volumes of column buffer, and eluted with 50 μg/mL Glu-Tyr-Met-Pro-Met-Glu in column buffer.
Raf kinase assay: Test compounds were evaluated using ten 3-fold serial dilutions starting at 10–100 μM. 10 μL of the test inhibitor or control, dissolved in 10% DMSO, was added to the assay plate followed by the addition of 30 μL of the a mixture containing 10 μL 5× reaction buffer, 1 mM $^{33}$P-γ-ATP (20 μCi/mL), 0.5 μL MEK (2.5 mg/mL), 1 μL 50 mM β-mercaptoethanol. The reaction was started by the addition of 10 μL of enzyme dilution buffer containing 1 mM DTT and an amount of activated Raf that produces linear kinetics over the reaction time course. The reaction was mixed and incubated at room temperature for 90 min and stopped by the addition of 50 μL stop solution. 90 μL aliquots of this stopped solution were transferred onto GFP-30 cellulose microtiter filter plates (Polyfiltronics), the filter plates washed in four well volumes of 5% phosphoric acid, allowed to dry, and then replenished with 25 μL scintillation cocktail. The plates were counted for $^{33}$P gamma emission using a TopCount Scintillation Reader.
Other compounds that can be made include:
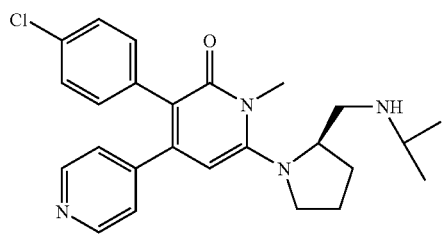
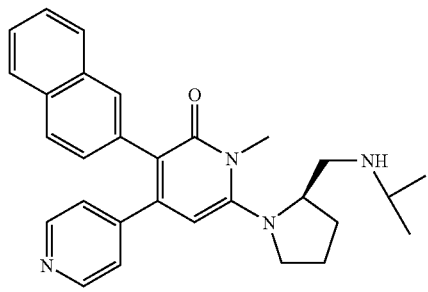
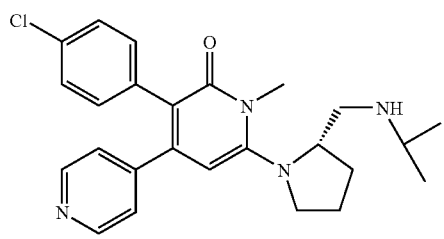
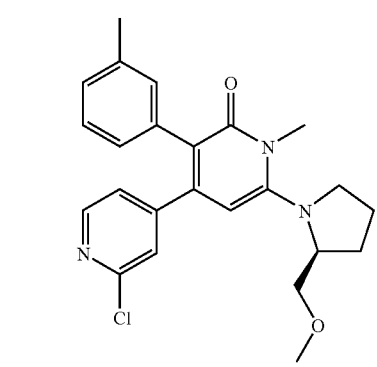
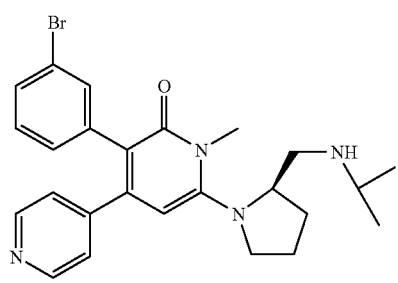
-continued
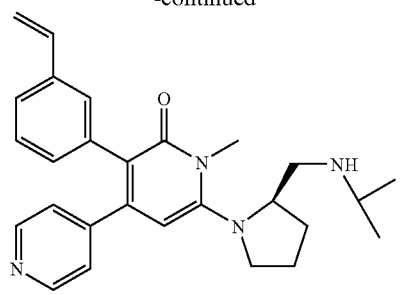
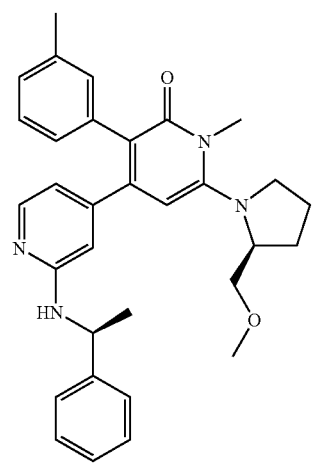
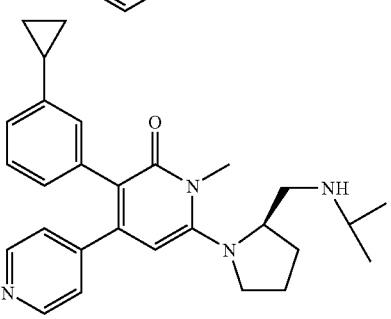
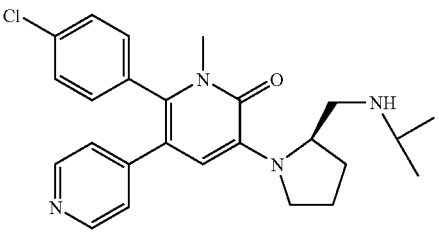
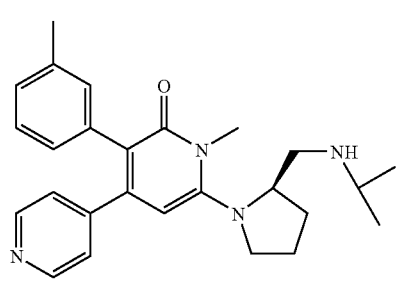

-continued
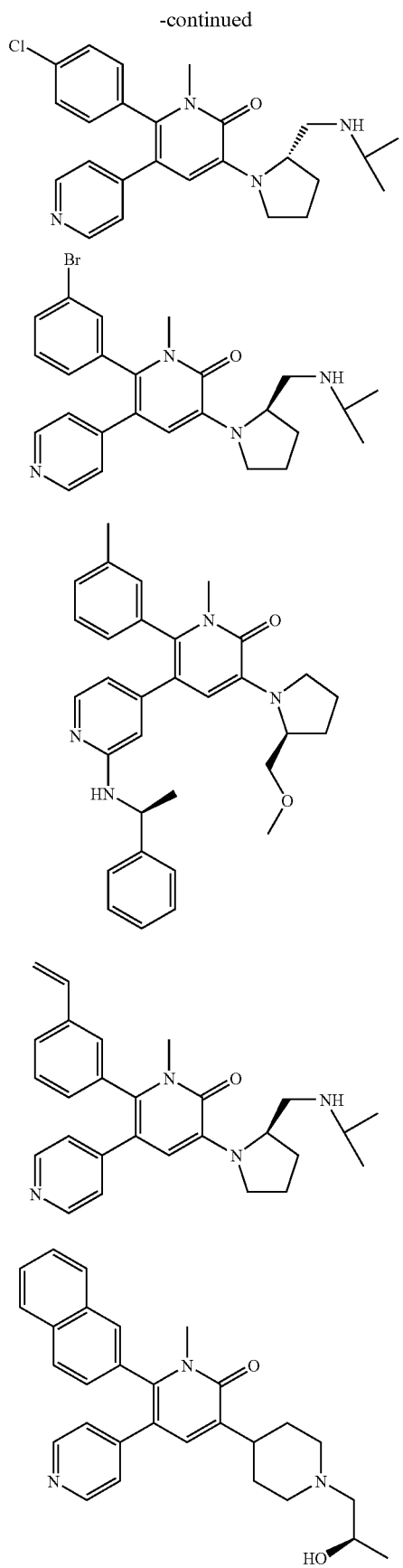
-continued
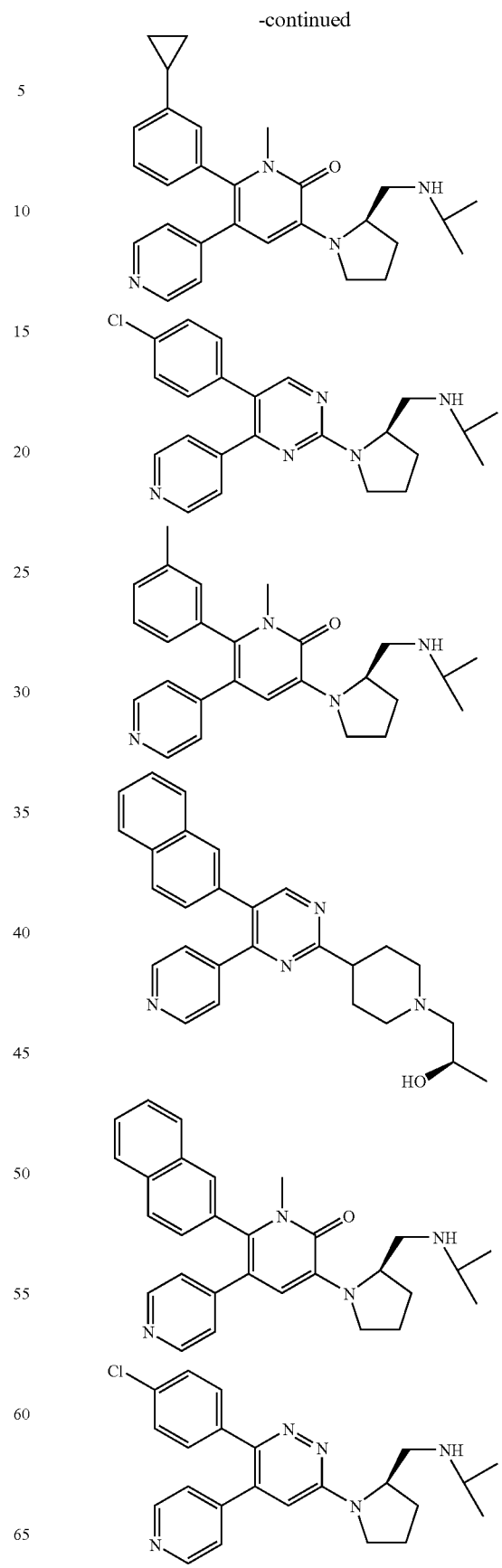

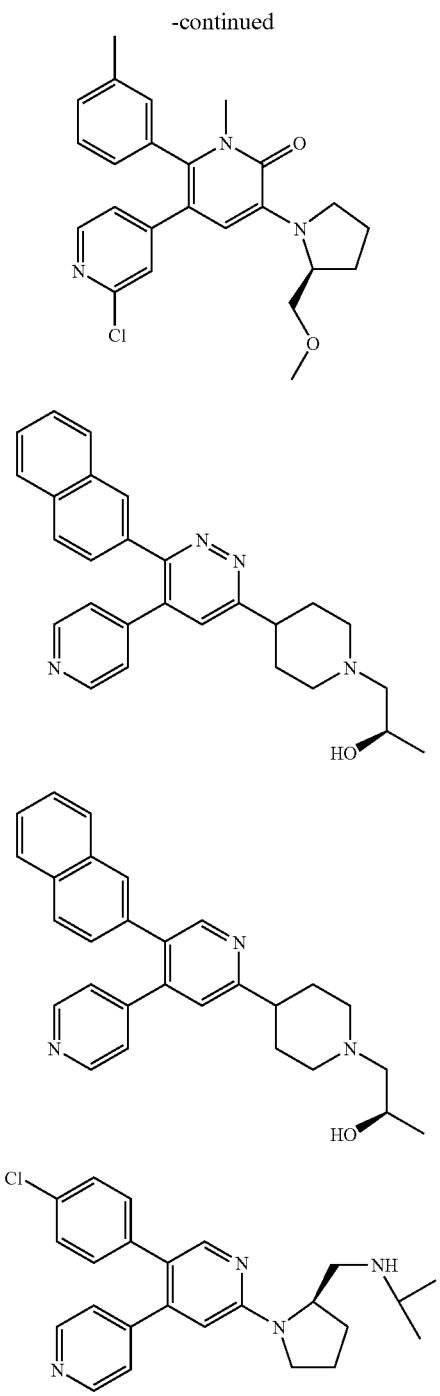

While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

For the treatment of TNF-α, IL-1β, IL-6, and IL-8 mediated diseases, cancer, and/or hyperglycemia, the compounds of the present invention may be administered orally, parentally, by inhalation spray, rectally, or topically in dosage unit formulations containing conventional pharmaceutically acceptable carriers, adjuvants, and vehicles. The term parenteral as used herein includes, subcutaneous, intravenous, intramuscular, intrasternal, infusion techniques or intraperitoneally.

Treatment of diseases and disorders herein is intended to also include the prophylactic administration of a compound of the invention, a pharmaceutical salt thereof, or a pharmaceutical composition of either to a subject (i.e., an animal, preferably a mammal, most preferably a human) believed to be in need of preventative treatment, such as, for example, pain, inflammation and the like.

The dosage regimen for treating a TNF-α, IL-1, IL-6, and L-8 mediated diseases, cancer, and/or hyperglycemia with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, preferably from about 0.1 mg to 10 mg/kg, more preferably from about 0.25 mg to 1 mg/kg are useful for all methods of use disclosed herein.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

Injectable preparations, such as sterile injectable aqueous or oleaginous suspensions, may be formulated according to the known are using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

Formulations suitable for topical administration include liquid or semi-liquid preparations suitable for penetration through the skin (e.g., liniments, lotions, ointments, creams, or pastes) and drops suitable for administration to the eye, ear, or nose.

For administration, the compounds of this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinyl-pyrrolidine, and/or polyvinyl alcohol, and tableted or encapsulated for conventional administration. Alternatively, the compounds of this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

What is claimed is:
1. A compound of formula

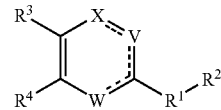

or a pharmaceutically acceptable salt thereof, wherein
n is 0, 1 or 2;
$R^1$ is a saturated or unsaturated 5-, 6- or 7-membered, ring containing 1 or 2 N atoms and 0 or 1 atoms selected from O and S, wherein the ring may be fused with a benzo group, and is substituted by 0, 1 or 2 oxo groups, and wherein $R^1$ is additionally substituted by 0, 1, 2 or 3 substituents selected from $R^d$ and $C_{1-4}$alkyl$R^d$;
$R^2$ is $C_{1-6}$alkyl substituted by 1, 2 or 3 $R^d$ groups and 0 or 1 $R^c$ groups, which are substituted by 0, 1 or 2 $R^d$ groups, wherein $R^2$ is not —C(=O)Obenzyl; and wherein —$R^1$—$R^2$ is not 3-benzylpiperazin-1-yl;
$R^3$ is aryl substituted by 0, 1, 2 or 3 substituents selected from $R^f$ and $R^d$;
$R^4$ is pyridine or pyrimidine; provided that the total number of $R^c$ groups substituted on $R^3$ is 0 or 1;
$R^5$ is independently at each instance H, $C_{1-8}$alkyl or $C^{1-6}$alkyl$R^c$ both of which are substituted by 0, 1, 2 or 3 substituents selected from $R^d$;
$R^6$ is independently at each instance $C_{1-8}$alkyl or $C^{1-6}$alkyl$R^c$ both of which are substituted by 0, 1, 2 or 3 substituents selected from $R^d$; or $R^6$ is $R^d$;
$R^7$ is independently hydrogen, —$C_{1-6}$alkyl or —$C^{1-4}$alkyl$R^c$ wherein any carbon atom in the preceding is substituted by 0–3 substituents selected from $R^d$;
$R^a$ is independently at each instance H or $R^b$;
$R^b$ is independently at each instance $C_{1-8}$alkyl, $R^c$ or $C^{1-4}$alkyl$R^c$ each of which is substituted by 0, 1, 2 or 3 substituents independently selected from $R^d$;
$R^c$ is independently at each instance aryl or a saturated or unsaturated 5-, 6- or 7-membered heterocyclic ring containing 1, 2 or 3 atoms selected from N, O and S, wherein the ring is fused with 0 or 1 benzo groups and 0 or 1 saturated or unsaturated 5-, 6- or 7-membered heterocyclic ring containing 1, 2 or 3 atoms selected from N, O and S; wherein any heterocyclic ring is substituted by 0, 1 or 2 oxo groups;
$R^d$ is independently in each instance $C_{1-6}$alkyl, halo, $C_{1-4}$haloalkyl, cyano, —C(=O)$R^f$, —C(=O)O$R^e$, —C(=O)N$R^g R^g$, —C(=N$R^g$)N$R^g R^g$, —O$R^e$, —OC(=O)$R^e$, —OC(=O)N$R^g R^g$, —OC(=O)N($R^h$)S(=O)$_2 R^f$, —S$R^e$, —S(=O)$R^f$, —S(=O)$_2 R^f$, —S(=O)$_2$N$R^g R^g$, —S(=O)$_2$N($R^h$)C(=O)$R^f$, —S(=O)$_2$N($R^h$)C(=O)O$R^f$, —S(=O)$_2$—N($R^h$)C(=O)N$R^g R^g$, —N$R^g R^g$, —N($R^h$)C(=O)$R^e$, —N($R^h$)C(=O)O$R^f$, —N($R^h$)C(=O)N$R^g R^g$, —N($R^h$)C(=N$R^g$)N$R^g R^g$, —N($R^h$)S(=O)$_2 R^f$ or —N($R^h$)S(=O)$_2$N$R^g R^g$;
$R^e$ is independently at each instance hydrogen or $R^f$;
$R^f$ is independently at each instance $R^c$ or $C_{1-8}$alkyl, either of which is substituted by 0–3 substituents selected from —N$R^g R^g$, —C(=O)O$R^i$, —O$R^i$, —N($R^i$)C(=O)$R^k$, —N($R^i$)C(=O)O$R^i$, —N($R^i$)S(=O)$_2 R^k$, —S(=O)$_n R^k$, cyano, halo, —O$C_{1-4}$alkyl$R^c$, —S(=O)$_n$$C_{1-4}$alkyl$R^c$ and $R^c$, wherein any $R^c$ in $R^f$ may be further substituted by $C_{1-8}$alkyl or $C_{1-4}$haloalkyl;

$R^g$ is independently at each instance hydrogen, $R^c$, $C_{1-10}$alkyl or —$C_{1-4}$alkyl$R^c$, wherein the each is substituted by 0–3 substituents selected from —$NR^iR^i$, —$N(R^i)C(=O)R^k$, —$N(R^i)C(=O)OR^k$, —$N(R^i)S(=O)_2R^k$, —$OR^i$, —$S(=O)_nR^k$, cyano, $C_{1-8}$alkyl and $C_{1-4}$haloalkyl;

$R^h$ is independently at each instance hydrogen, $C_{1-8}$alkyl or $C_{1-4}$alkyl$R^c$ each of which is substituted by 0–3 substituents selected from —$NR^iR^i$, —$N(R^i)C(=O)R^k$, —$N(R^i)C(=O)OR^k$, —$N(R^i)S(=O)_2R^k$, —$OR^i$, —$S(=O)_nR^k$, cyano, $C_{1-8}$alkyl and $C_{1-4}$haloalkyl;

$R^i$ is $R^k$ or hydrogen;

$R^k$ is $C_{1-6}$alkyl, phenyl or benzyl;

V is —N= or —$NR^5$;

W is —N= or —$NR^5$; and

X is —$CR^6$=, C=O, C=S or C=$NR^7$; wherein the total number of —$NR^5$—, C=O, C=S or C=$NR^7$ groups represented by V, W and X must be 0 or 2.

2. The compound according to claim 1, wherein:
$R^1$ is a saturated or unsaturated 5- or 6-membered, ring containing 1 or 2 N atoms.

3. The compound according to claim 2, wherein
$R^1$ is a saturated 5- or 6-membered, ring containing 1 N atom; and
$R^2$ is $C_{1-6}$alkyl substituted by 1 group selected from —$OR^d$ and —$NR^gR^g$, and 0 or 1 $R^d$ groups.

4. The compound according to claim 1, wherein $R^2$ is $C_{1-6}$alkyl substituted by 1 or 2 $R^d$ groups and 1 $R^c$ group, which is substituted by 0, 1 or 2 $R^d$ groups, wherein $R^2$ is not —C(=O)Obenzyl; and wherein —$R^1$—$R^2$ is not 3-benzylpiperazin-1-yl.

5. The compound that is selected from:
5-(4-Chloro-phenyl)-2-[2-(R)-isopropylamino-methyl)-pyrrolidin-1-yl]-3-methyl-6-pyridin-4-yl-3H-pyrimidin-4-one;
5-(4-Chloro-phenyl)-2-[2-(S)-isopropylamino-methyl)-pyrrolidin-1-yl]-3-methyl-6-pyridin-4-yl-3H-pyrimidin-4-one;
5-(3-Bromo-phenyl)-2-[2-(isopropylamino-methyl)-pyrrolidin-1-yl]-3-methyl-6-pyridin-4-yl-3H-pyrimidin-4-one;
2-[2-(Isopropylamino-methyl)-pyrrolidin-1-yl]-3-methyl-6-pyridin-4-yl-5-(3H-pyrimidin-4-one;
5-(3-Cyclopropyl-phenyl)-2-[2-(isopropylamino-methyl)-pyrrolidin-1-yl]-3-methyl-6-pyridin-4-yl-3H-pyrimidin-4-one;
2-[2-(Isopropylamino-methyl)-pyrrolidin-1-yl]-3-methyl-6-pyridin-4-yl-5-m-tolyl-3H-pyrimidin-4-one;
2-[2-(Isopropylamino-methyl)-pyrrolidin-1-yl]-3-methyl-5-naphthalen-2-yl-6-pyridin-4-yl-3H-pyrimidin-4-one;
6-(2-Chloro-pyridin-4-yl)-2-(2-methoxymethyl-pyrrolidin-1-yl)-3-methyl-5-m-tolyl-3H-pyrimidin-4-one; and
2-(2-Methoxymethyl-pyrrolidin-1-yl)-3-methyl-6-[2-(1-phenyl-ethylamino)-pyridin-4-yl]-5-m-tolyl-3H-pyrimidin-4-one.

6. A pharmaceutical composition comprising a compound according to claim 1 and a pharmaceutically acceptable carrier.

7. A method of treatment of inflammation comprising administering to a patient in need thereof an effective amount of a compound according to claim 1.

8. A method of making a compound according to claim 1, comprising the steps of reacting $R^1$—$R^2$, wherein $R^1$ contains a secondary ring nitrogen, with

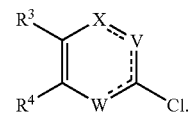

* * * * *